United States Patent
Fincher et al.

(10) Patent No.: US 9,347,069 B2
(45) Date of Patent: May 24, 2016

(54) HYBRID CAULIMOVIRUS PROMOTERS AND CONSTRUCTS THEREOF

(71) Applicant: Monsanto Technology LLC, St. Louis, MO (US)

(72) Inventors: Karen L. Fincher, Pacific, MO (US); Stanislaw Flasinski, Chesterfield, MO (US); Jack Q. Wilkinson, Redwood City, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/446,181

(22) Filed: Jul. 29, 2014

(65) Prior Publication Data

US 2015/0057155 A1   Feb. 26, 2015

Related U.S. Application Data

(60) Continuation of application No. 13/910,987, filed on Jun. 5, 2013, now Pat. No. 8,987,434, which is a continuation of application No. 13/688,188, filed on Nov. 28, 2012, now Pat. No. 8,822,666, which is a continuation of application No. 11/544,544, filed on Oct. 6, 2006, now abandoned, which is a continuation of application No. 10/920,869, filed on Aug. 18, 2004, now Pat. No. 7,141,722, which is a continuation of application No. 10/427,169, filed on May 1, 2003, now Pat. No. 6,919,495, which is a division of application No. 09/737,626, filed on Dec. 15, 2000, now Pat. No. 6,660,911.

(60) Provisional application No. 60/171,173, filed on Dec. 16, 1999.

(51) Int. Cl.

| C12N 15/00 | (2006.01) |
|---|---|
| C12N 15/09 | (2006.01) |
| C12N 15/11 | (2006.01) |
| C12N 15/52 | (2006.01) |
| C12N 15/82 | (2006.01) |
| C12N 9/10 | (2006.01) |
| A01N 57/20 | (2006.01) |

(52) U.S. Cl.
CPC ............ *C12N 15/8275* (2013.01); *A01N 57/20* (2013.01); *C12N 9/1092* (2013.01); *C12N 15/823* (2013.01); *C12N 15/8216* (2013.01); *C12N 15/8222* (2013.01); *C12N 15/8223* (2013.01); *C12N 15/8261* (2013.01); *C12N 15/8286* (2013.01)

(58) Field of Classification Search
None
See application file for complete search history.

(56) References Cited

U.S. PATENT DOCUMENTS

| 5,106,739 | A | 4/1992 | Comai et al. |
|---|---|---|---|
| 5,177,011 | A | 1/1993 | Shewmaker et al. |
| 5,196,525 | A | 3/1993 | McPherson et al. |
| 5,424,200 | A | 6/1995 | McPherson et al. |
| 5,633,435 | A | 5/1997 | Barry et al. |
| 5,773,698 | A | 6/1998 | Leroux et al. |
| 5,776,760 | A | 7/1998 | Barry et al. |
| 5,792,930 | A | 8/1998 | Chaubet et al. |
| 5,804,425 | A | 9/1998 | Barry et al. |
| 5,994,521 | A | 11/1999 | Maiti et al. |
| 6,051,753 | A | 4/2000 | Comai et al. |
| 6,407,316 | B1 | 6/2002 | Holmes et al. |
| 6,448,476 | B1 | 9/2002 | Barry |
| 6,462,258 | B1 | 10/2002 | Fincher et al. |
| 6,645,765 | B1 | 11/2003 | Anderson et al. |
| 6,660,911 | B2 | 12/2003 | Fincher et al. |
| 6,919,495 | B2 | 7/2005 | Fincher et al. |
| 6,949,696 | B2 | 9/2005 | Fincher et al. |
| 7,064,249 | B2 | 6/2006 | Corbin et al. |
| 7,112,725 | B2 | 9/2006 | Fincher et al. |
| 7,141,722 | B2 | 11/2006 | Fincher et al. |
| 2007/0022494 | A1 | 1/2007 | Fincher et al. |
| 2007/0094746 | A1 | 4/2007 | Fincher et al. |

FOREIGN PATENT DOCUMENTS

| WO | WO 92/00377 | 1/1992 |
|---|---|---|
| WO | WO 92/04449 | 3/1992 |
| WO | WO 92/12249 | 7/1992 |
| WO | WO 92/18625 | 10/1992 |
| WO | WO 95/01439 | 1/1995 |
| WO | WO 97/32028 | 9/1997 |
| WO | WO 98/00534 | 1/1998 |
| WO | WO 98/49331 | 11/1998 |
| WO | WO 98/58069 | 12/1998 |
| WO | WO 98/59039 | 12/1998 |
| WO | WO 99/05265 | 2/1999 |

(Continued)

OTHER PUBLICATIONS

Franck et al., "Nucleotide sequence of cauliflower mosaic virus DNA," *Cell* 21:285-294, 1980.

(Continued)

*Primary Examiner* — Maria Marvich

(74) *Attorney, Agent, or Firm* — Dentons US LLP; Pamela Sisson, Esq.

(57) ABSTRACT

The present invention relates to novel hybrid promoters comprising a caulimovirus promoter operably linked to one or more of an EF1α, Act8, Act2 or Act11 promoter. The present invention also relates to novel DNA constructs comprising at least one expression cassette which comprises the hybrid promoter thereof. The present invention further relates to transgenic plants/seeds comprising such DNA constructs.

24 Claims, 18 Drawing Sheets

(56) References Cited

FOREIGN PATENT DOCUMENTS

| WO | WO 99/23232 | 5/1999 |
|---|---|---|
| WO | WO 99/46370 | 9/1999 |
| WO | WO 00/32800 | 6/2000 |
| WO | WO 00/37661 | 6/2000 |
| WO | WO 01/44457 | 6/2001 |

OTHER PUBLICATIONS

Guilley et al., "Transcription of cauliflower mosaic virus DNA: detection of promoter sequences, and characterization of transcripts," *Cell* 30:763 773, 1982.
Metcalf et al., "Involvement of the *Escherichia coli* phn (psiD) gene cluster in assimilation of phosphorus in the form of phosphonates, phosphite, Pi esters, and Pi," *J Bacteriol* 173:587-600, 1991.
Odell et al., "Identification of DNA sequences required for activity of the cauliflower mosaic virus 35S promoter," *Nature* 313: 810-812, 1985.
An Yong-Qiang et al., "Strong constitutive expression of the Arabidopsis ACT2/ACT8 actin subclass in vegetative tissues," *Plant Journal* 10(1):107-121, 1996.
Axelos et al., "The Gene Family Encoding the Arabidopsis-Thaliana Translation Elongation Factor EF-1-Alpha Molecular Cloning Characterization and Expression," *Molecular and General Genetics* 219(1-2):106-112, 1989.
Comai et al., "Novel and Useful Properties of a Chimeric Plant Promoter Combining CAMV 35S and Mas Elements," *Plant Molecular Biology* 15(3):373-382, 1990.
Curie et al., "CIS and Trans-acting Elements Involved in the Activation of Arabidopsis-Thaliana A1 Gene Encoding the Translation Elongation Factor EF-1-Alpha," *Nucleic Acids Research* 19(6):1305-1310, 1991.
Curie et al., "Modular Organization and Developmental Activity of an *Arabidopsis thaliana* EF-1α Gene Promoter," *Mol. Gen. Genet.* 238:428-436, 1993.
Database EMBL (online), "*Arabidopsis thaliana* actin 8 (Act8) gene, complete cds," Database Accession No. U42007, Nov. 1996.
K. Datta et al., "Constitutive and Tissue-Specific Differential Expression of the crylA(b) Gene in Transgenic Rice Plants Conferring Resistance to Rice Insect Pest," *Theoretical and Applied Genetics* 97(1-2):20-30, 1998.

Day, "Genetic modification of plants; significant issues and hurdles to success," *Am. J. Clin. Nutr.* 63:651S-656S,1966.
Huang et al., "The *Arabidopsis ACT11* actin gene is strongly expressed in tissues of the emerging inflorescence, pollen, and developing ovules," *Plant Molecular Biology* 33:125-139, 1997.
Ildikó Vibók et al., "Endosperm Specific Expression of a Gliadin-Actin Hybrid Promoter in Transgenic Rice (*Oryza Sativa* L.)," *Cereal Research Communications* 27(3):241-249, 1999.
Jones et al., "Tolerance of transgenic cotton to topical applications of glyphosate," *J. Cotton Science* 3:19-26, 1999.
Kay et al., "Duplication of CaMV 35S Promoter Sequences Creates a Strong Enhancer for Plant Genes," *Science* 236(4806):1299-1302, 1987.
Maiti et al., "Promoter/Leader Deletion Analysis and Plant Expression Vectors with the Figwort Mosaic Virus (FMV) Full Length Transcript (FLt) Promoter Containing Single or Double Enhancer Domains," *Transgenic Research* 6(2):143-156, 1997.
McDowell et al., "The Arabidopsis ACT7 Actin Gene is Expressed in Rapidly Developing Tissues and Responds to Several External Stimuli," *Plant Physiology* 111:699-711, 1996.
Mazur et al., "Gene Discovery and Product Development for Grain Quality Traits," *Science* 285:372-375, 1999.
Omirulleh et al., "Activity of a Chimeric Promoter with the Doubled CaMV 35S Enhancer Element in Protoplast-Derived Cells and Transgenic Plants in Maize," *Plant Molecular Biology* 21(3):415-428, 1993.
Ow et al., "Functional regions of the cauliflower mosaic virus 35S RNA promoter determined by use of the firefly luciferase gene as a reporter of promoter activity," *Proc. Natl. Acad. Sci. USA* 84:4870-4874, 1987.
Pettigrew, "Moisture deficit effects on cotton lint yield, yield components, and boll distribution," *Agronomy Journal* 96:377-383, 2004.
Staiger et al., "Circadian Clock-regulated Expression of an RNA-Binding Protein in Arabidopsis: Characterisation of a Minimal Promoter Element," *Molecular and General Genetics* 261(4-5):811-819, 1999.
An et al., "Conserved Expression of the Arabidopsis *ACT1* and *ACT3* Actin Subclass in Organ Primordia and Mature Pollen," *The Plant Cell* 8:15-30, 1996.
GenBank Accession No. U27811, dated Apr. 17, 1997.
Huang et al., "The *Arabidopsis thaliana ACT4/ACT12* actin gene subclass is strongly expressed throughout pollen development," *The Plant Journal* 10(2):189-202, 1996.
Haihe et al., "The Gene Expression and Regulation of Cauliflower Mosaic Virus (CaMV)," *Journal of Microbiology* 19(1):34-40, 1999, abstract only.

HYBRID CAULIMOVIRUS PROMOTERS AND CONSTRUCTS THEREOF

This application is a continuation of U.S. patent application Ser. No. 13/910,987, filed Jun. 5, 2013 (issued as U.S. Pat. No. 8,987,434), which is a continuation of U.S. patent application Ser. No. 13/688,188, filed Nov. 28, 2012 (issued as U.S. Pat. No. 8,822,666), which is a continuation of U.S. patent application Ser. No. 11/544,544, filed Oct. 6, 2006, now abandoned, which is a continuation of U.S. patent application Ser. No. 10/920,869, filed Aug. 18, 2004, issued as U.S. Pat. No. 7,141,722, which is a continuation of U.S. patent application Ser. No. 10/427,169, filed May 1, 2003, issued as U.S. Pat. No. 6,919,495, which is a divisional of U.S. patent application Ser. No. 09/737,626, filed Dec. 15, 2000, issued as U.S. Pat. No. 6,660,911, which claims the benefit of priority to U.S. Provisional Patent Application Ser. No. 60/171,173, filed Dec. 16, 1999, each of the entire contents of which are incorporated herein by reference.

FIELD OF THE INVENTION

The present invention relates to the isolation and use of nucleic acid molecules for control of gene expression in plants, specifically novel plant promoters.

BACKGROUND OF THE INVENTION

One of the goals of plant genetic engineering is to produce plants with agronomically important characteristics or traits. Recent advances in genetic engineering have provided the requisite tools to produce transgenic plants that contain and express foreign genes (Kahl et al., World J. of Microbiol. Biotech. 11:449-460, 1995). Particularly desirable traits or qualities of interest for plant genetic engineering would include but are not limited to resistance to insects, fungal diseases, and other pests and disease-causing agents, tolerances to herbicides, enhanced stability or shelf-life, yield, environmental tolerances, and nutritional enhancements. The technological advances in plant transformation and regeneration have enabled researchers to take exogenous DNA, such as a gene or genes from a heterologous or a native source, and incorporate the exogenous DNA into the plant's genome. In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

In order to produce a transgenic plant, a construct that includes a heterologous gene sequence that confers a desired phenotype when expressed in the plant is introduced into a plant cell. The construct also includes a plant promoter that is operably linked to the heterologous gene sequence, often a promoter not normally associated with the heterologous gene. The construct is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

It would be advantageous to have a variety of promoters to tailor gene expression such that a gene or gene(s) is transcribed efficiently at the right time during plant growth and development, in the optimal location in the plant, and in the amount necessary to produce the desired effect. For example, constitutive expression of a gene product may be beneficial in one location of the plant but less beneficial in another part of the plant. In other cases, it may be beneficial to have a gene product produced at a certain developmental stage of the plant or in response to certain environmental or chemical stimuli. The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant that each gene is modulated or controlled for optimal expression and that the regulatory elements are diverse in order to reduce the potential of gene silencing. In light of these and other considerations, it is apparent that optimal control of gene expression and regulatory element diversity are important in plant biotechnology.

SUMMARY OF THE INVENTION

The present invention relates to DNA plant expression constructs that comprise *Arabidopsis* actin (Act) promoter sequences Act1a, Act1b, Act 2, Act3, Act7, Act8, Act11, Act12 and the elongation factor 1a (EF1a) promoter sequence, and fragments and cis elements derived from these promoters operably linked to heterologous structural gene sequences that function in crop plant cells.

Thus, according to one embodiment of the invention, a recombinant DNA construct is provided that comprises, in operable linkage, a promoter that is functional in a cell of a crop plant, the promoter comprising: at least one cis element derived from SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26; a structural DNA sequence heterologous to the promoter; and a 3' non-translated region that functions in plants to cause the addition of polyadenylated nucleotides to the 3' end of the RNA sequence. For example, the promoter may consist essentially of a 5' regulatory region derived from any of SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26 (including or excluding any intron sequences located therein). The structural gene may comprise any heterologous nucleotide sequence wherein expression of the sequence results in an agronomically useful trait or product in a transgenic crop plant.

According to another aspect of the invention is a DNA construct comprising a structural DNA sequence operably linked to the promoter sequences of the present invention that encode a protein employed to confer herbicide tolerance to a crop plant. This herbicide tolerance protein includes, but is not limited to glyphosate tolerance protein genes such as a glyphosate resistant EPSP synthase gene alone, or in combination with one or more glyphosate degrading protein genes.

According to another embodiment of the invention, DNA constructs such as those described above are provided wherein the promoter is a hybrid or chimeric promoter comprising at least one cis element derived from one or more of SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26 operably linked to a heterologous promoter sequence such as a caulimovirus promoter, for example the Cauliflower mosaic virus 35S promoter or the Figwort mosaic virus promoter.

According to another embodiment of the invention, DNA constructs, such as those described above, are provided in tandem, wherein the promoter is a hybrid or chimeric promoter comprising at least one cis element derived from one or more of SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26 operably linked to a heterologous gene sequence that expresses in transgenic crop plant cells. The chimeric promoter sequences more specifically comprising the sequences identified in SEQ ID NO:27, SEQ ID NO:28, SEQ ID NO:29, and SEQ ID NO:30.

According to another embodiment of the invention, a DNA construct such as that described above is provided wherein the structural DNA sequence is a glyphosate tolerance gene, such that when the DNA construct is introduced into a plant cell, it confers to the plant cell tolerance to an aqueous glyphosate formulation that includes at least 50 grams acid equivalent per liter (g a.e./l) of glyphosate. In other related embodiments, the DNA construct confers to the plant cell tolerance to glyphosate formulations having higher glyphosate concentrations (for example, at least 300 grams acid equivalent per liter of glyphosate. According to one embodiment, the DNA construct confers to the plant cell tolerance to at least one application of Roundup Ultra® at a rate of 16 ounces (oz) per acre, for example, and in other embodiments, glyphosate tolerance extends to one to two or more applications of 16 oz per acre, 32 oz per acre, or 64 oz per acre, for example.

According to another embodiment of the invention, transgenic crop plants are provided that are transformed with a DNA construct as described above, including monocot species and dicot species. We have discovered that the *Arabidopsis actin* and *Arabidopsis* EF1a promoters are sufficiently active in other crop plant species such as cotton, tomato, and sunflower, for example, that when used to control expression of a glyphosate tolerance gene, such as aroA:CP4, the plants tolerate commercial application rates of glyphosate, exhibiting good vegetative tolerance and low damage to reproductive tissues. Such promoters can also be used to express other genes of interest in plants, including, but not limited to, genes that confer herbicide tolerance, insect control, disease resistance, increased stability or shelf, higher yield, nutritional enhancement, expression of a pharmaceutical or other desired polypeptide product, or a desirable change in plant physiology or morphology, and so on.

According to another embodiment of the invention, transgenic crop plants are provided that are transformed with multiple DNA constructs comprising the *Arabidopsis actin* and *Arabidopsis* EF1a promoters are sufficiently active in other plant species such as cotton, tomato, sunflower, for example, that when used to control expression of a glyphosate tolerance gene such as aroA:CP4, the plants tolerated commercial application rates of glyphosate, exhibiting good vegetative tolerance and low damage to reproductive tissues. Such promoters can also be used to express other genes of interest in plants, including, but not limited to, genes that confer herbicide tolerance, insect control, disease resistance, increased stability or shelf, higher yield, nutritional enhancement, expression of a pharmaceutical or other desired polypeptide product, or a desirable change in plant physiology or morphology, and so on.

According to another embodiment of the invention, transgenic crop plants are provided that are transformed with DNA constructs comprising the *Arabidopsis actin* and *Arabidopsis* EF1a promoters as chimeric DNA molecules in fusion with caulimovirus DNA molecules having promoter activity in plants sufficiently active in other plant species such as cotton, tomato, canola, soybean, and sunflower, for example, that when used to control expression of a glyphosate tolerance gene such as aroA:CP4, the plants tolerate commercial application rates of glyphosate, exhibiting good vegetative tolerance and low damage to reproductive tissues. Such promoters can also be used to express other genes of interest in plants, including, but not limited to, genes that confer herbicide tolerance, insect control, disease resistance, increased stability or shelf, higher yield, nutritional enhancement, expression of a pharmaceutical or other desired polypeptide product, or a desirable change in plant physiology or morphology, and so on.

According to another embodiment of the invention methods are provided for expressing a structural DNA sequence in a plant. Such methods comprise, providing a DNA construct as described above, introducing the DNA construct into a plant cell, and regenerating the plant cell to produce a plant such that the structural DNA is expressible in the plant. According to a related embodiment, a method of controlling weeds is provided in which the DNA construct comprises a glyphosate tolerance gene and one applies to a crop plant transformed with the DNA construct an amount of glyphosate that is sufficient to control weeds without significantly damaging the crop plant.

BRIEF DESCRIPTION OF THE SEQUENCE LISTING

Figure 1:
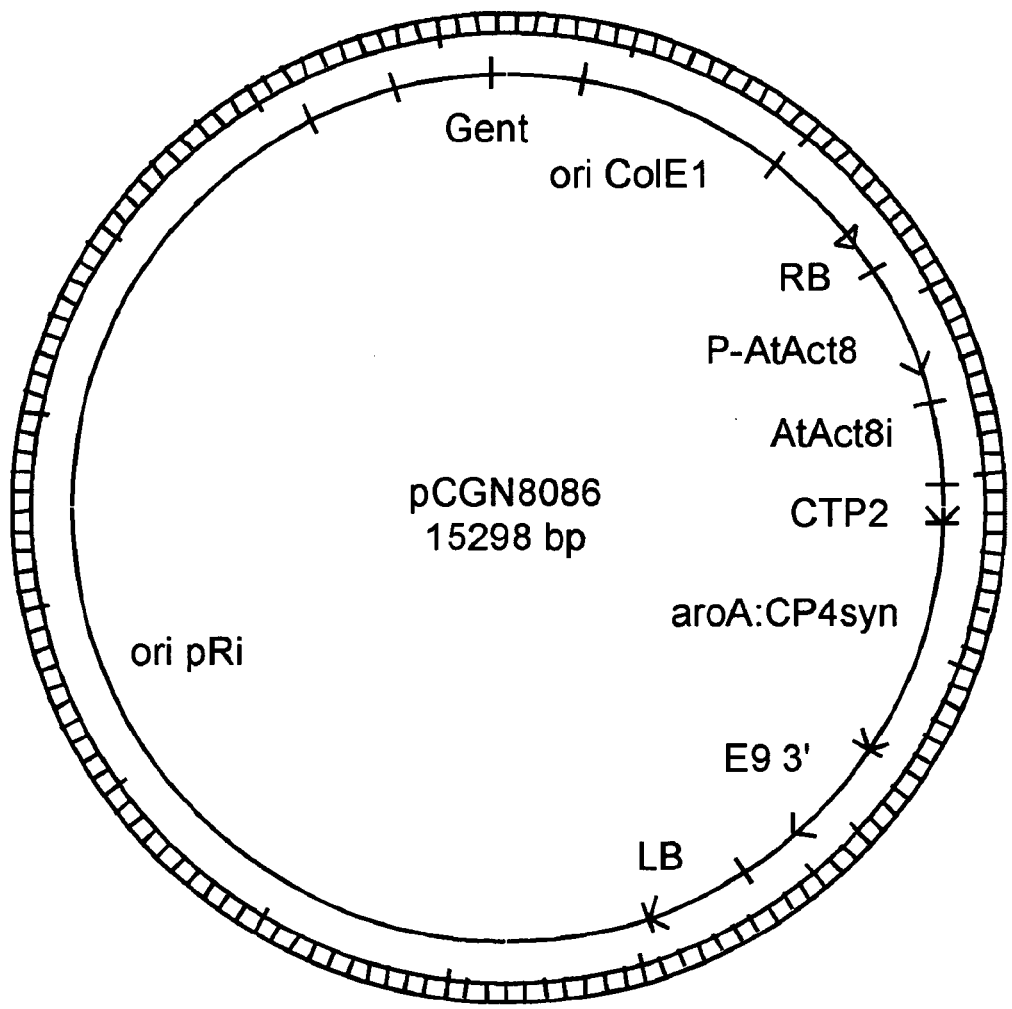
FIG. 1 is a plasmid map of pCGN8086

SEQ ID NO:1 is the forward PCR primer used for the isolation of the Act2 promoter
SEQ ID NO:2 is the reverse PCR primer used for the isolation of the Act2 promoter
SEQ ID NO:3 is the forward PCR primer used for the isolation of the Act8 promoter
SEQ ID NO:4 is the reverse PCR primer used for the isolation of the Act8 promoter
SEQ ID NO:5 is the forward PCR primer used for the isolation of the Act11 promoter
SEQ ID NO:6 is the reverse PCR primer used for the isolation of the Act11 promoter
SEQ ID NO:7 is the forward PCR primer used for the isolation of the EF1 promoter
SEQ ID NO:8 is the reverse PCR primer used for the isolation of the EF1 promoter
SEQ ID NO:9 is the sequence of the Act2 promoter including the intron sequence of the Act2 gene. Base positions 1-764 represent the promoter sequence; base positions 765-1215 represent the intron followed by 5 bases of 5' untranslated region (5' UTR) prior to the ATG; the transcription start site is located at base position 597.

SEQ ID NO:10 is the sequence of the Act8 promoter including the first intron of the Act8 gene. Base positions 1-797 represent the promoter sequence; base positions 798-1259 represent the intron followed by 10 bases of 5' UTR prior to the ATG; the transcription start site is located at base position 646.

SEQ ID NO:11 is the sequence of the Act11 promoter including the first intron of the Act11 gene. Base positions 1-1218 represent the promoter sequence; base positions 1219-1381 represent the intron followed by 10 bases of 5' UTR prior to the ATG; the transcription start site is located at base position 1062.

SEQ ID NO:12 is the sequence of the EF1 promoter including the first intron of the EF1 gene. Base positions 1-536 represent the promoter sequence; base positions 537-1137 represent the intron followed by 22 bases of 5' UTR prior to the ATG; the transcription start site is located at base position 481.

SEQ ID NO:13 is the forward PCR primer used for the isolation of the Act1a promoter SEQ ID NO:14 is the forward PCR primer used for the isolation of the Act1b promoter SEQ ID NO:15 is the reverse PCR primer used for the isolation of the Act1a and Act1b promoter SEQ ID NO:16 is the forward PCR primer used for the isolation of the Act3 promoter SEQ ID NO:17 is the reverse PCR primer used for the isolation of the Act3 promoter SEQ ID NO:18 is the forward PCR primer used for the isolation of the Act7 promoter SEQ ID NO:19 is the reverse PCR primer used for the isolation of the Act7 promoter SEQ ID NO:20 is the forward PCR primer used for the isolation of the Act12 promoter SEQ ID NO:21 is the reverse PCR primer used for the isolation of the Act12 promoter SEQ ID NO:22 is the sequence of the Act1a promoter including the first intron of the Act1a gene. Base positions 1-1033 represent the promoter sequence; base positions 1034-1578 represent the intron and 5' UTR.

SEQ ID NO:23 is the sequence of the Act1b promoter including the first intron of the Act1b gene. Base positions 1-914 represent the promoter sequence; base positions 915-1468 represent the intron and 5' UTR sequence.

SEQ ID NO:24 is the sequence of the Act3 promoter including the first intron of the Act3 gene. Base positions 1-1023 represent the promoter sequence; base positions 1024-1642 represent the intron and 5' UTR sequence.

SEQ ID NO:25 is the sequence of the Act7 promoter including the first intron of the Act7 gene. Base positions 1-600 represent the promoter sequence; base positions 601-1241 represent the intron and 5' UTR sequence.

SEQ ID NO:26 is the sequence of the Act12 promoter including the first intron of the Act12 gene. Base positions 1-1017 represent the promoter sequence; base positions 1018-1313 represent the intron and 5' UTR sequence.

SEQ ID NO:27 is the sequence of the chimeric FMV-Act11 promoter including the first intron of the Act11 gene. Base positions 1-536 represent the FMV promoter sequence; base positions 553-1946 represent the *Arabidopsis* Actin 11 promoter, intron and 5' UTR sequence.

SEQ ID NO:28 is the sequence of the chimeric FMV-EF1α promoter including the first intron of the EF1α gene. Base positions 1-536 represent the FMV promoter sequence; base positions 553-1695 represent the EF1α promoter, intron, and 5' UTR sequence.

SEQ ID NO:29 is the sequence of the CaMV-Act8 promoter including the first intron of the Act8 gene. Base positions 1-523 present the CaMV promoter sequence; base positions 534-1800 represent the Act8 promoter, intron and 5' UTR sequence.

SEQ ID NO:30 is the sequence of the CaMV-Act2 promoter including the first intron of the Act2 gene. Base positions 1-523 represent the CaMV promoter sequence; base positions 534-1742 represent the Act2 promoter, intron and 5' UTR sequence.

DETAILED DESCRIPTION OF THE INVENTION

The following definitions and methods are provided to better define, and to guide those of ordinary skill in the art in the practice of, the present invention. Unless otherwise noted, terms are to be understood according to conventional usage by those of ordinary skill in the relevant art. The nomenclature for DNA bases as set forth at 37 CFR §1.822 is used. The standard one- and three-letter nomenclature for amino acid residues is used.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence which originates from a foreign source or species or, if from the same source, is modified from its original form.

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids. The term "substantially purified", as used herein, refers to a molecule separated from other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantially identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman, Adv. Appl. Math. 2:482, 1981; by the homology alignment algorithm of Needleman and Wunsch, J. Mol. Biol. 48:443, 1970; by the search for similarity method of Pearson and Lipman, Proc. Natl. Acad. Sci. USA 85:2444, 1988; preferably by computerized implementations of these algorithms (GAP, BESTFIT, FASTA, and TFASTA) in the Wisconsin Genetics Software Package Release 7.0, Genetics Computer Group, 575 Science Dr., Madison, Wis. The reference nucleic acid may be a full-length molecule or a portion of a longer molecule. Alternatively, two nucleic acids are have substantial identity if one hybridizes to the other under stringent conditions, as defined below.

A first nucleic acid sequence is "operably linked" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see for example Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate constructs. Host cells often display a preferred pattern of codon usage (Murray et al., 1989). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc., University of Wisconsin Biotechnology Center, Madison, Wis. 53711.

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence which is annealed to a DNA template to initiate the polymerase chain reaction.

"Transformed", "transfected", or "transgenic" refers to a cell, tissue, organ, or organism into which has been introduced a foreign nucleic acid, such as a recombinant construct. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or construct.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g. rRNA, tRNA); and other types of gene function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element which may also be a component or part of an expression construct. Examples of genetic components include, but are not limited to promoter regions, 5' untranslated leaders, introns, genes, 3' untranslated regions, and other regulatory sequences or sequences which affect transcription or translation of one or more nucleic acid sequences.

The terms "recombinant DNA construct", "recombinant construct", "expression construct" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner using well-known recombinant DNA techniques.

"Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Any plant promoter can be used as a 5' regulatory sequence for modulating expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50:349-383, 1981; Messing et al., In: Genetic Engineering of Plants, Kosuge et al., eds., pp. 211-227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211-227, 1983). In addition, virtually all promoters include additional upstream activating sequences or enhancers (Benoist and Chambon, Nature 290:304-310, 1981; Gruss et al., Proc. Nat. Acad. Sci. USA 78:943-947, 1981; and Khoury and Gruss, Cell 27:313-314, 1983) extending from around −100 bp to −1,000 bp or more upstream of the transcription initiation site.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Promoters are typically comprised of multiple distinct "cis-acting transcriptional regulatory elements," or simply "cis-elements," each of which confers a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). "Cis elements" bind trans-acting protein factors that regulate transcription. Some cis elements bind more than one factor, and trans-acting transcription factors may interact with different affinities with more than one cis element (Johnson and McKnight, Ann. Rev. Biochem. 58:799-839, 1989). Plant transcription factors, corresponding cis elements, and analysis of their interaction are discussed, for example, In: Martin, Curr. Opinions Biotech. 7:130-138, 1996; Murai, In: Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300. The promoter sequences of the present invention can contain "cis elements" that confer or modulate gene expression.

Cis elements can be identified by a number of techniques, including deletion analysis, i.e., deleting one or more nucleotides from the 5' end or internal to a promoter; DNA binding protein analysis using Dnase I footprinting, methylation interference, electrophoresis mobility-shift assays, in vivo genomic footprinting by ligation-mediated PCR and other conventional assays; or by sequence similarity with known cis element motifs by conventional sequence comparison methods. The fine structure of a cis element can be further studies by mutagenesis (or substitution) of one or more nucleotides of the element or by other conventional methods (see for example, Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300).

Cis elements can be obtained by chemical synthesis or by cloning from promoters that include such elements. Cis elements can also be synthesized with additional flanking sequences that contain useful restriction enzyme sites to facilitate subsequence manipulation. In one embodiment, the promoters are comprised of multiple distinct "cis-elements". In a preferred embodiment sequence regions comprising "cis elements" of the nucleic acid sequences of SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26 are identified using computer programs including, but not limited to MEME or SIGNALSCAN that are designed specifically to identify cis elements, or domains or motifs within sequences.

The present invention includes fragments or cis elements of SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26 or homologues of cis elements known to effect gene regulation that show homology with the nucleic acid sequences of the present invention. Such nucleic acid fragments can include any region of the disclosed sequences. The promoter regions or partial promoter regions of the present invention as shown in SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26 can contain at least one regulatory element including, but not limited to "cis elements" or domains that are capable of regulating expression of operably linked DNA sequences, such as in male reproductive tissues.

Plant promoters can also include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant. Mol. Biol. 15:373-381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Chimeric or hybrid promoters according to the present invention may include at least one known cis element such as elements that are regulated by numerous environmental factors such as light, heat, or stress; elements that are regulated or induced by pathogens or chemicals, and the like. Such elements may either positively or negatively regulate gene expression, depending on the conditions. Examples of cis elements include, but are not limited to oxygen responsive elements (Cowen et al., J. Biol. Chem. 268(36):26904, 1993), light regulatory elements (see for example, Bruce and Quail, Plant Cell 2: 1081, 1990, and Bruce et al., EMBO J. 10:3015, 1991, a cis element responsive to methyl jasmonate treatment (Beaudoin and Rothstein, Plant Mol. Biol. 33:835, 1997, salicylic acid-responsive elements (Strange et al., Plant J. 11:1315, 1997, heat shock response elements (Pelham et al., Trends Genet. 1:31, 1985, elements responsive to wounding and abiotic stress (Loace et al., Proc. Natl. Acad. Sci. U.S.A. 89:9230, 1992; Mhiri et al., Plant Mol. Biol. 33:257, 1997), cold-responsive elements (Baker et al., Plant Mol. Biol. 24:701, 1994; Jiang et al., Plant Mol. Biol. 30:679, 1996; Nordin et al., Plant Mol. Biol. 21:641, 1993; Zhou et al., J. Biol. Chem. 267:23515, 1992), and drought responsive elements, (Yamaguchi et al., Plant Cell 6:251-264, 1994; Wang et al., Plant Mol. Biol. 28:605, 1995; Bray E. A. Trends in Plant Science 2:48, 1997).

In another embodiment, the nucleotide sequences as shown in SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30 includes any length of said nucleotide sequences that is capable of regulating an operably linked DNA sequence. For example, the sequences as disclosed in SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30 may be truncated or have portions deleted and still be capable of regulating transcription of an operably linked DNA sequence. In a related embodiment, a cis element of the disclosed sequences may confer a particular specificity such as conferring enhanced expression of operably linked DNA sequences in certain tissues. Consequently, any sequence fragments, portions, or regions of the disclosed sequences of SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30 can be used as regulatory sequences including but not limited to cis elements or motifs of the disclosed sequences. For example, one or more base pairs may be deleted from the 5' or 3' end of a promoter sequence to produce a "truncated" promoter. One or more base pairs can also be inserted, deleted, or substituted internally to a promoter sequence. Promoters can be constructed such that promoter fragments or elements are operably linked, for example, by placing such a fragment upstream of a minimal promoter. A minimal or basal promoter is a piece of DNA which is capable of recruiting and binding the basal transcription machinery. One example of basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region that are capable of recruiting and binding transcription factors that modulate transcription, e.g., enhance, repress, render transcription hormone-dependent, etc. Substitutions, deletions, insertions or any combination thereof can be combined to produce a final construct.

The promoter sequences of the present invention may be modified, for example for expression in other plant systems. In another approach, novel hybrid promoters can be designed or engineered by a number of methods. Many promoters contain upstream sequences which activate, enhance or define the strength and/or specificity of the promoter (Atchison, Ann. Rev. Cell Biol. 4:127, 1988). T-DNA genes, for example contain "TATA" boxes defining the site of transcription initiation and other upstream elements located upstream of the transcription initiation site modulate transcription levels (Gelvin, In: Transgenic Plants (Kung, S.-D. and Us, R., eds, San Diego: Academic Press, pp. 49-87, 1988). Another chimeric promoter combined a trimer of the octopine synthase (ocs) activator to the mannopine synthase (mas) activator plus promoter and reported an increase in expression of a reporter gene (Min Ni et al., The Plant Journal 7:661, 1995). The upstream regulatory sequences of the present invention can be used for the construction of such chimeric or hybrid promoters. Methods for construction of variant promoters of the present invention include but are not limited to combining control elements of different promoters or duplicating portions or regions of a promoter (see for example U.S. Pat. No. 5,110,732 and U.S. Pat. No. 5,097,025). Those of skill in the art are familiar with the specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

The design, construction, and use of chimeric or hybrid promoters comprising one or more of cis elements of SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26, for modulating or regulating the expression of operably linked nucleic acid sequences are also encompassed by the present invention.

The promoter sequences, fragments, regions or cis elements thereof of SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30 are capable of transcribing operably linked DNA sequences in multiple tissues and therefore can selectively regulate expression of genes in multiple tissues.

For a number of agronomic traits, transcription of a gene or genes of interest is desirable in multiple tissues to confer the desired characteristic(s). The availability of suitable promoters that regulate transcription of operably linked genes in selected target tissues of interest is desirable, since it may not be desirable to express a gene in every tissue, but only in certain tissues. For example, if one desires to selectively express a target gene for expression of gene for herbicide tolerance, one may desire expression of the herbicide tolerance gene in vegetative and reproductive tissues. The promoter sequences of the present invention are useful for regulating gene expression in multiple tissues including, but not limited to rapidly growing meristematic tissues, male reproductive tissues (androecium) such as pollen, anthers, and filaments, and female reproductive tissues (gynoecium) such as the stigma, style, and ovaries, leaves, sepals, and petals. The promoters of the present invention therefore have utility for expression of herbicide tolerance genes, for example, where tolerance is desired in multiple tissues and stages of plant development. The promoter sequences of the present invention have utility for regulating transcription of any target gene including but not limited to genes for control of fertility, yield, insect tolerance, fungal tolerance, herbicide tolerance, or any desirable trait of interest. Particularly preferred genes include herbicide tolerance genes or insect tolerance genes.

In one embodiment, the promoters of the present invention have particular utility for regulating expression of an herbicide tolerance gene where expression of a gene is desired in multiple tissues. For example, the herbicide tolerance gene may confer tolerance to the herbicide glyphosate. Examples of suitable glyphosate tolerance genes include, but are not limited to glyphosate resistant 5-enolpyruvyl-3-phosphoshikimate synthase (hereinafter referred to as EPSP synthase or EPSPS) genes or gene products that degrade glyphosate such as, a glyphosate oxidoreductase and phosphonate N-acetyl transferase. It is important to have a wide variety of choices of 5' regulatory elements for any plant biotechnology strategy in order to have suitable regulatory elements that are most efficient for the expression profile desired.

In another embodiment, the promoters of the present invention have utility for determining gene function. The function of many genes is unknown and the promoters of the present invention can be used as genetic elements in a construct to allow a phenotypic evaluation of one or more genes expressed in a sense or antisense orientation. The promoters of the present invention can be components in a plant expression construct developed for a high throughput assay where high levels of gene expression in constitutive and reproductive tissues is desired.

Any plant can be selected for the identification of genes and regulatory sequences. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yarns, and zucchini. Particularly preferred plants for the identification of regulatory sequences are *Arabidopsis*, corn, wheat, soybean, and cotton.

The promoter sequences of the present invention were isolated from *Arabidopsis thaliana* plant DNA. In a preferred embodiment, a construct includes the promoter sequences of the present invention operably linked to a transcribable sequence along with suitable terminator and regulatory elements. Such a construct may be transformed into a suitable target plant of interest. Any plant can be used as a suitable host for nucleic acid constructs comprising the promoter sequences of the present invention. Examples of suitable target plants of interest would include, but are not limited to alfalfa, broccoli, cabbage, canola, cauliflower, corn, cotton, cranberry, cucumber, lettuce, pea, poplar, pine, potato, onion, rice, raspberry, soybean, sugarcane, sugarbeet, sunflower, tomato, and wheat.

Promoter Isolation and Modification Methods

Any number of methods can be used to isolate fragments of the promoter sequences disclosed herein. A PCR-based approach can be used to amplify flanking regions from a genomic library of a plant using publicly available sequence information. A number of methods are known to those of skill in the art to amplify unknown DNA sequences adjacent to a core region of known sequence. Methods include but are not limited to inverse PCR (IPCR), vectorette PCR, Y-shaped PCR and genome walking approaches. For the present invention, the nucleic acid molecules were isolated from *Arabidopsis* by designing PCR primers based on available sequence information.

Nucleic acid fragments can also be obtained by other techniques such as by directly synthesizing the fragment by chemical means, as is commonly practiced by using an automated oligonucleotide synthesizer. Fragments can also be obtained by application of nucleic acid reproduction technology, such as the PCR (polymerase chain reaction) technology by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

Those of skill in the art are aware of methods for the preparation of plant genomic DNA. In one approach, genomic DNA libraries can be prepared from a chosen species by partial digestion with a restriction enzyme and size selecting the DNA fragments within a particular size range. The genomic DNA can be cloned into a suitable construct including but not limited to a bacteriophage, and prepared using a suitable construct such as a bacteriophage using a suitable cloning kit from any number of vendors (see for example Stratagene, La Jolla Calif. or Gibco BRL, Gaithersburg, Md.).

In another embodiment, the nucleotide sequences of the promoters disclosed herein can be modified. Those skilled in the art can create DNA molecules that have variations in the nucleotide sequence. The nucleotide sequences of the present invention as shown in SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30 may be modified or altered to enhance their control characteristics. For example, the sequences may be modified by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In addition to their use in modulating gene expression, the promoter sequences of the present invention also have utility as probes or primers in nucleic acid hybridization experiments. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure (see for example Sambrook et al., 1989, at 9.52-9.55, Sambrook et al., 1989 at 9.47-9.52, 9.56-9.58; Kanehisa, Nucl. Acids Res. 12:203-213, 1984; and Wetmur and Davidson, J. Mol. Biol. 31:349-370, 1968). Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in laboratory manuals including but not limited to Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" is they can hybridize to one another with sufficient stability to permit them to remain annealed to one another under conventional "high stringency" conditions. It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results. Conventional stringency conditions are described in Sambrook, et al., Molecular Cloning, A Laboratory Manual, $2^{nd}$ Ed., Cold Spring Harbor Press, Cold Spring Harbor, N.Y., 1989, and by Haymes et al., Nucleic Acid Hybridization, A Practical Approach, IRL Press, Washington, D.C., 1985.

In one embodiment of the present invention, the nucleic acid sequences SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26, or a fragment, region, cis element, or oligomer of these sequences, are used in hybridization assays of other plant tissues to identify closely related or homologous genes and associated regulatory sequences. These include but are not limited to Southern or northern hybridization assays on any substrate including but not limited to an appropriately prepared plant tissue, cellulose, nylon, or combination filter, chip, or glass slide. Such methodologies are well known in the art and are available in a kit or preparation which can be supplied by commercial vendors.

A fragment of a nucleic acid as used herein is a portion of the nucleic acid that is less than full-length. For example, for the present invention any length of nucleotide sequence that is less than the disclosed nucleotide sequences of SEQ ID NO:9, SEQ ID NO:10, SEQ ID NO:11, SEQ ID NO:12, SEQ ID NO:22, SEQ ID NO:23, SEQ ID NO:24, SEQ ID NO:25, and SEQ ID NO:26 is considered to be a fragment. A fragment can also comprise at least a minimum length capable of hybridizing specifically with a native nucleic acid under stringent hybridization conditions as defined above. The length of such a minimal fragment is preferably at least 8 nucleotides, more preferably 15 nucleotides, even more preferably at least 20 nucleotides, and most preferably at least 30 nucleotides of a native nucleic acid sequence.

A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the native promoter sequences disclosed herein can be used to confirm and, if necessary, to modify the disclosed sequences by conventional methods, e.g., by re-cloning and re-sequencing.

Constructs and Expression Constructs

Native or synthetic nucleic acids according to the present invention can be incorporated into recombinant nucleic acid constructs, typically DNA constructs, capable of introduction into and replication in a host cell. In a preferred embodiment, the nucleotide sequences of the present invention as shown in SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30 or fragments, variants or derivatives thereof are incorporated into an expression cassette which includes the promoter regions of the present invention operably linked to a genetic component such as a selectable, screenable, or scorable marker gene.

In another embodiment, the disclosed nucleic acid sequences of the present invention as shown in SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30 are operably linked to a genetic component such as a nucleic acid which confers a desirable characteristic associated with plant morphology, physiology, growth and development, yield, nutritional enhancement, disease or pest resistance, or environmental or chemical tolerance. These genetic components such as marker genes or agronomic genes of interest can function in the identification of a transformed plant cell or plant, or a produce a product of agronomic utility.

In another embodiment, one genetic component produces a product which serves as a selection device and functions in a regenerable plant tissue to produce a compound which would confer upon the plant tissue resistance to an otherwise toxic compound. Genes of interest for use as a selectable, screenable, or scorable marker would include but are not limited to GUS (coding sequence for beta-glucuronidase), GFP (coding sequence for green fluorescent protein), LUX (coding gene for luciferase), antibiotic resistance marker genes, or herbicide tolerance genes. Examples of transposons and associated antibiotic resistance genes include the transposons Tns (bla), Tn5 (nptII), Tn7 (dhfr), penicillins, kanamycin (and neomycin, G418, bleomycin); methotrexate (and trimethoprim); chloramphenicol; kanamycin and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I-III, Laboratory Procedures and Their Applications Academic Press, New York, 1984. Particularly preferred selectable marker genes for use in the present invention would genes which confer resistance to compounds such as antibiotics like kanamycin, and herbicides like glyphosate (Della-Cioppa et al., Bio/Technology 5(6), 1987, U.S. Pat. No. 5,463,175, U.S. Pat. No. 5,633,435). Other selection devices can also be implemented and would still fall within the scope of the present invention.

For the practice of the present invention, conventional compositions and methods for preparing and using DNA constructs and host cells are employed, as discussed, inter alia, in Sambrook et al., 1989. In a preferred embodiment, the host cell is a plant cell. A number of DNA constructs suitable for stable transfection of plant cells or for the establishment of transgenic plants have been described in, e.g., Pouwels et al., Cloning Vectors: A Laboratory Manual, 1985, supp. 1987); Weissbach and Weissbach, Methods for Plant Molecular Biology, Academic Press, 1989; Gelvin et al., Plant Molecular Biology Manual, Kluwer Academic Publishers, 1990; and R.R.D. Croy Plant Molecular Biology LabFax, BIOS Scientific Publishers, 1993. Plant expression constructs can include, for example, one or more cloned plant genes under the transcriptional control of 5' and 3' regulatory sequences. They can also include a selectable marker as described to select for host cells containing the expression construct. Such plant expression constructs also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and a polyadenylation signal. Other sequences of bacterial origin are also included to allow the construct to be cloned in a bacterial host. The construct will also typically contain a broad host range prokaryotic origin of replication. In a particularly preferred embodiment, the host cell is a plant cell and the plant expression construct comprises a promoter region as disclosed in SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30; an operably linked transcribable sequence; and a transcription termination sequence. Other regulatory sequences envisioned as genetic components in an expression construct include but is not limited to non-translated leader sequence which can be coupled with the promoter. In a particularly preferred embodiment, the host cell is a plant cell and the plant expression construct comprises a promoter region as disclosed in SEQ ID NO:9, SEQ ID NO:10, SEQ ID NO:11, SEQ ID NO:12, SEQ ID NO:22, SEQ ID NO:23, SEQ ID NO:24, SEQ ID NO:25, SEQ ID NO:26, SEQ ID NOS:27, SEQ ID NO:28, SEQ ID NO:29, and SEQ ID NO:30; an operably linked transcribable sequence, and a transcription termination sequence. Plant expression constructs also can comprise additional sequences including but not limited to polylinker sequences that contain restriction enzyme sites that are useful for cloning purposes.

Genetic Elements in Plant Expression Constructs

Plant expression constructs may include more than one expressible gene sequence, each operably linked to a different promoter. A number of promoters have utility for plant gene expression for any gene of interest including but not limited to selectable markers, scorable markers, genes for pest tolerance, disease tolerance, nutritional enhancements and any other gene of agronomic interest. Examples of constitutive promoters useful for plant gene expression include but are not limited to, the cauliflower mosaic virus (CaMV) P-35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); a tandemly duplicated version of the CaMV 35S promoter, the enhanced 35S promoter (P-e35S) the nopaline synthase promoter (An et al., Plant Physiol. 88:547, 1988), the octopine synthase promoter (Fromm et al., Plant Cell 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, or Safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989). The promoters of the present invention are plant promoters that are capable of transcribing operably linked DNA sequences in rapidly growing meristematic tissue and reproductive tissues and can be operably linked to any gene of interest in an expression construct.

Plant expression constructs can include RNA processing signals, e.g., introns, which may be positioned upstream or downstream of a polypeptide-encoding sequence in the transgene. In addition, the expression constructs may include additional regulatory sequences from the 3'-untranslated region of plant genes (Thornburg et al., Proc. Natl. Acad. Sci. USA 84:744 (1987); An et al., Plant Cell 1:115 (1989), e.g., a 3' terminator region to increase mRNA stability of the mRNA, such as the PI-II terminator region of potato or the octopine or nopaline synthase 3' terminator regions. 5' non-translated regions of a mRNA can play an important role in translation initiation and can also be a genetic component in a plant expression construct. For example, non-translated 5' leader sequences derived from heat shock protein genes have been demonstrated to enhance gene expression in plants (see, for example U.S. Pat. No. 5,362,865). These additional upstream and downstream regulatory sequences may be derived from a source that is native or heterologous with respect to the other elements present on the expression construct.

The promoter sequences of the present invention are used to control gene expression in plant cells. The disclosed promoter sequences are genetic components that are part of constructs used in plant transformation. The promoter sequences of the present invention can be used with any suitable plant transformation plasmid or construct containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance, such as a *Bacillus thuringiensis* (B. t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 9931248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463, 175, herein incorporated by reference in its entirety.

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207, 1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene which produces a protein or mRNA which expresses a phenotype or morphology change of interest is useful for the practice of the present invention.

In addition to regulatory elements or sequences located upstream (5') or within a DNA sequence, there are downstream (3') sequences that affect gene expression. Thus, the term regulatory sequence as used herein refers to any nucleotide sequence located upstream, within, or downstream to a DNA sequence which controls, mediates, or affects expression of a gene product in conjunction with the protein synthetic apparatus of the cell.

Those of skill in the art are aware of the constructs suitable for plant transformation. The promoter sequences of the present invention are preferably incorporated into an expression construct using screenable or scorable markers as described and tested in transient analyses to provide an indication of gene expression in transformed plants. Methods of testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12:612. 1993), electroporation of leaf protoplasts of wheat (Sethi et al., J. Crop Sci. 52: 152, 1983); electroporation of protoplast prepared from corn tissue (Sheen, J. The Plant Cell 3: 225, 1991), or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences of the present invention include a β-glucuronidase (GUS) gene or a green fluorescent protein (GFP) gene. The expression constructs containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the 5' regulatory sequences when operatively linked to genes of agronomic interest in stable plants. Ultimately, the 5' regulatory sequences of the present invention are directly incorporated into suitable plant transformation expression constructs comprising the 5' regulatory sequences operatively linked to a transcribable DNA sequence interest, transformed into plants and the stably transformed plants and progeny thereof analyzed for the desired expression profile conferred by the 5' regulatory sequences.

Suitable expression constructs for introducing exogenous DNA into plant cells would include but are not limited to disarmed Ti-plasmids for *Agrobacterium*-mediated methods. These constructs can contain a resistance marker, 1-2 T-DNA borders, and origins of replication for *E. coli* and *Agrobacterium* along with one or more genes of interest and associated regulatory regions. Those of skill in the art are aware that for *Agrobacterium*-mediated approaches a number of strains and methods are available. Such strains would include but are not limited to *Agrobacterium* strains C58, LBA4404, EHA101 and EHA105. Particularly preferred strains are *Agrobacterium tumefaciens* strains.

Exemplary nucleic acids which may be introduced by the methods encompassed by the present invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation constructs containing the promoter sequences of the present invention may be introduced into plants by any plant transformation method. Several methods are available for introducing DNA sequences into plant cells and are well known in the art. Suitable methods include but are not limited to bacterial infection (e.g., with *Agrobacterium* as described above), binary bacterial artificial chromosome constructs, direct delivery of DNA (e.g. via PEG-mediated transformation, desiccation/inhibition-mediated DNA uptake, electroporation, agitation with silicon carbide fibers), and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. No. 5,004,863; U.S. Pat. No. 5,159,135; U.S. Pat. No. 5,518,908, WO 97/43430), soybean (U.S. Pat. No. 5,569,834; U.S. Pat. No. 5,416,011; McCabe et al., Bio/Technology, 6:923, 1988; Christou et al., Plant Physiol., 87:671, 1988); *Brassica* (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes, C. A., et al., Science, 240: 204, 1988; Gordon-Kamm, et al., Plant Cell, 2: 603, 1990; Fromm, et al., Bio/Technology, 8: 833, 1990; Koziel, et al., Bio/Technology, 11: 194, 1993); oats (*Avena sativa*; Somers, et al., Bio/Technology, 10: 1589, 1992); orchardgrass (*Dactylis glomerata*; Horn, et al., Plant Cell Rep., 7: 469, 1988); rice (*Oryza sativa*, including indica and japonica varieties, Toriyama, et al., Bio/Technology, 6: 10, 1988; Zhang, et al., Plant Cell Rep., 7: 379, 1988; Luo and Wu, Plant Mol. Biol. Rep., 6: 165, 1988; Zhang and Wu, Theor. Appl. Genet., 76: 835, 1988; Christou, et al., Bio/Technology, 9: 957, 1991); sorghum (*Sorghum bicolor*; Casas, A. M., et al., Proc. Natl. Acad. Sci. U.S.A., 90: 11212, 1993); sugar cane (*Saccharum* spp.; Bower and Birch, Plant J., 2: 409, 1992); tall fescue (*Festuca arundinacea*; Wang, Z. Y. et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks T., et al., Plant Physiol., 102: 1077, 1993; Becker, et al., Plant, J. 5: 299, 1994), and alfalfa (Masoud, S. A., et al., Transgen. Res., 5: 313, 1996). It is apparent to those of skill in the art that a number of transformation methodologies can be used and modified for production of stable transgenic plants from any number of target crops of interest.

Plant Analysis Methods

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including but not limited to PCR technologies, genomic DNA isolation, expression construct construction, transient assays, and plant transformation methods are well known to those of skill in the art and are carried out using standard techniques or modifications thereof.

Glyphosate Spray Tests

In one embodiment a greenhouse or field evaluation for glyphosate tolerance is conducted. The term "glyphosate" is used herein to refer collectively to the parent herbicide N-phosphonomethylglycine (otherwise known as glyphosate acid), to a salt or ester thereof, or to a compound which is converted to N-phosphonomethylglycine in plant tissues or which otherwise provides N-phosphonomethylglycine in ionic form (otherwise known as glyphosate ion). Illustratively, water-soluble glyphosate salts useful herein are disclosed in U.S. Pat. No. 3,799,758 and No. 4,405,531 to Franz, the disclosure of which is incorporated herein by reference. Glyphosate salts that can be used according to the present invention include but are not restricted to alkali metal, for example sodium and potassium, salts; ammonium salt; $C_{1-16}$ alkylammonium, for example dimethylammonium and isopropylammonium, salts; $C_{1-16}$ alkanolammonium, for example monoethanolammonium, salt; $C_{1-16}$ alkylsulfonium, for example trimethylsulfonium, salts; mixtures thereof and the like. The glyphosate acid molecule has three acid sites having different pKa values; accordingly mono-, di- and tribasic salts, or any mixture thereof, or salts of any intermediate level of neutralization, can be used.

Glyphosate salts are commercially significant in part because they are water-soluble. Many ammonium, alkylammonium, alkanolammonium, alkylsulfonium and alkali metal salts are highly water-soluble, allowing for formulation as highly concentrated aqueous solutions which can be diluted in water at the point of use.

Such concentrated aqueous solutions can contain about 50 to about 500 grams per liter of glyphosate, expressed as acid equivalent (g a.e./l). Higher glyphosate concentrations, for example about 300 to about 500 g a.e./l, are preferred.

Glyphosate salts are alternatively formulated as water-soluble or water-dispersible compositions, in the form for example of powders, granules, pellets or tablets. Such compositions are often known as dry formulations, although the term "dry" should not be understood in this context to imply the complete absence of water. Typically, dry formulations contain less than about 5% by weight of water, for example about 0.5% to about 2% by weight of water. Such formulations are intended for dissolution or dispersion in water at the point of use.

Contemplated dry glyphosate formulations can contain about 5% to about 80% by weight of glyphosate, expressed as acid equivalent (% a.e.). Higher glyphosate concentrations within the above range, for example about 50% to about 80% a.e., are preferred. Especially useful salts of glyphosate for making dry formulations are sodium and ammonium salts.

Plant treatment compositions and liquid and dry concentrate compositions of the invention can optionally contain one or more desired excipient ingredients. Especially useful excipient ingredients for glyphosate compositions are surfactants, which assist in retention of aqueous spray solutions on the relatively hydrophobic surfaces of plant leaves, as well as helping the glyphosate to penetrate the waxy outer layer (cuticle) of the leaf and thereby contact living tissues within the leaf. Surfactants can perform other useful functions as well.

There is no restriction in the type or chemical class of surfactant that can be used in glyphosate compositions of the invention. Nonionic, anionic, cationic and amphoteric types, or combinations of more than one of these types, are all useful in particular situations. However, it is generally preferred that at least one of the surfactants, if any, present should be other than anionic, i.e., at least one of the surfactants should be nonionic, cationic or amphoteric.

Many surfactants useful herein have a chemical structure that comprises one or more moieties each consisting of a single $C_{2-4}$ alkylene oxide unit or a polymerized or copolymerized chain of $C_{2-4}$ alkylene oxide units. Such surfactants are referred to as polyoxyalkylene surfactants and include nonionic, anionic, cationic and amphoteric types. Polyoxyalkylene surfactants useful in presently contemplated compositions contain about 2 to about 100 $C_{2-4}$ alkylene oxide units. In preferred polyoxyalkylene surfactants the alkylene oxide units form one or more chains of either ethylene oxide or copolymerized ethylene oxide and propylene oxide, each chain of alkylene oxide units having a terminal hydrido group or a $C_{1-4}$ alkyl or $C_{1-4}$ alkanoyl end-cap.

Hydrophobic moieties of surfactants useful in compositions of the invention can be essentially hydrocarbon based, in which case the hydrophobic moieties are typically $C_{8-24}$, preferably $C_{12-18}$, alkyl, alkenyl, alkylaryl, alkanoyl or alkenoyl chains. These chains can be linear or branched. Alternatively, the hydrophobic moieties can contain silicon atoms, for example in the form of siloxane groups such as heptamethyltrisiloxane groups, or fluorine atoms, for example as partially-fluorinated alkyl or perfluoroalkyl chains.

Among nonionic surfactants, especially preferred classes include polyoxyethylene alkyl, alkenyl or alkylaryl ethers, such as ethoxylated primary or secondary alcohols or alkylphenols, polyoxyethylene alkyl or alkenyl esters, such as ethoxylated fatty acids, polyoxyethylene sorbitan alkyl esters, glyceryl alkyl esters, sucrose esters, alkyl polyglycosides, and the like. Representative specific examples of such nonionic surfactants include polyoxyethylene (9) nonylphenol, Neodol™ 25-7 of Shell (a polyoxyethylene (7) $C_{12-15}$ linear primary alcohol), Tergitol™ 15-S-9 of Union Carbide (a polyoxyethylene (9) $C_{12-15}$ secondary alcohol), Tween™ 20 of ICI (a polyoxyethylene (20) sorbitan monolaurate) and Agrimul™ PG-2069 of Henkel (a $C_{9-11}$ alkyl polyglucoside).

Among cationic surfactants, especially preferred classes include polyoxyethylene tertiary alkylamines or alkenylamines, such as ethoxylated fatty amines, quaternary ammonium surfactants, polyoxyethylene alkyletheramines, and the like. Representative specific examples of such cationic surfactants include polyoxyethylene (5) cocoamine, polyoxyethylene (15) tallowamine, distearyldimethylammonium chloride, cetyltrimethylammonium bromide, methyl bis(2-hydroxyethyl)cocoammonium chloride, N-dodecylpyridine chloride and polyoxypropylene (8) ethoxytrimethylammonium chloride. Particularly preferred polyoxyethylene alkyletheramines are those disclosed in PCT Publication No. WO 96/32839. Many cationic quaternary ammonium surfactants of diverse structures are known in the art to be useful in combination with glyphosate and can be used in compositions contemplated herein; such quaternary ammonium surfactants have the formula

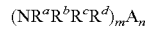

$$(NR^aR^bR^cR^d)_mA_n$$

where A is a suitable anion such as chloride, bromide, iodide, acetate, sulfate or phosphate, m and n are integers such that the positive electrical charges on cations $(NR^aR^bR^cR^d)$ balance the negative electrical charges on anions A, and options for $R^a$, $R^c$ and $R^d$ include, without limitation:

(i) $R^a$ is benzyl or $C_{8-24}$, preferably $C_{12-18}$, alkyl or alkenyl, and $R^b$, $R^c$ and $R^d$ are independently $C_{1-4}$ alkyl, preferably methyl;

(ii) $R^a$ and $R^b$ are independently $C_{8-24}$, preferably $C_{12-18}$, alkyl or alkenyl, and $R^c$ and $R^d$ are independently $C_{1-4}$ alkyl, preferably methyl;

(iii) $R^a$ is $C_{8-24}$, preferably $C_{12-18}$, alkyl or alkenyl, $R^b$ is a polyoxyalkylene chain having about 2 to about 100 $C_{2-4}$ alkylene oxide units, preferably ethylene oxide units, and $R^c$ and $R^d$ are independently $C_{1-4}$ alkyl, preferably methyl;

(iv) $R^a$ is $C_{8-24}$, preferably $C_{12-18}$, alkyl or alkenyl, $R^b$ and $R^c$ are polyoxyalkylene chains having in total about 2 to about 100 $C_{2-4}$ alkylene oxide units, preferably ethylene oxide units, and $R^d$ is $C_{1-4}$ alkyl, preferably methyl; or (v) $R^a$ is a polyoxyalkylene chain having about 2 to about 100 $C_{2-4}$ alkylene oxide units in which $C_{3-4}$ alkylene oxide units, preferably propylene oxide units, predominate and $R^b$, $R^c$ and $R^d$ are independently $C_{1-4}$ alkyl, preferably methyl or ethyl. Particularly preferred quaternary ammonium surfactants of this type are those disclosed in U.S. Pat. No. 5,464,807 to Claude et al.

In one embodiment, the anion A associated with such a quaternary ammonium surfactant can be a glyphosate anion.

Among amphoteric surfactants, including as is customary in the art surfactants more correctly described as zwitterionic, especially preferred classes include polyoxyethylene alkylamine oxides, alkylbetaines, alkyl-substituted amino acids and the like. Representative examples of such amphoteric surfactants include dodecyldimethylamine oxide, polyoxyethylene (2) cocoamine oxide and stearyldimethylbetaine.

Standard reference sources from which one of skill in the art can select suitable surfactants, without limitation to the above mentioned classes, include *Handbook of Industrial Surfactants*, Second Edition (1997) published by Gower, *McCutcheon's Emulsifiers and Detergents*, North American and International Editions (1997) published by MC Publishing Company, and *International Cosmetic Ingredient Dictionary*, Sixth Edition (1995) Volumes 1 and 2, published by the Cosmetic, Toiletry and Fragrance Association.

Other optional components of compositions of the invention include agents to modify color, viscosity, gelling properties, freezing point, hygroscopicity, caking behavior, dissolution rate, dispersibility, or other formulation characteristics.

Examples of commercial formulations of glyphosate include, without restriction, those sold by Monsanto Company as ROUNDUP®, ROUNDUP® ULTRA, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt.

The selection of application rates for a glyphosate formulation that are biologically effective is within the skill of the ordinary agricultural technician. One of skill in the art will likewise recognize that individual plant conditions, weather conditions and growing conditions can affect the results achieved in practicing the process of the present invention. Over two decades of glyphosate use and published studies relating to such use have provided abundant information from which a weed control practitioner can select glyphosate application rates that are herbicidally effective on particular species at particular growth stages in particular environmental conditions.

A process of the present invention is applicable to any and all plant species on which glyphosate is biologically effective as a herbicide or plant growth regulator. This encompasses a very wide variety of plant species worldwide. Likewise, compositions of the invention can be applied to any and all plant species on which glyphosate is biologically effective.

In one embodiment, a glyphosate-containing herbicide is applied to the plant comprising the DNA constructs of the present invention, and the plants are evaluated for tolerance to the glyphosate herbicide. Any formulation of glyphosate can be used for testing plants comprising the DNA constructs of the present invention. For example, a glyphosate composition such as Roundup Ultra™ can be used. The testing parameters for an evaluation of the glyphosate tolerance of the plant will vary depending on a number of factors. Factors would include, but are not limited to the type of glyphosate formulation, the concentration and amount of glyphosate used in the formulation, the type of plant, the plant developmental stage during the time of the application, environmental conditions, the application method, and the number of times a particular formulation is applied. For example, plants can be tested in a greenhouse environment using a spray application method. The testing range using Roundup Ultra™ can include, but is not limited to 8 oz/acre to 256 oz/acre. The preferred commercially effective range can be from 16 oz/acre to 64 oz/acre of Roundup Ultra™, depending on the crop and stage of plant development. A crop can be sprayed with at least one application of a glyphosate formulation. For testing in cotton an application of 32 oz/acre at the 3-leaf stage may be followed by additional applications at later stages in development. For wheat an application of 32 oz/acre of Roundup Ultra™ at the 3-5 leaf stage can be used and may be followed with a pre- or post-harvest application, depending on the type of wheat to be tested. The test parameters can be optimized for each crop in order to find the particular plant comprising the constructs of the present invention that confers the desired commercially effective glyphosate tolerance level.

The following examples are included to demonstrate preferred embodiments of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings is to be interpreted as illustrative and not in a limiting sense.

EXAMPLES

Example 1

The plasmid constructs used are either pUC cloning constructs or double border plant transformation constructs containing an *E. coli* origin of replication such as ori322, a broad host range origin of replication such as oriV or oriRi, and a coding region for a selectable marker such as Spc/Str that encodes for Tn7 aminoglycoside adenyltransferase (aadA) confers resistance to spectinomycin or streptomycin, or a gentamicin (Gm, Gent) selectable marker. For plant transformation, the host bacterial strain was *Agrobacterium tumefaciens* ABI or LBA4404.

The genetic elements are described as follows: P-e35S is the 35S RNA from CAMV containing a duplication of the −90-300 region as described in U.S. Pat. No. 5,424,200 herein incorporated by reference in its entirety; P-FMV is the 34S promoter from Figwort Mosaic Virus as described in U.S. Pat. No. 5,378,619 herein incorporated by reference in its entirety; P-eFMV is a derivative of the FMV promoter containing a duplicated FMV promoter; CTP2 is the transit peptide region of *Arabidopsis* EPSP synthase as described in U.S. Pat. No.

5,633,435; aroA:CP4syn (aroA:CP4) is the coding region for CP4 EPSP (synthetic sequence) as described in U.S. Pat. No. 5,633,435 or further modified for expression in plants based on codon usage of particular plant species; E9 3' is the 3' end of an isolate of the pea RbcS gene that functions as a polyadenylation signal; nos is the 3' end of the nopaline synthase gene that functions as a polyadenylation signal; Hsp70 is the non-translated leader sequence from *Petunia hybrida* as described in U.S. Pat. No. 5,362,865 herein incorporated by reference in its entirety; GUS is the beta-glucuronidase coding sequence from *E. coli* (Jefferson, R. A. Proc. Natl. Acad. Sci. U.S.A., 83: 8447-8451, 1987); the right border (RB) and left borders (LB) are from the Ti plasmid of *Agrobacterium tumefaciens* octopine and nopaline strains. The P-AtAct2 is the promoter from the *Arabidopsis thaliana* actin 2 gene; AtAct2i is the intron in the 5' untranslated region (UTR) of the *Arabidopsis thaliana* actin 2 gene; P-AtAct8 is the promoter from the *Arabidopsis thaliana* actin 8 gene; AtAct2i is the intron in the 5' UTR of the *Arabidopsis thaliana* actin 8 gene; P-AtAct11 is the promoter from the *Arabidopsis thaliana* actin 11 gene; AtAct11i is the intron in the 5' UTR of the *Arabidopsis thaliana* actin 11 gene; P-AtAct1a is the promoter from the *Arabidopsis thaliana* actin 1a gene, L-AtAct1a is the untranslated leader and I-AtAct1a is the intron from the genomic DNA of the actin 1a gene; P-AtAct1b is the promoter from the *Arabidopsis thaliana* actin 1b gene, L-AtAct1b is the untranslated leader and I-AtAct1b is the intron from the genomic DNA of the actin 1b gene; P-AtAct3 is the promoter from the *Arabidopsis thaliana* actin 3 gene, L-AtAct3 is the untranslated leader and I-AtAct3 is the intron from the genomic DNA of the actin 3 gene; P-AtAct7 is the promoter from the *Arabidopsis thaliana* actin 7 gene, L-AtAct7 is the untranslated leader and I-AtAct7 is the intron from the genomic DNA of the actin 7 gene; P-AtAct12 is the promoter from the *Arabidopsis thaliana* actin 12 gene, L-AtAct12 is the untranslated leader and I-AtAct12 is the intron from the genomic DNA of the actin 12 gene; P-AtEF1α (P-AtEF1 or EF1α) is the promoter from the *Arabidopsis thaliana* elongation factor gene 1α, AtEF1α-i (AtEF1-i) is the intron in the 5' UTR of the *Arabidopsis thaliana* elongation factor gene 1α.

Figure 2:
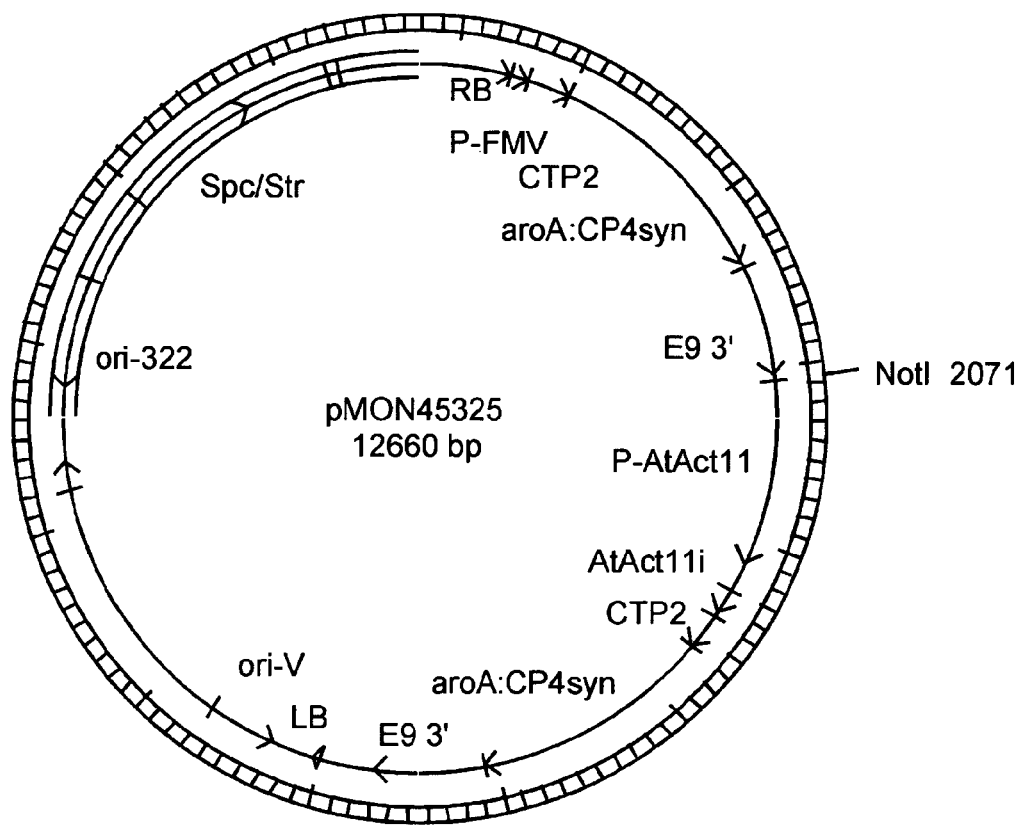
FIG. 2 is a plasmid map of pMON45325
Figure 3:
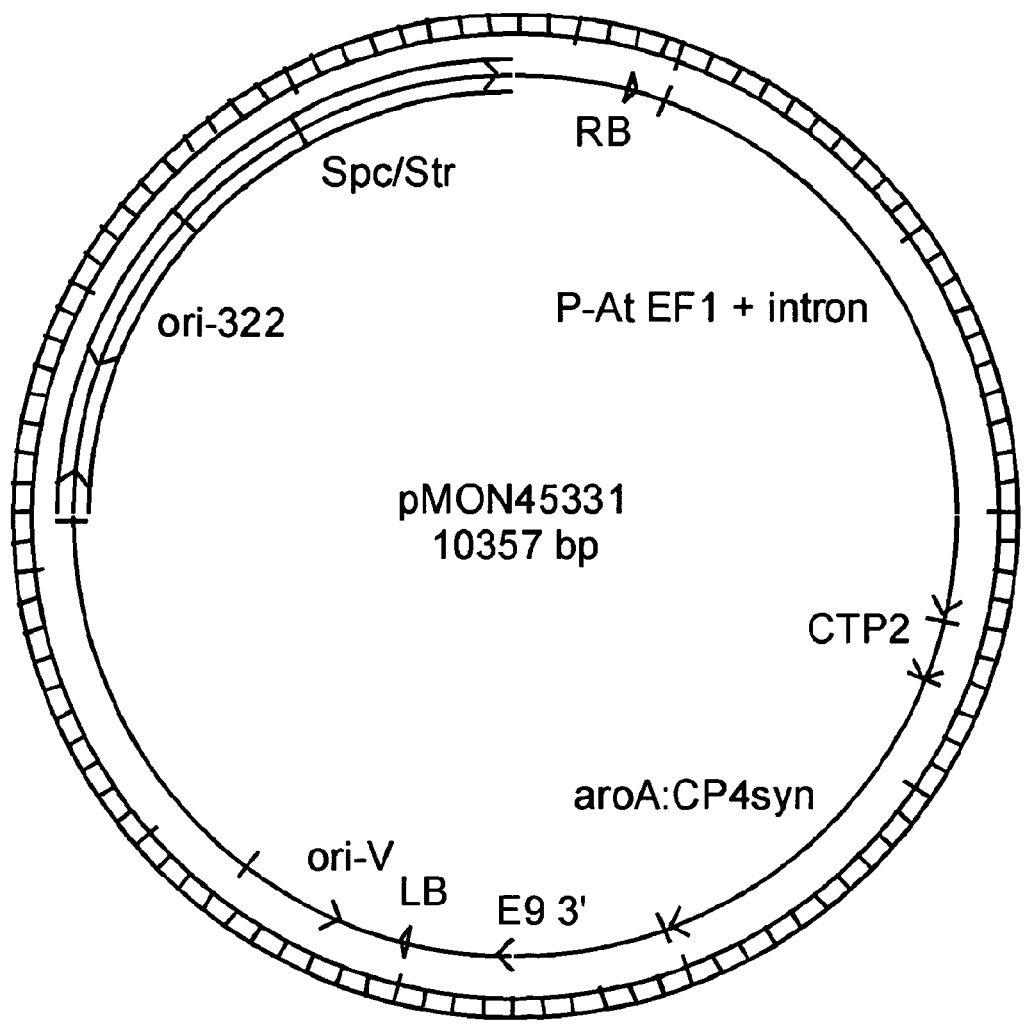
FIG. 3 is a plasmid map of pMON45331
Figure 4:
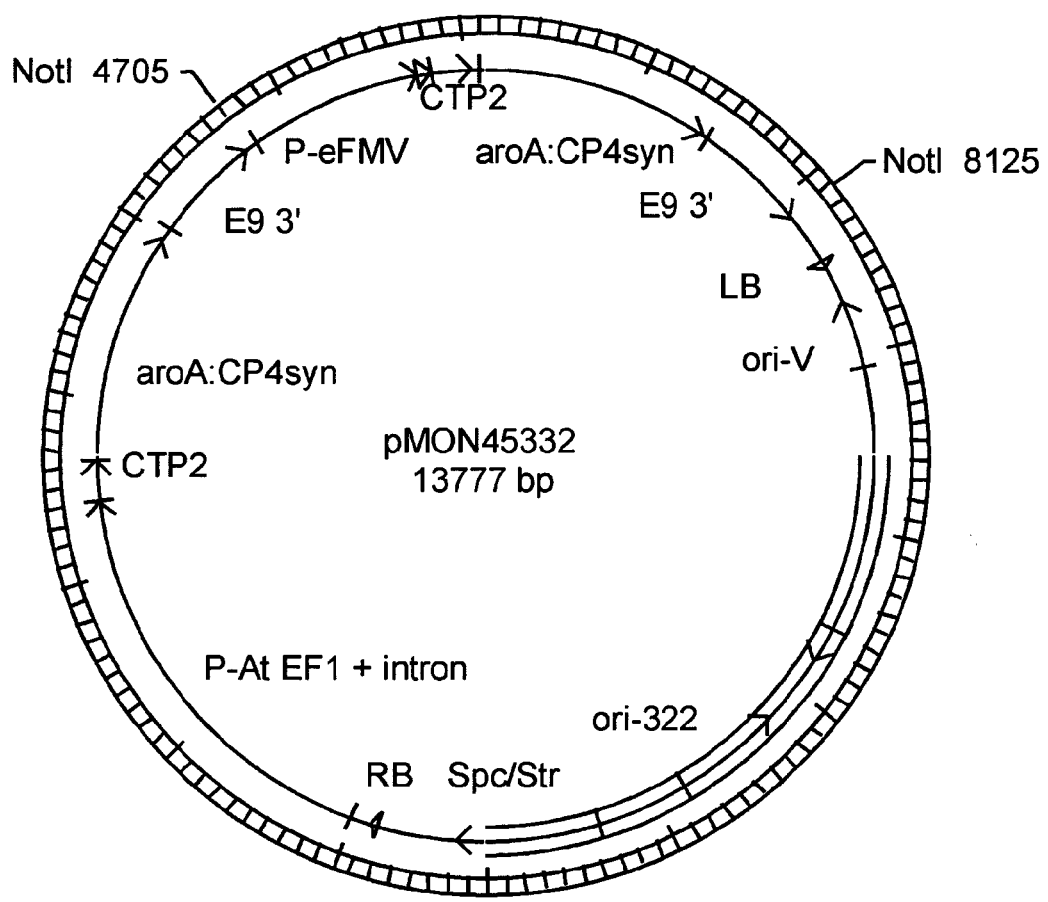
FIG. 4 is a plasmid map of pMON45332
Figure 5:
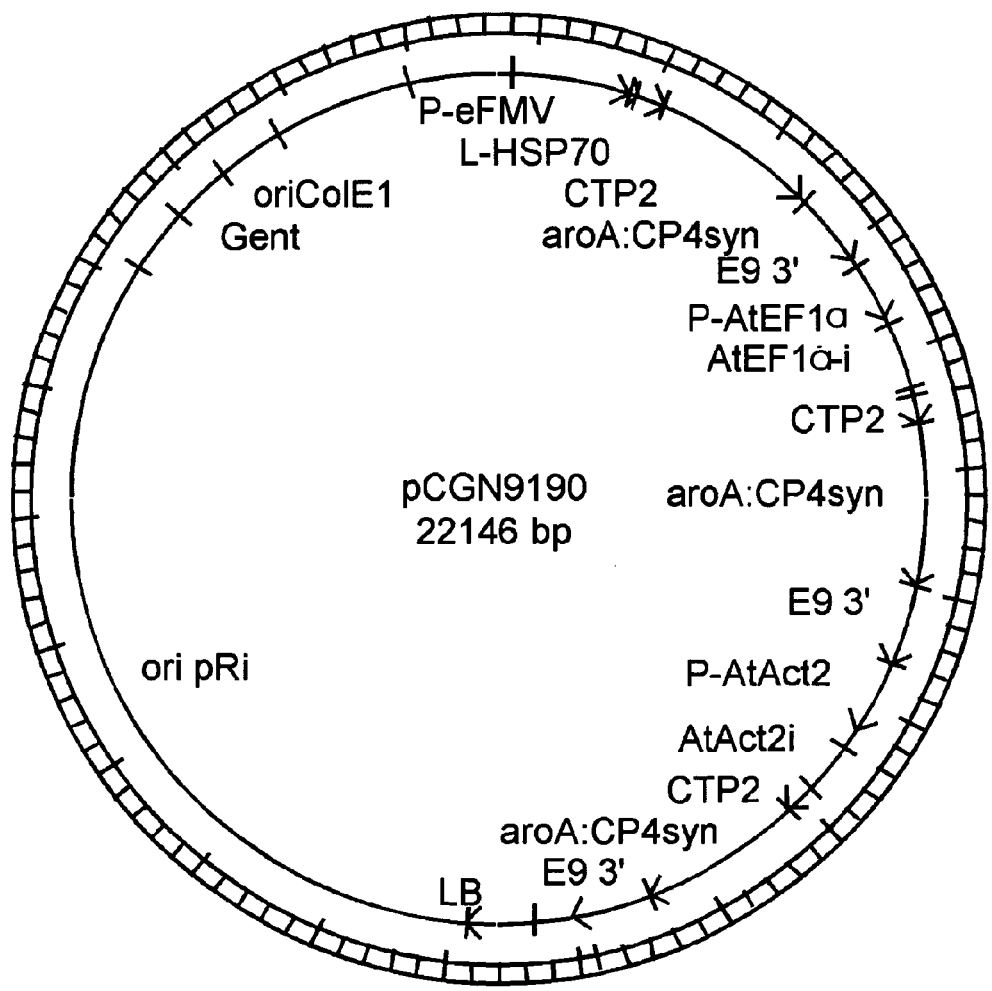
FIG. 5 is a plasmid map of pCGN9190
Figure 6:
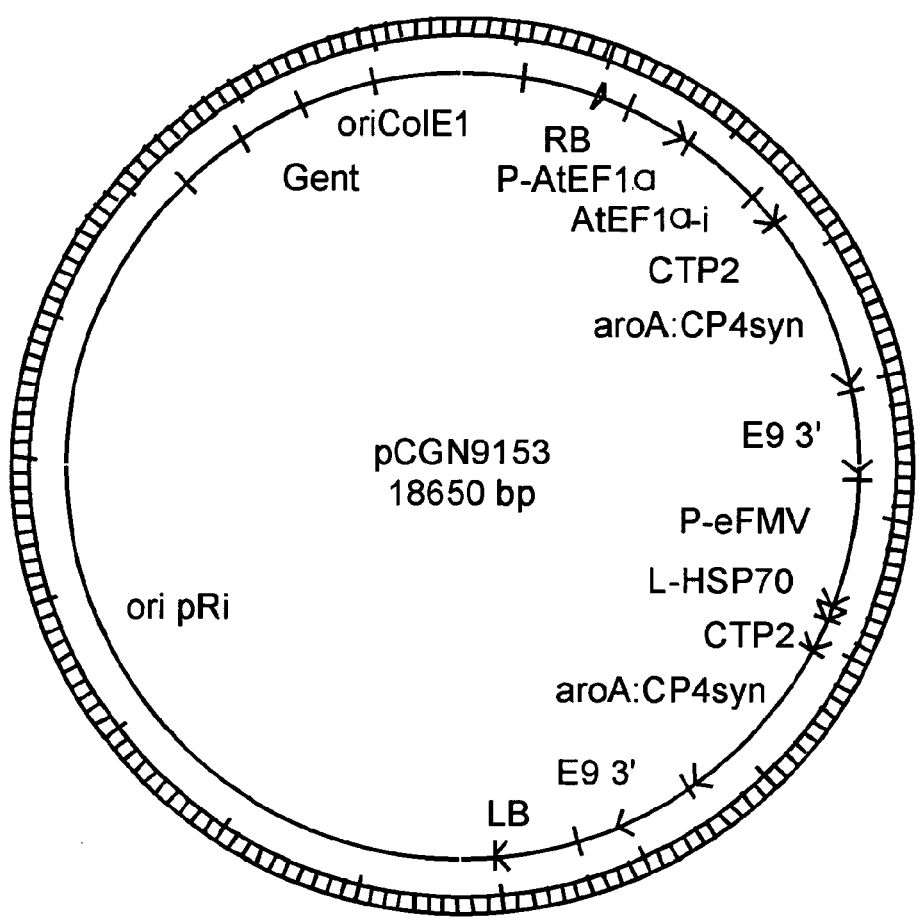
FIG. 6 is a plasmid map of pCGN9153
Figure 7:
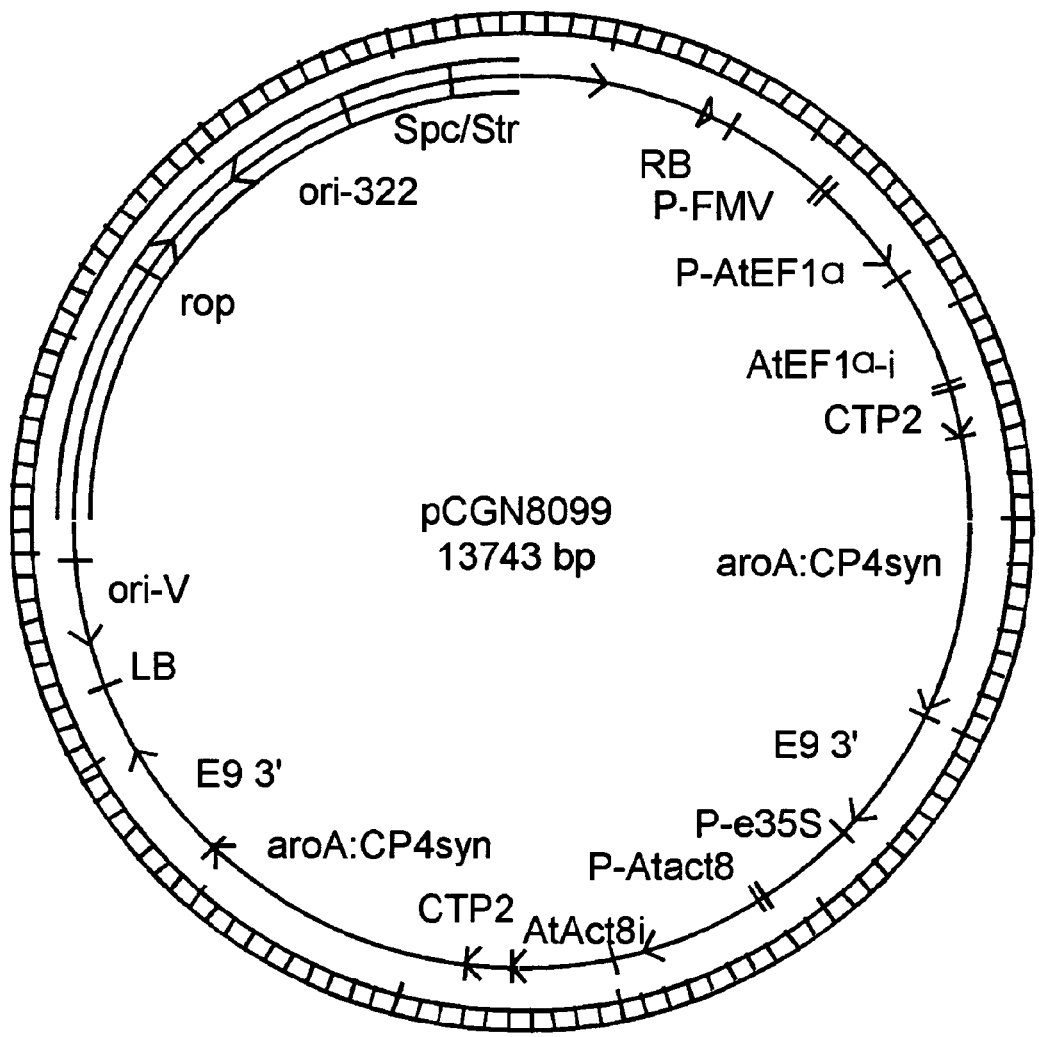
FIG. 7 is a plasmid map of pCGN8099
Figure 8:
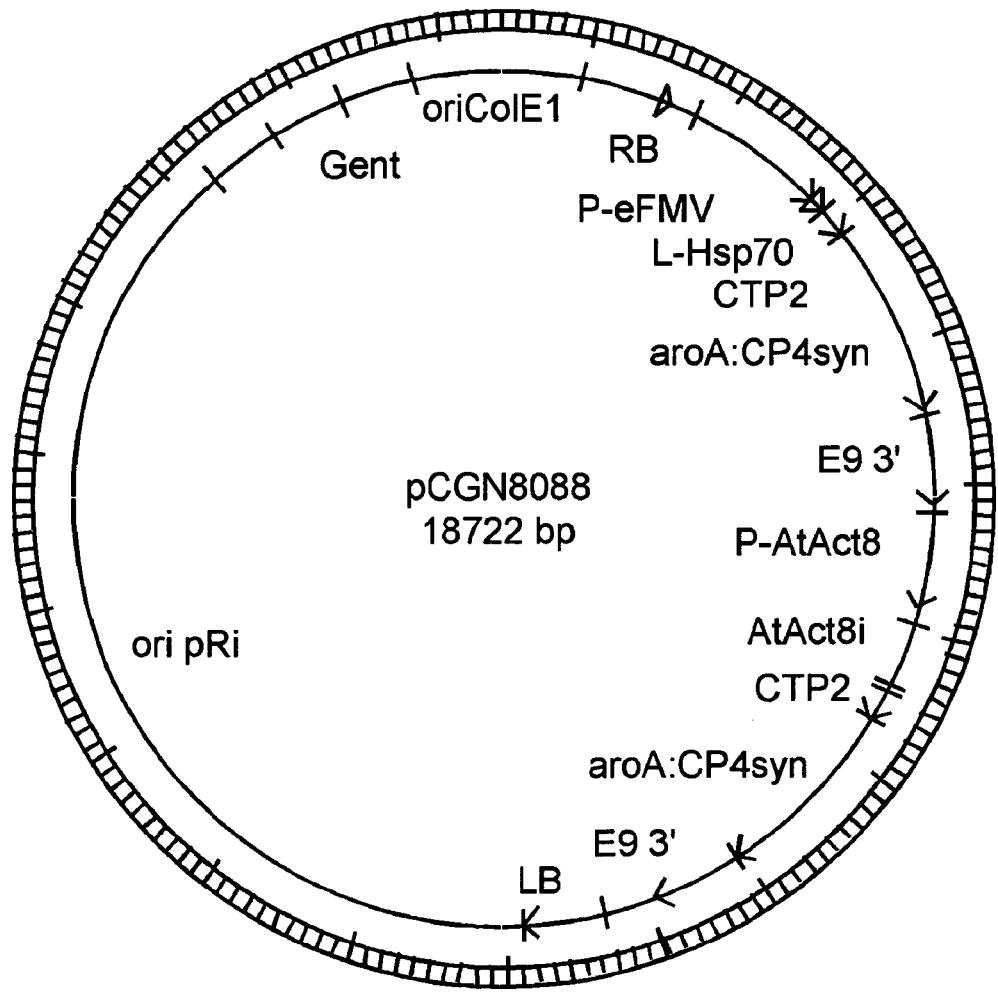
FIG. 8 is a plasmid map of pCGN8088
Figure 9:
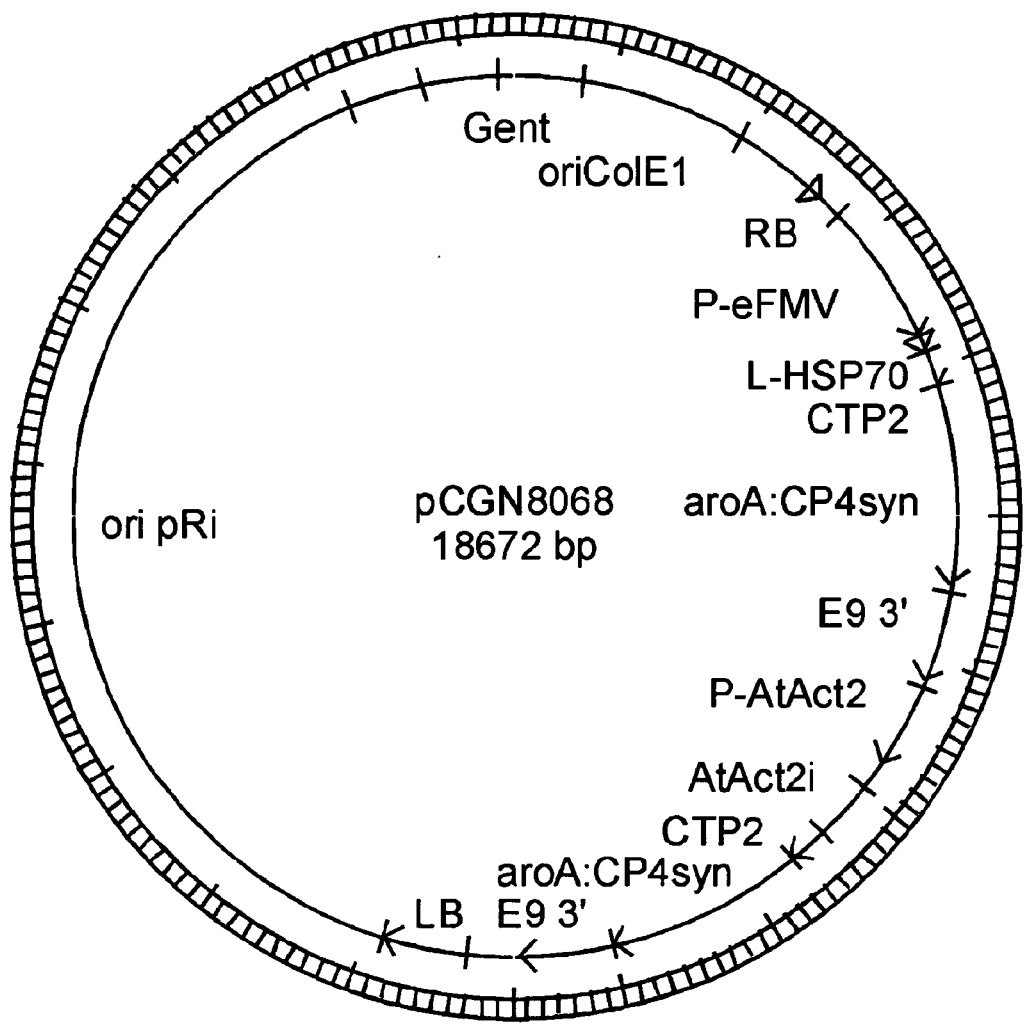
FIG. 9 is a plasmid map of pCGN8068
Figure 10:
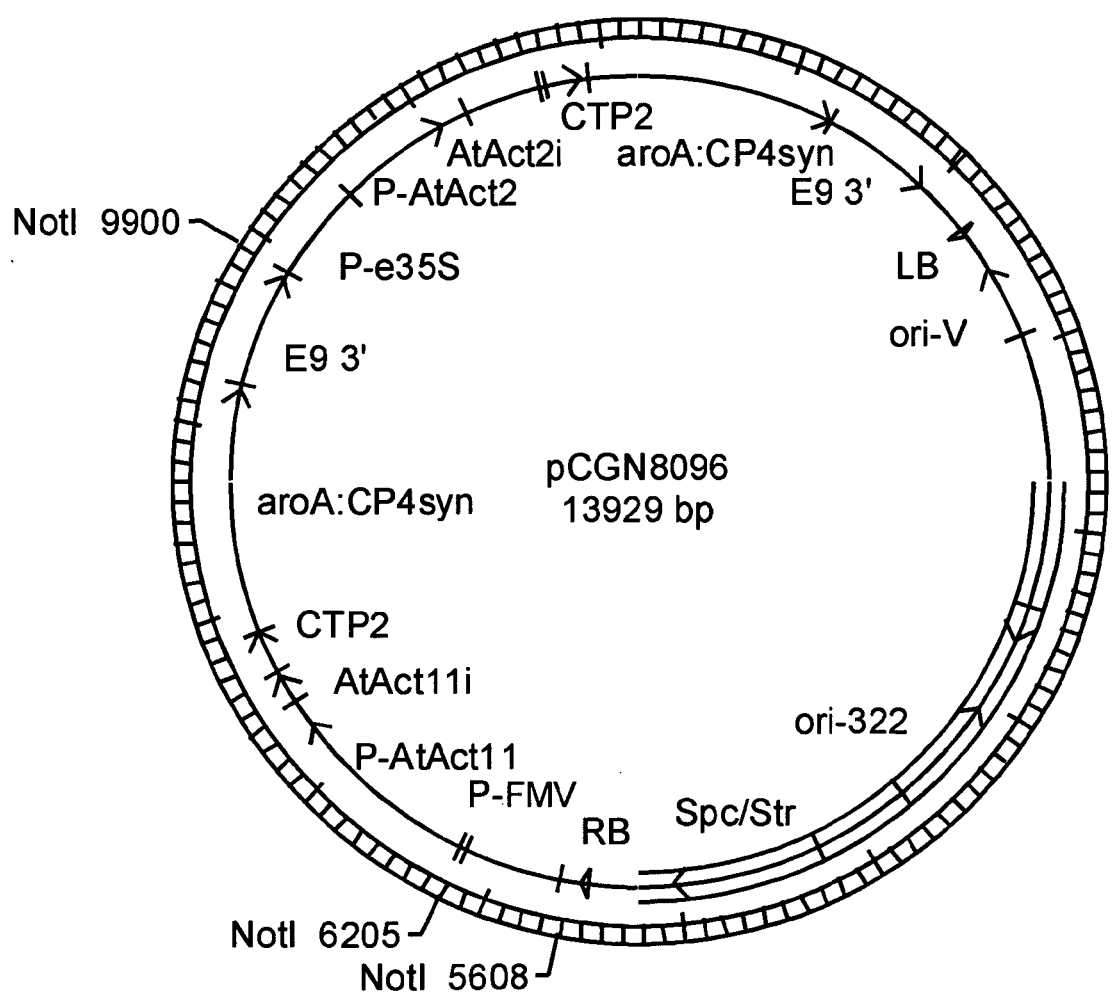
FIG. 10 is a plasmid map of pCGN8096
Figure 11:
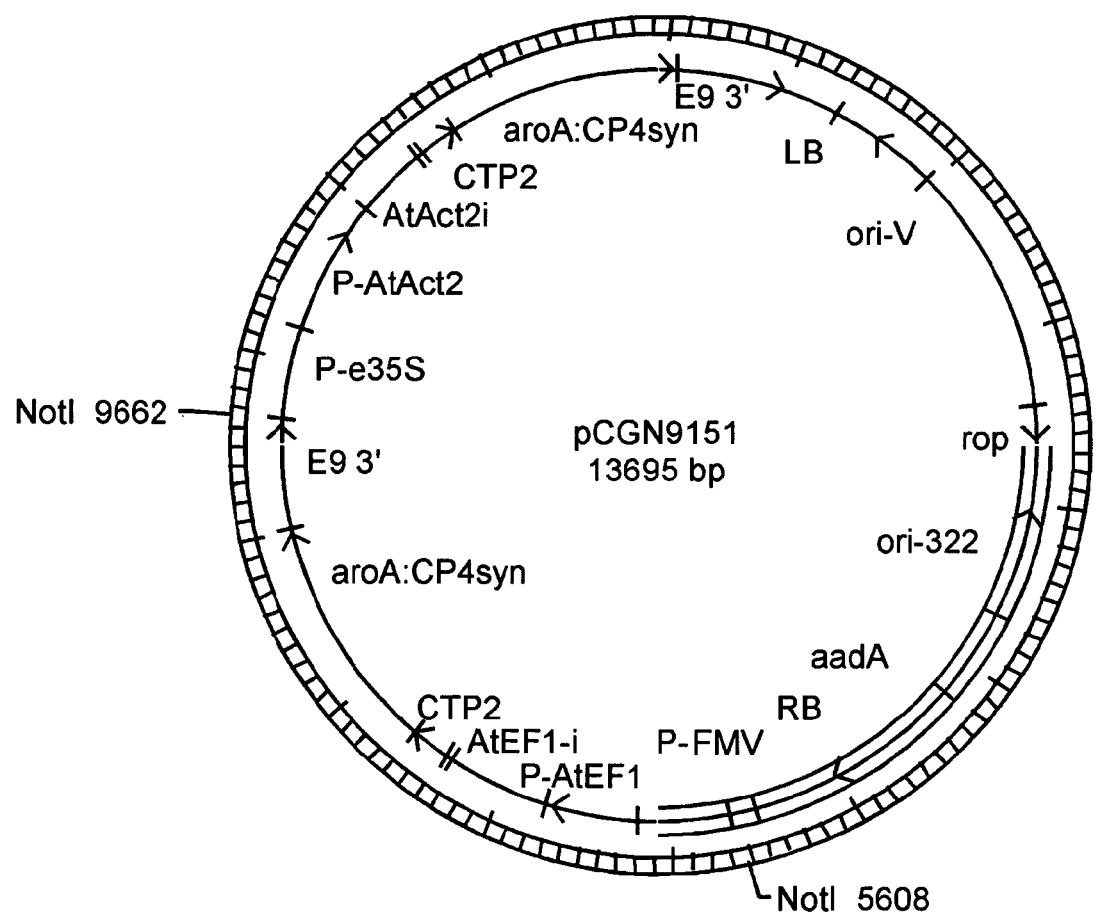
FIG. 11 is a plasmid map of pCGN9151
Figure 12:
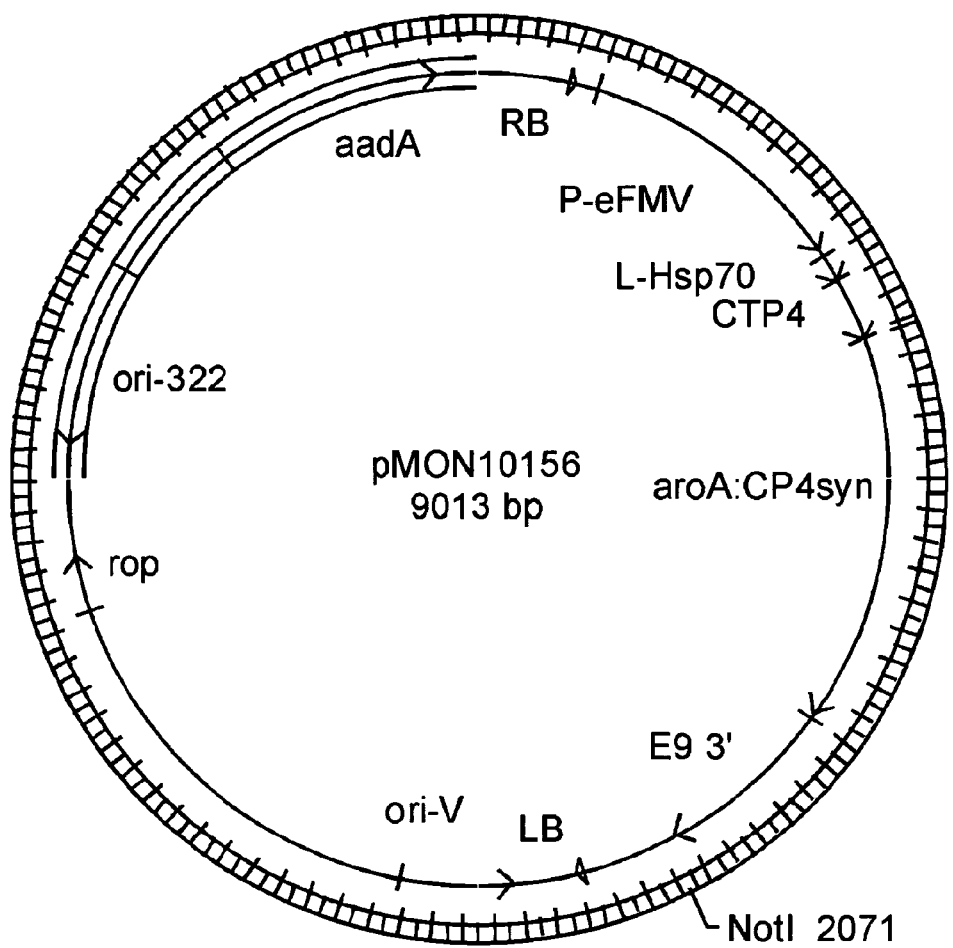
FIG. 12 is a plasmid map of pMON10156
Figure 13:
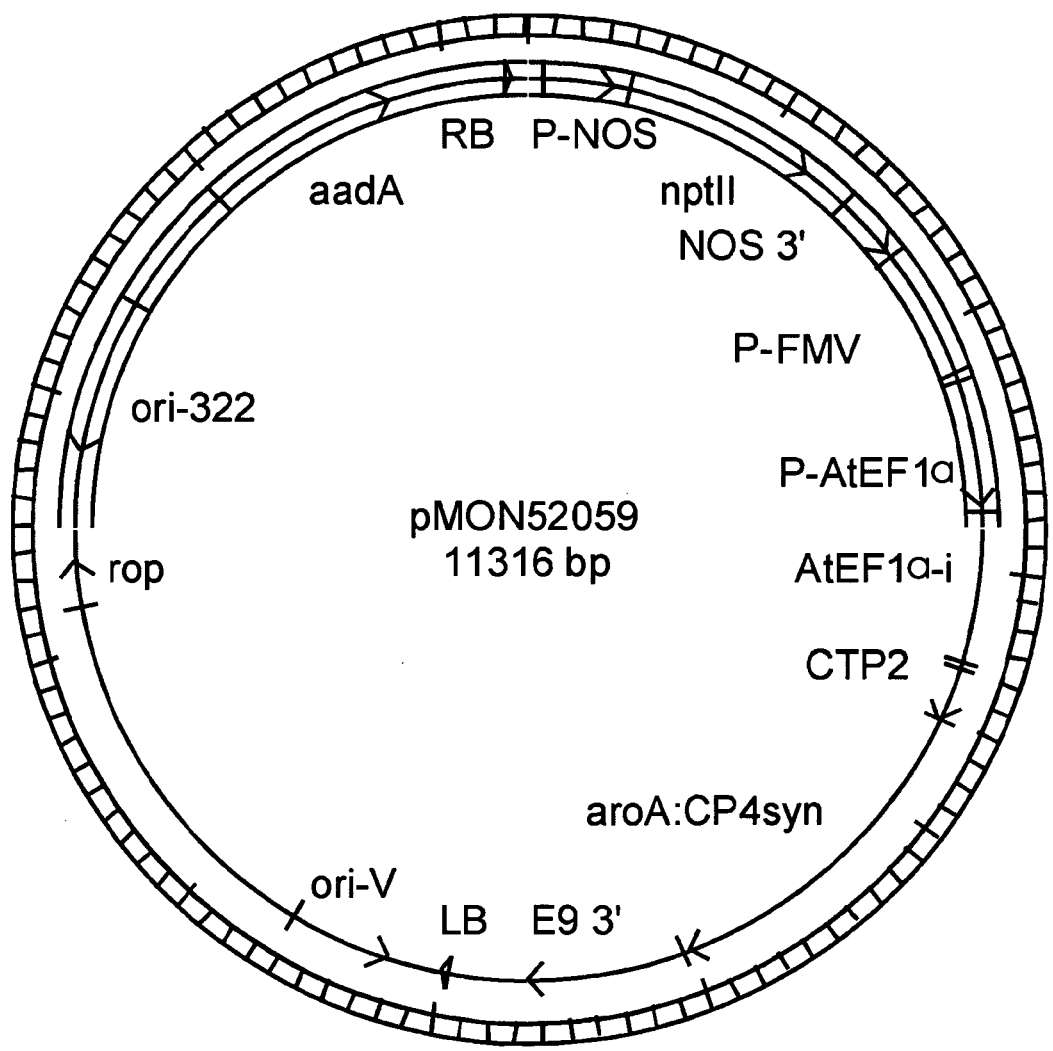
FIG. 13 is a plasmid map of pMON52059
Figure 14:
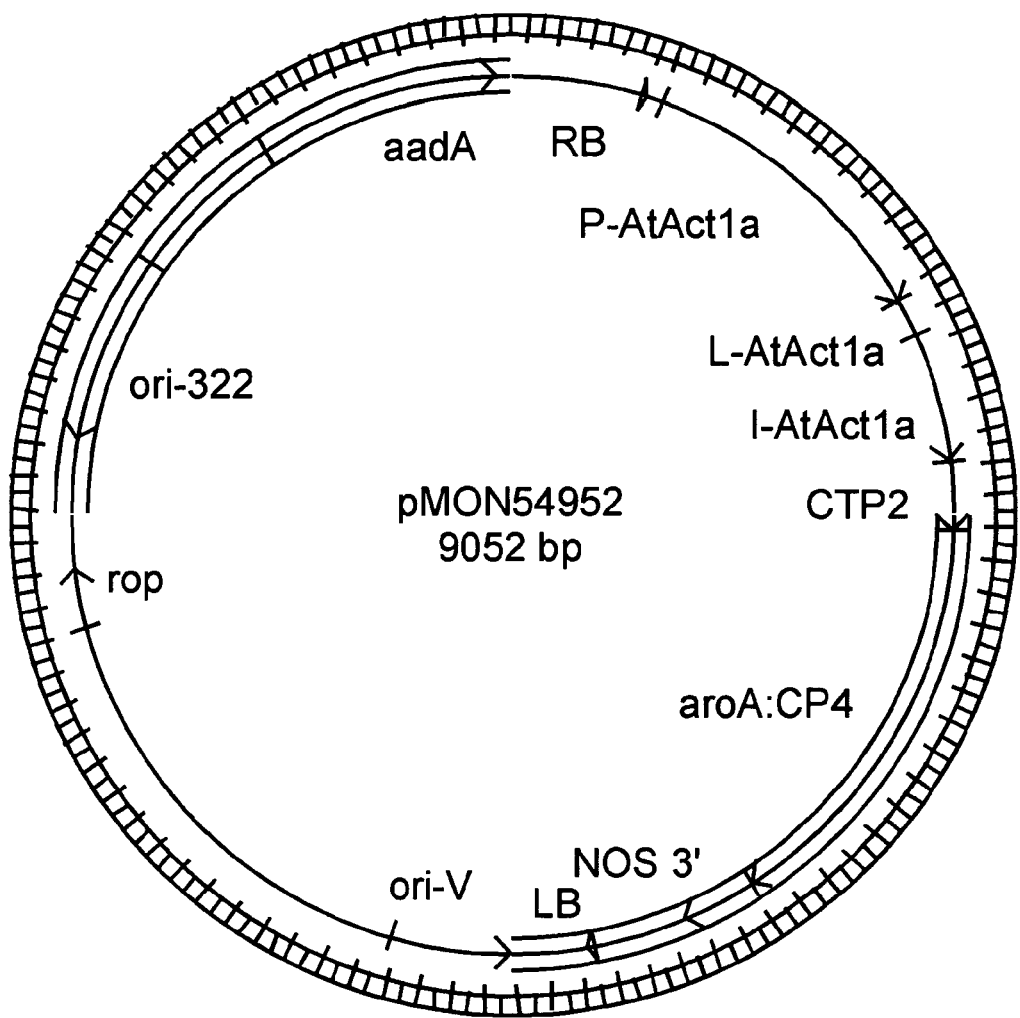
FIG. 14 is a plasmid map of pMON54952
Figure 15:
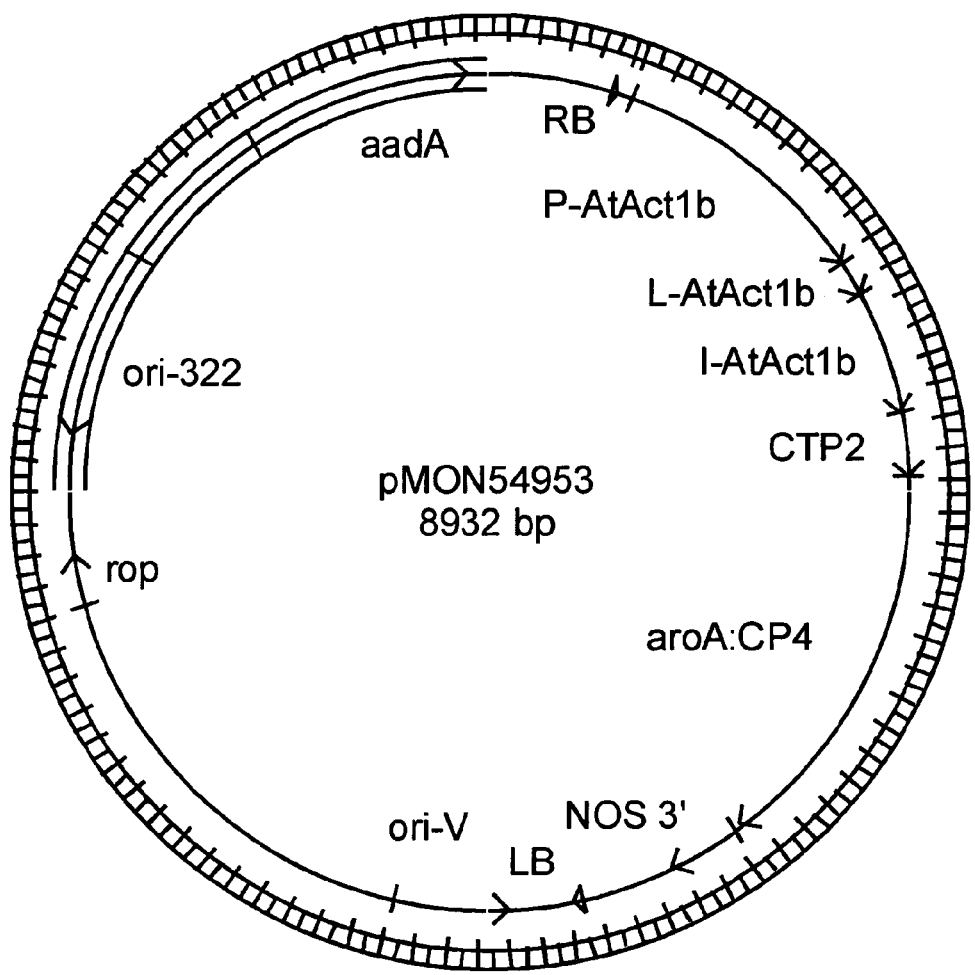
FIG. 15 is a plasmid map of pMON54953
Figure 16:
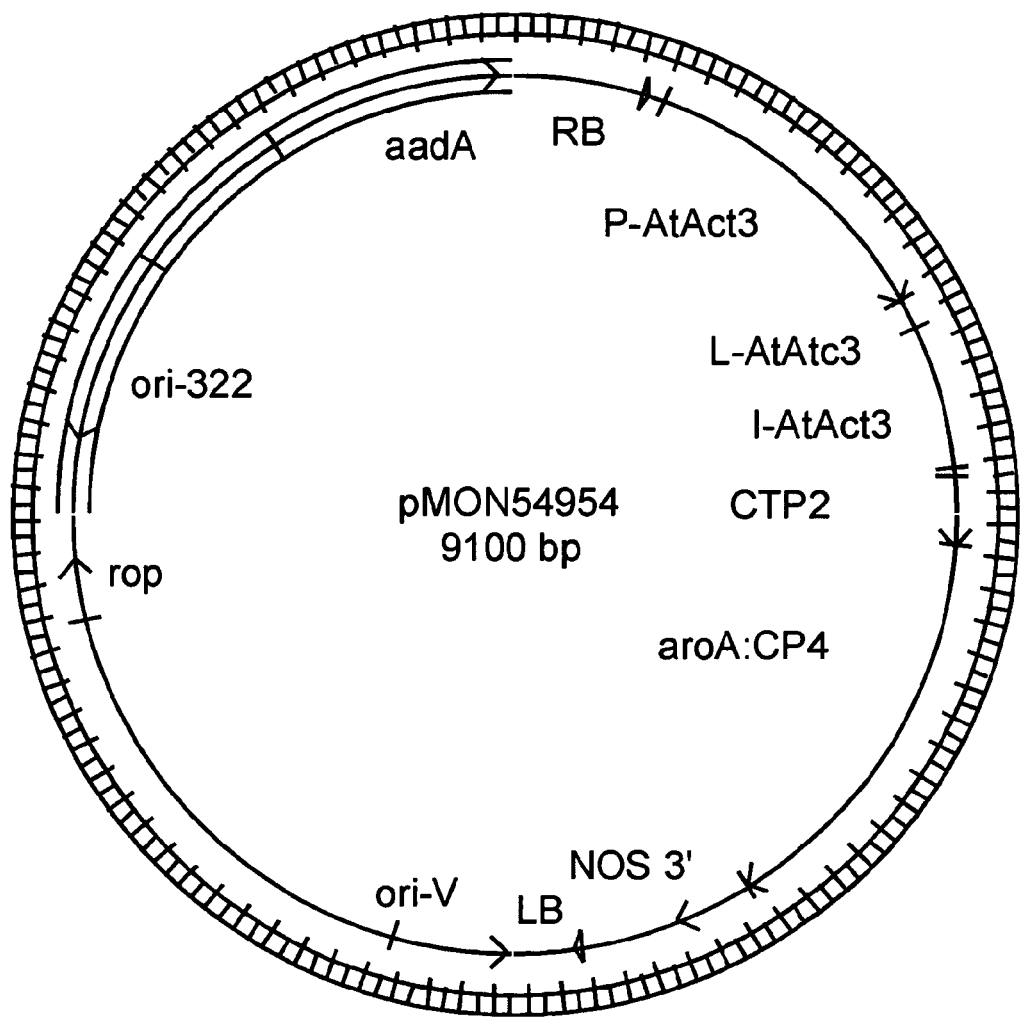
FIG. 16 is a plasmid map of pMON54954
Figure 17:
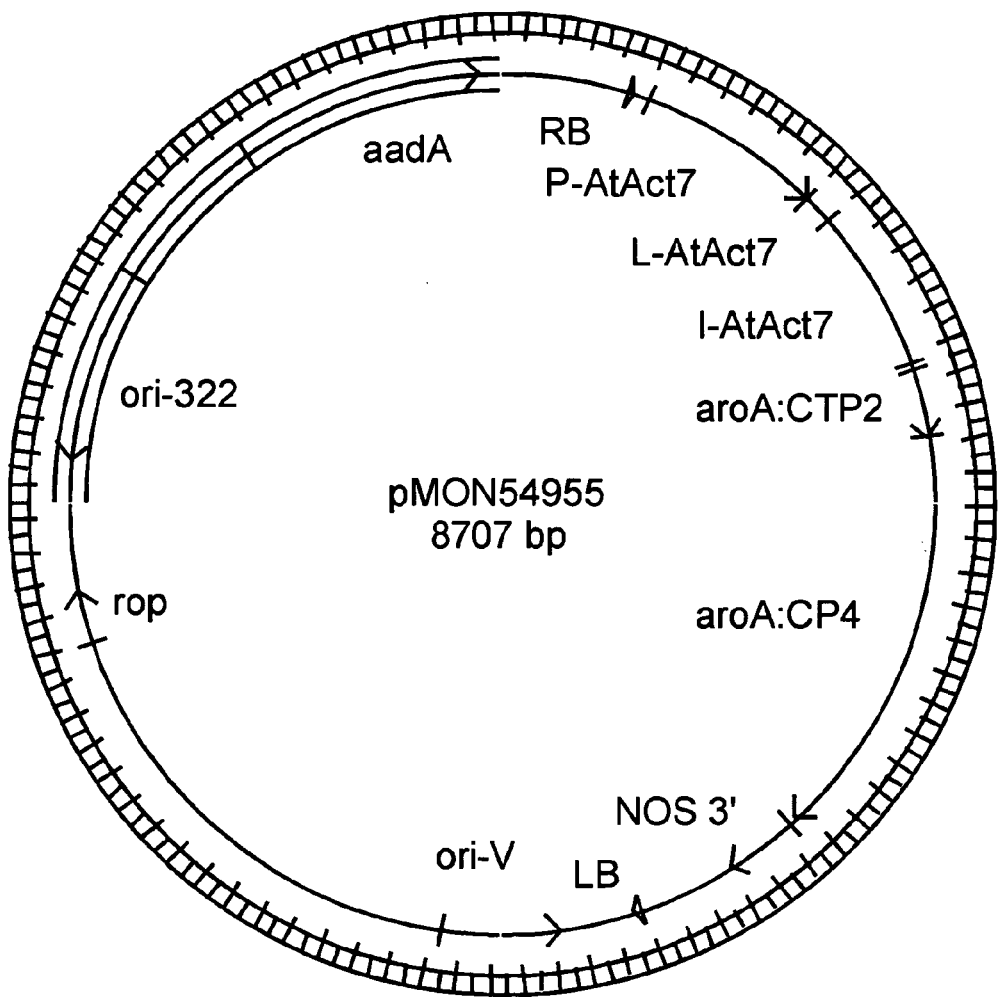
FIG. 17 is a plasmid map of pMON54955
Figure 18:
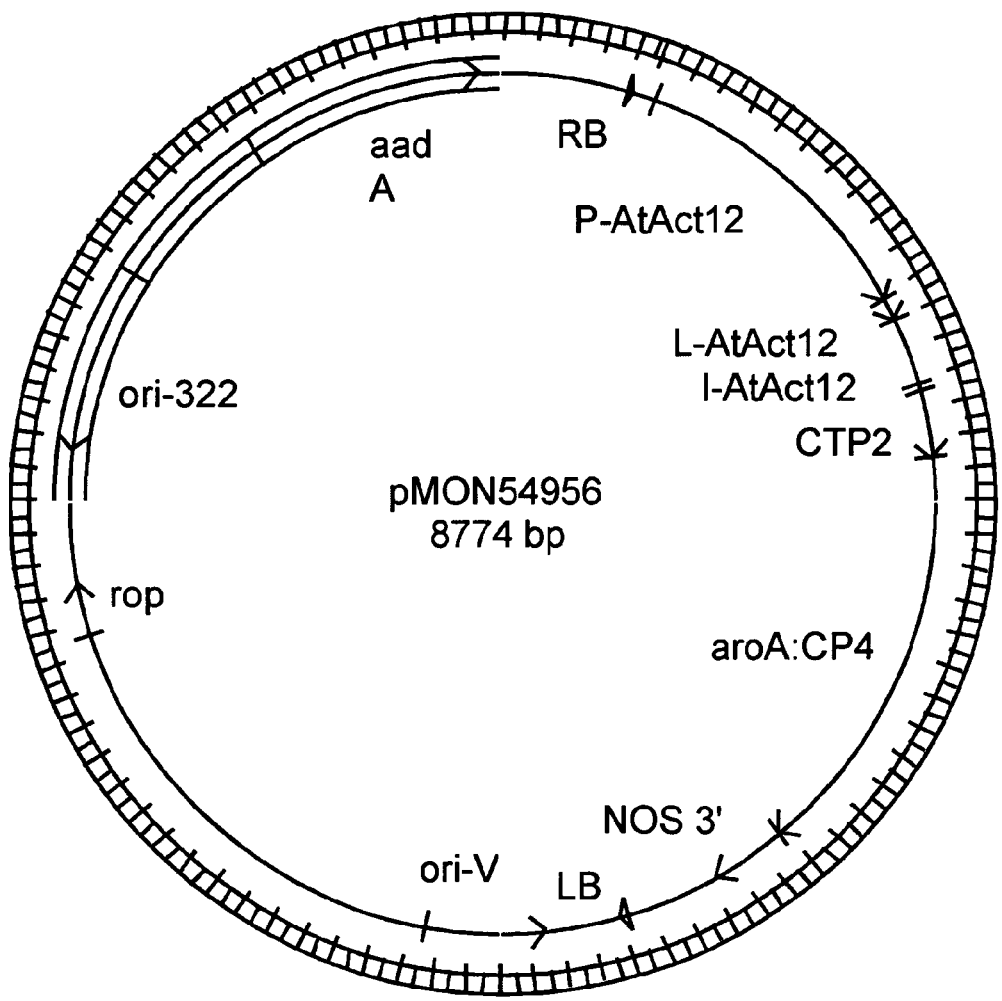
FIG. 18 is a plasmid map of pMON54956

FIGS. 1-18 provide examples of plant transformation constructs that contain one to three plant expression cassettes. Multiple combinations of plant expression cassettes comprising the promoter and genetic elements of the present invention can be constructed and tested in crops plants by those skilled in the art of plant molecular biology without undue experimentation. The constructs illustrated in the Figures are not to be construed as the only constructs that can be assembled, but serve only as examples to those skilled in the art. FIG. 1 (pCGN8086) provides an example of a plant transformation construct containing one expression cassette comprising one promoter of the present invention (P-AtAct8) operably linked to a gene of interest (CTP2-aroA:CP4syn). FIG. 2 (pMON45325) provides an example of a plant transformation construct containing two expression cassettes comprising at least one promoter of the present invention (P-AtAct11) operably linked to at least one gene of interest (CTP2-aroA:CP4syn). FIG. 3 (pMON45331) provides an example of a plant transformation construct containing one expression cassette comprising one promoter of the present invention (P-AtEF1 plus intron) operably linked to at least one gene of interest (CTP2-aroA:CP4syn). FIG. 4 (pMON45332) provides an example of a plant transformation construct containing two expression cassettes comprising at least one promoter of the present invention (P-AtEF1 plus intron) operably linked to at least one gene of interest (CTP2-aroA:CP4syn). FIG. 5 (pMON9190) provides an example of a plant transformation construct containing three expression cassettes wherein at least two promoters of the present invention (P-AtEF1 plus intron, AtEF1a-i; P-AtAct2 plus intron, AtAct2i) are operably linked to at least one gene of interest (CTP2-aroA:CP4syn) and the P-EFMV promoter operably lined to CTP2-aroA:CP4syn. FIG. 6 (pMON9153) plant expression cassettes are identical to those illustrated in FIG. 4 (pMON45332), this plasmid map is illustrated for the purpose of identification of the expression cassettes for data shown on plant phenotype in the data tables shown in the specification. FIG. 7 (pCGN8099) provides an example of a plant transformation construct containing two expression cassettes comprising hybrid promoters of the present invention, P-FMV-AtEF1α and P-e35S-AtAct8, driving transcription of the gene of interest (aroA:CP4syn). FIG. 8 (pCGN8088) provides an example of a plant transformation construct containing two expression cassettes comprising one promoter of the present invention, P-AtAct8 plus intron, AtAct8i, and the P-eFMV promoter driving expression of a gene of interest (aroA:CP4syn). FIG. 9 (pCGN8068) provides an example of a plant transformation construct containing two expression cassettes comprising one promoter of the present invention, P-AtAct2 plus intron, AtAct2i, and the P-eFMV promoter driving expression of a gene of interest (aroA:CP4syn). FIG. 10 (pCGN8096) provides an example of a plant transformation construct containing two expression cassettes comprising hybrid promoters of the present invention, P-FMV/AtAct11 and P-e35S-AtAct2, driving transcription of the gene of interest (aroA:CP4syn). FIG. 11 (pCGN9151) provides an example of a plant transformation construct containing two expression cassettes comprising hybrid promoters of the present invention, P-FMV-AtEF1α and P-e35S-AtAct2, driving transcription of the gene of interest (aroA:CP4syn). FIG. 12 (pMON10156) provides an example of a plant transformation construct containing one expression cassette comprising the P-eFMV promoter driving expression of the aroA:CP4syn gene of interest, this vector is used for comparative purposes with the promoter sequences of the present invention. FIG. 13 (pMON52059) provides an example of a plant transformation construct containing one expression cassette comprising a hybrid promoter (P-FMV-AtEF1α) driving the expression of the gene of interest (aroA:CP4syn). FIG. 14 (pMON54952) provides an example of a plant transformation construct containing one expression cassette comprising one promoter of the present invention (P-AtAct1a plus AtAct1a intron) operably linked to at least one gene of interest (CTP2-aroA:CP4syn). FIG. 15 (pMON54953) provides an example of a plant transformation construct containing one expression cassette comprising one promoter of the present invention (P-AtAct1b plus AtAct1b intron) operably linked to at least one gene of interest (CTP2-aroA:CP4syn). FIG. 16 (pMON54954) provides an example of a plant transformation construct containing one expression cassette comprising one promoter of the present invention (P-AtAct3 plus AtAct3 intron) operably linked to at least one gene of interest (CTP2-aroA:CP4syn). FIG. 17 (pMON54955) provides an example of a plant transformation construct containing one expression cassette comprising one promoter of the present invention (P-AtAct7 plus AtAct7 intron) operably linked to at least one gene of interest (CTP2-aroA:CP4syn). FIG. 18 (pMON54956) provides an example of a plant transformation construct containing one expression cassette comprising one promoter of the present invention (P-AtAct12 plus AtAct12 intron) operably linked to at least one gene of interest (CTP2-aroA:CP4syn).

Example 2

The cloning constructs and GUS constructs are listed in Table 1. The *Arabidopsis* actin 2 promoter and intron (Genbank accession number U41998 as described in An et al., *Plant J.* 10:107-121, 1996) was isolated using *Arabidopsis thaliana* Landsberg erecta DNA as a template (Rogers and Bendich, *Plant Mol. Biol.* 5:69, 1998) using SEQ ID NO:1 (forward primer) and SEQ ID NO:2 (reverse primer) in a reaction as follows: 0.5 µg template DNA, 25 pmole of each primer, taq polymerase (BMB, Indianapolis, Ind.) using wax beads for "hot start" PCR. The PCR thermocycler conditions were as follows: 94° C. for one minute; 30 cycles of: 92° C. for 40 seconds, 55° C. for one minute, 72° C. for one minute and 30 seconds; and a five minute 72° C. extension. The PCR reaction was purified using GeneClean II (Bio101 Inc., Vista, Calif.), digested with HindIII and NcoI, and ligated into construct pMON26149 (Table 1) digested with HindIII and NcoI. The promoter clone was sequence verified and the resulting construct was designated pMON26170 (Table 1).

TABLE 1

Cloning Constructs and GUS Constructs containing *Arabidopsis* Actin and EF1 promoter sequences

| Construct | Description | Promoter*/Gene/3' |
|---|---|---|
| pMON26149 | cloning construct | |
| pMON26170 | plant expression construct | Act2/GUS/nos |
| pMON26171 | plant expression construct | Act8/GUS/nos |
| pMON8677 | cloning construct | |
| pMON48407 | plant expression construct | Act11/GUS/nos |
| pMON26152 | cloning construct | |
| pMON26177 | plant expression construct | EF1/GUS/nos |
| pMON11750 | plant expression construct | e35S/GUS/nos |
| pMON15737 | plant expression construct | FMV/GUS/nos |

*the actin and elongation factor promoter sequences also contain the intron sequence from the 5' UTR of the corresponding gene.

Example 3

The *Arabidopsis* actin 8 promoter and intron (Genbank accession number U42007 as described in An et al., *Plant J.* 10:107-121, 1996) was isolated using *Arabidopsis thaliana* Landsberg erecta DNA as a template PCR conditions and purification methods described in Example 2 using primers SEQ ID NO:3 (forward primer) and SEQ ID NO:4 (reverse primer). The promoter was cloned using restriction enzymes as described in Example 2, sequence verified, and the resulting construct was designated pMON26171 (Table 1).

Example 4

The *Arabidopsis* actin 11 promoter and intron (Genbank accession number U27981 as described in Huang et al., *Plant Mol. Biol.*, 33:125-139, 1997) was isolated using *Arabidopsis thaliana* Landsberg erecta DNA as a template PCR conditions and purification methods described in Example 2 using primers SEQ ID NO:5 (forward primer) and SEQ ID NO:6 (reverse primer). The promoter was cloned using restriction enzymes EcoRV and NcoI and ligated into pMON8677 (Table 1), sequence verified, and the resulting construct was designated pMON48407 (Table 1).

Example 5

The *Arabidopsis* elongation factor 1a (AtEF1a) promoter and intron (Genbank accession number X16430 as described in Axelos et al., *Mol. Gen. Genet.* 219:106-112, 1989; Curie et al., *NAR* 19:1305-1310; Curie et al., *Plant Mol. Biol.* 18:1083-1089, 1992; Curie et al., *Mol. Gen. Genet.* 238:428-436, 1993) was isolated using *Arabidopsis thaliana* Landsberg erecta DNA as a template PCR conditions and purification methods described in Example 2 using primers SEQ ID NO:7 (forward primer) and SEQ ID NO:8 (reverse primer). The promoter was cloned using restriction enzymes HindIII and NcoI and ligated into pMON26152 (Table 1) as described in Example 2, sequence verified, and the resulting construct was designated pMON26177 (Table 1).

Example 6

The plant transformation constructs described were mated into *Agrobacterium*. Cotton transformation was performed essentially as described in WO/0036911, herein incorporated by reference in its entirety. The *Arabidopsis* transformation was performed as described in Ye et al., *Plant Journal* 19:249-257, 1999. The tomato transformation was performed as described in U.S. Pat. No. 5,565,347 herein incorporated by reference in its entirety.

Example 7

A DNA construct is transformed into a target crop of interest via an appropriate delivery system such as an *Agrobacterium*-mediated transformation method (see for example U.S. Pat. No. 5,569,834 herein incorporated by reference in its entirety, U.S. Pat. No. 5,416,011 herein incorporated by reference in its entirety, U.S. Pat. No. 5,631,152 herein incorporated by reference in its entirety, U.S. Pat. No. 5,159,135 herein incorporated by reference in its entirety, U.S. Pat. No. 5,004,863 herein incorporated by reference in its entirety, and U.S. Provisional Appln. No. 60/111,795 herein incorporated by reference in its entirety. Alternatively, a particle bombardment method may be used (see for example Patent Applns. WO 92/15675. WO 97/48814 and European Patent Appln. 586,355, and U.S. Pat. Nos. 5,120,657, 5,503,998, 5,830,728 and 5,015,580, all of which are herein incorporated by reference in their entirety).

A large number of transformation and regeneration systems and methods are available and well-known to those of skill in the art. The stably transformed plants and progeny are subsequently analyzed for expression of the gene in tissues of interest by any number of molecular, immunodiagnostic, biochemical, and/or field evaluation methods known to those of skill in the art, including, but not limited to a spray test with a glyphosate formulation at commercially effective concentrations performed in a growth chamber or field environment.

Example 8

The GUS assays are performed by routine methods known to those of skill in the art (see for example, Jefferson et al., *EMBO J.* 6:3901, 1987). For cotton, R0 plants were tested. The tissue was size selected at various stages in development, samples and pooled for analysis. The cotton floral bud was harvested and the male reproductive tissue samples (anthers and filaments), female reproductive tissue samples (entire stigma, style, and ovary), and corolla (sepals and petals) were taken. For the size selection, three floral buds from each stage were selected that included several sizes including small (less than 0.5 cm), medium (from 0.5-0.7 cm), and large (candle stage or open flower). Leaf samples were collected about 1-2 weeks after the cotton plants were placed in the greenhouse, and the other samples were collected approximately 1-2 months later. The first flowers were not collected (the first five fruiting positions were left intact).

For *Arabidopsis*, V1 plants were analyzed and only homozygous and heterozygous segregants were tested Eight to ten events per construct were analyzed (five plants per event). The GUS results for *Arabidopsis* represent pooled samples of 8-10 events. The values in the disclosed tables (Table 2 and Table 3) represent the average GUS expression for the designated tissue (pmol/MU/min/mg).

Example 9

Plants were analyzed for GUS expression in leaf tissue and reproductive tissues including immature floral buds and flowers. The results are shown in Table 2. Constructs tested included pMON48407 (P-AtAct11+intron/GUS/nos), pMON26170 (P-AtAct2+intron/GUS/nos), pMON26171 (P-AtAct8+intron/GUS/nos), pMON11750 (e35S/GUS/nos), pMON26177 (P-EF1a+intron/GUS/nos), and pMON15737 (P-FMV/GUS/nos). The actin and elongation factor promoters conferred high levels of GUS expression in multiple tissues including reproductive tissues.

TABLE 2

Average *Arabidopsis* V1 GUS Expression

| Construct | Leaf | Immature Floral Bud | Flower | Gynoecium | Andorecium |
| --- | --- | --- | --- | --- | --- |
| pMON48407 | 6944 | 7394 | 8359 | ND | ND |
| pMON26170 | 45238 | 74099 | 54502 | 73623 | 217292 |
| pMON26171 | 29343 | 35884 | 37125 | 76311 | 207100 |
| pMON11750 | 60844 | 14032 | 16263 | 35882 | 115049 |
| pMON26177 | 47598 | 72871 | 96420 | 191066 | 507370 |
| pMON15737 | 28314 | 57903 | 84457 | 44696 | 87876 |

Example 10

The R0 cotton plants were tested for expression of the GUS reporter gene in selected tissues of various stages of development. The floral buds were staged by size (small, medium, and large; large=candle and open flower). The androecium represented the male reproductive tissues including the entire receptacle (stigma, style, and ovaries). The corolla sample was composed of sepals and petals. The tissue was prepared and GUS assays performed as described in EXAMPLE 8. The results are summarized in Table 3. The constructs tested included pMON48407 (P-EF1a+intron/gus/nos), pMON26170 (P-AtAct2+intron/gus/nos), and pMON48407 (P-AtAct11+intron/gus/nos).

Six plants were tested and average GUS values obtained for pMON26177. Twenty plants were tested and average GUS values obtained for pMON26170. Eight plants were tested and average GUS values obtained for pMON48407. The results demonstrate that the actin and elongation factor promoters can be used for effective expression of operably linked genes, particularly in reproductive tissues

TABLE 3

GUS Assay Results for Cotton Plants

| Construct | Promoter/intron | Tissue Tested | GUS Results |
| --- | --- | --- | --- |
| pMON26177 | EF1a | Leaf | 11600 |
| pMON26177 | EF1a | Small Corolla | 396 |
| pMON26177 | EF1a | Small Gynoecium | 8670 |
| pMON26177 | EF1a | Small Androecium | 13771 |

TABLE 3-continued

GUS Assay Results for Cotton Plants

| Construct | Promoter/intron | Tissue Tested | GUS Results |
| --- | --- | --- | --- |
| pMON26177 | EF1a | Medium Corolla | 362 |
| pMON26177 | EF1a | Medium Gynoecium | 3318 |
| pMON26177 | EF1a | Medium Androecium | 8006 |
| pMON26177 | EF1a | Large Corolla | 351 |
| pMON26177 | EF1a | Large Gynoecium | 500 |
| pMON26177 | EF1a | Large Androecium | 15512 |
| pMON26170 | Act2 | Leaf | 12718 |
| pMON26170 | Act2 | Small Corolla | 1296 |
| pMON26170 | Act2 | Small Gynoecium | 16684 |
| pMON26170 | Act2 | Small Androecium | 7570 |
| pMON26170 | Act2 | Medium Corolla | 742 |
| pMON26170 | Act2 | Medium Gynoecium | 10041 |
| pMON26170 | Act2 | Medium Androecium | 7893 |
| pMON26170 | Act2 | Large Corolla | 289 |
| pMON26170 | Act2 | Large Gynoecium | 3218 |
| pMON26170 | Act2 | Large Androecium | 42737 |
| pMON48407 | Act11 | Leaf | 28289 |
| pMON48407 | Act11 | Small Corolla | 10 |
| pMON48407 | Act11 | Small Gynoecium | 40755 |
| pMON48407 | Act11 | Small Androecium | 47834 |
| pMON48407 | Act11 | Medium Corolla | 742 |
| pMON48407 | Act11 | Medium Gynoecium | 52495 |
| pMON48407 | Act11 | Medium Androecium | 35573 |
| pMON48407 | Act11 | Large Corolla | 1072 |
| pMON48407 | Act11 | Large Gynoecium | 4869 |
| pMON48407 | Act11 | Large Androecium | 42737 |

Example 11

Transformed plants were also tested in a greenhouse spray test using Roundup Ultra™ a glyphosate formulation with a Track Sprayer device (Roundup Ultra is a registered trademark of Monsanto Company). Plants were at the "two" true leaf or greater stage of growth and the leaves were dry before applying the Roundup® spray. The formulation used was Roundup Ultra™ as a 3 lb/gallon a.e. (acid equivalent) formulation. The calibration used was as follows:

For a 20 gallons/Acre spray volume:
Nozzle speed: 9501 evenflow
Spray pressure: 40 psi
Spray height 18 inches between top of canopy and nozzle tip
Track Speed 1.1 ft/sec., corresponding to a reading of 1950-1.0 volts.
Formulation: Roundup Ultra™ (3 lbs. A.e./gallon)

The spray concentrations will vary, depending on the desired testing ranges. For example, for a desired rate of 8 oz/acre a working solution of 3.1 ml/L is used, and for a desired rate of 64 oz/A a working range of 24.8 ml/L is used.

The evaluation period will vary, depending on the crop, stage of plant development, and tolerance level desired.

Example 12

The plant expression constructs used for tomato transformation are listed in Table 4. Tomato plants (T0) containing constructs comprising at least one actin or elongation factor promoter (with intron) operably linked to an aroA:CP4 glyphosate tolerance gene are screened in a greenhouse glyphosate spray test with glyphosate (Roundup Ultra™) formulation for the efficiency of conferring glyphosate tolerance to transgenic tomato plants. Optionally, at least one actin or elongation factor promoter sequence operably linked to an aroA:CP4 gene and an eFMV caulimovirus promoter operably linked to an aroA:CP4 transformed into tomato plants are screened by spray application with glyphosate (Roundup Ultra™). Tomato plants are sprayed with 48 oz./acre then evaluated at two weeks post application for analysis of vegetative tolerance and up to 60 days post-application for analysis of reproductive tolerance. The results are shown in Table 4 and ranked according to efficiency of selecting reproductive tolerant lines. The percent vegetative tolerance is the percentage of the lines screened that demonstrated sufficient vegetative tolerance to glyphosate damage to be considered for further studies of agronomic traits in preparation for commercially candidacy. The percent reproductive tolerance is the percentage of the vegetative tolerant lines that also demonstrated sufficient reproductive tolerance to be considered for further agronomic evaluation. All of the constructs proved functional for providing vegetative tolerance and reproductive tolerance to the transgenic tomato plants. Various combinations of promoters are able to increase the efficiency at which vegetative and reproductive tolerant lines could be selected by screening in this experiment. Constructs containing the *Arabidopsis* EF1a promoter are more specifically associated with a high percentage of vegetatively tolerant lines. P-Act2 promoter in combination with P-eFMV and P-AtEF1a (pCGN9190) provided an increase in the percentage of reproductively tolerant lines that are screened by this method.

TABLE 4

Greenhouse Track Spray Trials with Application Rate of 48 oz./Acre*

| Construct | Description | # Lines Tested | % Vegetative Tolerance[1] | % Reprod. Toler.[2] |
|---|---|---|---|---|
| pCGN9190 | eFMV/CP4 + EF1α/CP4 + Act2/CP4 | 930 | 83.2 | 52.4 |
| pCGN9153 | EF1α/CP4 + eFMV/CP4 | 391 | 73.9 | 38.9 |
| pCGN8086 | Act8/CP4 | 21 | 47.6 | 38.1 |
| pCGN8099 | FMV-EF1α/CP4 + Act8/CP4 | 71 | 84.5 | 36.6 |
| pCGN8088 | eFMV/CP4 + Act8/CP4 | 144 | 79.9 | 34.7 |
| pMON45325 | eFMV/CP4 + Act11/CP4 | 90 | 70.0 | 34.4 |
| pCGN8096 | FMV-Act11/CP4 + Act2/CP4 | 201 | 62.7 | 10.4 |
| pCGN8067 | Act2/CP4 | 205 | 67.3 | 8.8 |

*one application
[1]Pooled Results from 25 screens. Scored 14 days post-application
[2]Pooled Results from 25 screens. Scored up to 60 days post-application Tomato seed yield is used as a measure of the efficacy of the various promoter sequences and combination of expression cassettes used in the present invention for conferring glyphosate tolerance to transgenic tomato plants. In Table 5, the results of three field experiments are shown on transgenic tomato plants containing constructs with the promoters of the present invention driving expression of the aroA:CP4 coding sequence for glyphosate tolerance. Experiment 1 is a test of the plants produced from the constructs that contain the Figwort mosaic virus promoter (P-FMV) in the native and the duplicated version (P-eFMV) and additional genetic elements in the constructs that are also found in the constructs used to test the promoter sequences of the present invention. Additional genetic elements such as the source of the 5' untranslated sequence and the chloroplast transit peptide are also tested. The construct pMON20998 comprises the P-eFMV, linked to the petunia Hsp70 5' UTR, leader linked to the *Arabidopsis* EPSPS chloroplast transit peptide (CTP2), linked to the E9 3' termination region. The construct pMON20999 differs from pMON20998 only in that the promoter is P-FMV. The construct pMON10156 differs from pMON20998 only in that the CTP is from the Petunia EPSPS chloroplast transit peptide (CTP4). The construct pMON45312 differs from pMON20998 only in that the leader sequence is the native FMV leader sequence.

Tomato plants are transplanted into the field in rows. The plants are spray treated in the field at a rate of 48 oz./Acre with Roundup herbicide. The tomato seed is collected from the fruit and weighted. An unsprayed tomato line serves as the control for comparison purposes and the efficacy of each construct is expressed as a percentage of the control. The result of Experiment 1 (column 1 of Table 5) is that the FMV promoter and P-eFMV only provide 5-11% of the seed production of an unsprayed check. Experiment 2, and 3 tests the constructs of the present invention at different locations (columns 2 and 3 of Table 5). Experiment 2 is conducted at the same location as Experiment 1, the constructs pCGN8099 (FIG. 7), pCGN9151 (FIG. 11) and pCGN9190 (FIG. 5) performed well by providing 25-46% of the seed relative to an unsprayed check. At a different location that has a cooler growing season, Experiment 3 demonstrated that pCGN8068 (FIG. 9), pCGN8088 (FIG. 8), pCGN8099, pCGN9151, pCGN9153 (FIG. 6), and pMON45325 (FIG. 2) are able to confer sufficient glyphosate tolerance for the tomatoes to set 34-77% of normal seed set relative to an unsprayed check.

TABLE 5

Tomato seed yield experiments

| | Exp. 1 | | Exp. 2 | | Exp. 3 | |
|---|---|---|---|---|---|---|
| | Seed wt grams | % of Control | Seed wt grams | % of Control | Seed wt grams | % of Control |
| pMON20998 | 0.52 | 5.3 | | | | |
| pMON20999 | 0.84 | 8.6 | | | | |
| pMON10156 | 0.50 | 5.1 | | | | |
| pMON45312 | 1.07 | 11.0 | | | | |
| pCGN8068 | | | 0.48 | 8.4 | 7.06 | 77.8 |
| pCGN8088 | | | 0.43 | 7.6 | 3.09 | 34.1 |
| pCGN8096 | | | 0.40 | 7.0 | | |
| pCGN8099 | | | 1.85 | 32.5 | 6.93 | 76.4 |
| pCGN9151 | | | 1.46 | 25.7 | 6.11 | 67.4 |
| pCGN9153 | | | 0.68 | 12.0 | 4.03 | 44.4 |
| pCGN9190 | | | 2.64 | 46.4 | | |
| pMON45325 | | | 0.31 | 5.4 | 3.37 | 37.2 |
| pCGN8067 | | | | | | |
| Control | 9.73 | 100.0 | 5.69 | 100.0 | 9.07 | 100.0 |

Example 13

SEQ ID NOS: 1-8, and SEQ ID NOS:13-21 are PCR primers designed from publicly available sequence information for *Arabidopsis thaliana* Act1, Act2 (Genbank #U41998), Act3, Act7, Act8 (Genbank #ATU42007), Act11 (Genbank #ATU27981), Act12 and Elf1a (Genbank #X16430) genes. These sequences are used to extend the nucleic acid sequence using polymerase chain reaction (PCR) amplification techniques (see for example, Mullis et al., Cold Spring Harbor Symp. Quant. Biol. 51:263, 1986; Erlich, et al., European Patent Appln. 50,424; European Patent Appln. 84,796, European Patent Appln. 258,017, European Patent Appln. 237, 362; Mullis, European Patent Appln. 201,184; Mullis, et al., U.S. Pat. No. 4,683,202; Erlich, U.S. Pat. No. 4,582,788; and Saiki, et al., U.S. Pat. No. 4,683,194). A number of PCR amplification methods are known to those of skill in the art and are used to identify nucleic acid sequences adjacent to a known sequence. For example, inverse PCR (IPCR) methods, which are used to amplify unknown DNA sequences adjacent to a core region of known sequence have been described.

Other methods are also available such as capture PCR (Lagerstrom M., et al., PCR Methods Applic. 1:111, 1991), and walking PCR (Parker, et al., Nucleic Acids Res 19:3055, 1991). A number of manufacturers have also developed kits based on modifications of these methods for the purposes of identifying sequences of interest. Technical advances including improvements in primer and adaptor design, improvements in the polymerase enzyme, and thermocycler capabilities have facilitated quicker, efficient methods for isolating sequences of interest.

TABLE 5a

Primer sequences for isolation of
Arabidopsis Actin and EF1α promoter sequences

| Name | SEQ ID NO: | Sequence |
|---|---|---|
| At. Actin 2 forward | 1 | TTTTTTTTGA TATCAAGCTT CAACTATTTT TATGTATGC |
| At. Actin 2 reverse | 2 | GCCTCAGCCA TGGTGAGTCT GCTGCAAACA CACAAAAGA GTTCAAT |
| At. Actin 8 forward | 3 | TTTTTTTTGA TATCAAGCTT CCATTTTTCT TTTGCATAAT TC |
| At. Actin 8 reverse | 4 | GCATCGGCCA TGGTGAGTCT TCTGCAATCA AAAACATAAA GATCTGA |
| At. Actin 11 forward | 5 | TTTTTTTTTA AGCTTGATAT CACAACCAAA TGTCAAATGG |
| At. Actin 11 reverse | 6 | CCATCTGCCA TGGTCTATAT CCTGTC |
| At. EF1 α forward | 7 | TTTTTTTTTA AGCTTGATAT CGGAAGTTTC TCTCTTG |
| At. EF1 α reverse | 8 | CTTTTCCCAT GGTAGATCTC TGGTCAACAA ATC |
| At. Actin 1a forward | 13 | CCCAAGCTTA AATGACATCA GATACACGC |
| At. Actin 1b forward | 14 | CATAAGCTTA GAGGTCCAAA TTCA |
| At. Actin 1 reverse | 15 | CCATCAGCCA TGGTCTTCTA CCTTTATGCA AA |
| At. Actin 3 forward | 16 | CCAAGCTTAC CACACTCAGA TGCATAAACA AACACA |
| At. Actin 3 reverse | 17 | CATCAGCCAT GGTCTACTCT CTGCAAAAC A |
| At. Actin 7 forward | 18 | GCAAAGCTTA CTAGTCAACA ATTGGCC |
| At. Actin 7 reverse | 19 | GATCGGCCAT GGTTCACTAA AAAAAAG |
| At. Actin 12 forward | 20 | GGAAGCTTGC GGCCGCTTTC TACTCTACAT GTTTCT |
| At. Actin 12 reverse | 21 | GACTAGCCGC CATGGTTCAA TCTCTAGCTG A |

The leaves of young plants of *Arabidopsis thaliana* (1 g) were homogenized in 9 ml of CTAB buffer (Saghai-Maroof et al. 1984, PNAS 81:8014-8018). The CTAB buffer contained 100 mM TrisHCl, pH 7.8, 700 mM NaCl, 50 mM EDTA, 1% CTAB (alkylrimethyhyl-ammoniumbromide) and 140 mM 2-mercaptoethanol. After 90 minutes incubation in 65 C, 4.5 ml of chloroform:isoamyl alcohol (24:1) was added and samples were mixed for 10 minutes. Aqueous layer was separated by centrifugation for 10 minutes at 1500 g and was re-extracted with chloroform:isoamyl alcohol. After second centrifugation, aqueous layer was transferred to a tube containing 50 μA 10 mg/ml RNase A (DNase free) and incubated in room temperature for 30 minutes to remove RNA. DNA was precipitated with 6 ml of isopropanol and re-suspended in 1 ml of 10 mM TrisHCl buffer pH 8.5. DNA solution was extracted once with equal volume of phenol and once with an equal volume of chloroform:isoamylalcohol. After centrifugation, 1/10 volume of sodium acetate (3M, pH 5.2) was added to aqueous layer, followed by 2.5 volume of ethanol. The DNA was hooked, washed in 70% ethanol, then air dried and re-suspended in 0.2 ml of 10 mM TrisHCl buffer.

*Arabidopsis* genomic DNA (100 ng) was used in 50 μl PCR reactions. Reactions containing the primers shown in Table 5a. contained 10 μM reverse and forward primer solutions, 200 nM dNTPs and PCR buffer with magnesium and DNA polymerase mix from Expand™ High Fidelity PCR System (Roche Molecular Biochemicals). After initial 2 minute denaturation at 94° C. reactions were cycled 0.5 min at 94° C., 0.5 min at 55° C. and 1.5 minute at 72° C. for 35 times. PCR products were analyzed by electrophoresis on 1% agarose gel. Gel isolated DNA fragments representing Actin 1a, Actin 1b, Actin 7, and Actin 12 sequences were phosphorylated with T4 DNA kinase and ligated to dephosphorylated and Sma I cut pUC19 cloning construct. White colonies were screened for the presence of appropriate inserts and sequenced with M13 forward and reverse primers to confirm the presence of actin promoters. Selected clones were designated as pMON54941 (P-AtAct1a), pMON54942 (P-AtAct1b), pMON54943 (P-AtAct7) and pMON54944 (P-AtAct12). Subsequently, the Actin promoters DNA fragments were released by Hind III and NcoI digest of the pUC19 constructs containing the insert sequences, the DNA fragments were gel isolated and ligated to pMON26165 that had been digested with the same restriction enzymes. A PCR product for the Actin 3 promoter (P-AtAct3) was digested with Hind III and Nco I and cloned directly into pMON26165 to form pMON54951. pMON26165 contains the GUS/nos terminator gene segment. Ligation with the promoter segments allows for assay of each promoter for functional activity by expression of the β-glucuronidase enzyme in plant cells. The plant cells can be isolated, for example, tobacco leaf protoplasts, or the plant cells may be contained in a plant tissue or organ, such as, leaf, root, cotyledon, hypocotyl, embryo, flower, or storage organ. The expression level of GUS driven by these promoters is assayed in soybean hypocotyl in comparison with GUS driven by P-e35S promoter (Table 6). Plasmid DNA/gold particles was bombarded to soybean hypocotyls then after 48 hours the GUS activity was assayed histochemically. All of the Actin promoters tested in this assay show functional activity in the hypocotyl tissue demonstrating their utility for expression transgenes in heterologous crop plant species.

The constructs containing aroA:CP4 EPSPS driven by the *Arabidopsis* Actin 1a, (pMON54952), Actin 1b (pMON54953), Actin 3 (pMON54954), Actin 7 (pMON54955) and Actin 12 (pMON54956) promoters of the present invention were prepared in *Agrobacterium* binary plant transformation constructs for stable expression of the glyphosate resistant EPSPS in crop plants. These constructs are transformed into soybean and cotton cells, the cells are selected and regenerated into plants on glyphosate containing tissue culture media and then assayed for expression of the aroA:CP4 protein and for tolerance to glyphosate application. Plants demonstrating commercially acceptable glyphosate tolerance are further developed by conventional breeding methods to transfer the glyphosate tolerance trait into germplasm adapted for cultivation.

TABLE 6

Activity of different *Arabidopsis* actin promoters in transient assay as compare to P-e35S.

| Construct | GUS Activity |
|---|---|
| Pe35S/GUS | +++ |
| P-AtAct1a/GUS | ++ |
| P-AtAct1b/GUS | ++ |
| P-AtAct3/GUS | ++ |
| P-AtAct7/GUS | ++ |
| P-AtAct12/GUS | + |

Example 14

Cotton yield is correlated with the number of squares set during the first four to five weeks of squaring. The retention of these squares to mature bolls and their contribution to the harvest of the cotton lint is a key component of yield. When determining the efficacy of transgene constructs for conferring herbicide tolerance in cotton, the amount of boll retention is a measure of efficacy and is a desirable trait. Transgenic cotton plants containing promoters of the present invention (Table 7) were assayed in greenhouse conditions for boll retention. The promoters directed expression of the aroA:CP4 coding sequence for glyphosate tolerant phenotype. The plants were transformed by an *Agrobacterium*-mediated method or by a particle gun method. The particle gun constructs contained an additional GUS containing expression cassette useful for histochemical localization of β-glucuronidase activity from the promoters of the present invention. Transgenic plants were regenerated on glyphosate containing media and plants rooted on a rooting media. The rooted plantlets were potted in soil and transferred to a growth chamber for a hardening off period. The seed from these plant lines were collected and planted. Fifteen plants from each line were sprayed with glyphosate at 48 ounces/acre at the 4 leaf stage. At least 8 surviving plants from each line were sprayed again at the 8 leaf stage with glyphosate at 48 ounces/acre. At maturity, the number of first position bolls for the first five bolls was counted. Those lines that had 3 or more of the first position bolls retained after the glyphosate spray (plant map≥3) were advanced for further study. Table 7 illustrates the data produced from this study. The number of lines mapped indicates the number of lines surviving the first glyphosate spray application. The commercial standard is Line 1445 (pMON17136) that contains the P-FMV promoter driving expression of the CTP2-aroA:CP4 gene/E9 3', this line retains less than 1 of the 5 first bolls. The constructs, pCGN8099, pCGN9153, pCGN8088, pCGN8068 provided sufficient reproductive glyphosate tolerance in cotton such that 14-35% of the lines tested from these constructs were advanced for further agronomic trials.

TABLE 7

Greenhouse cotton boll retention study

| Construct | Promoters | # lines Mapped | Plant Map ≥3 | % ≥3 |
|---|---|---|---|---|
| pCGN8099 | FMV:EF1α + e35S:Act8 | 104 | 36 | 34.6% |
| pCGN9153 | EF1α + FMV | 36 | 12 | 33.3% |
| pCGN9165 | EF1α + 35S/GUS | 3 | 1 | 33.3 |
| pCGN9152 | EF1a | 7 | 0 | 0.0% |
| pCGN8088 | Act8 + FMV | 43 | 6 | 14.0% |
| pCGN8086 | Act8 | 7 | 0 | 0.0% |
| pCGN8068 | Act2 + FMV | 37 | 7 | 18.9% |
| pCGN8067 | Act2 | 37 | 0 | 0.0% |
| pCGN8084 | Act2 + FMV + 35S/GUS | 5 | 0 | 0.0% |
| pCGN8085 | Act2 + FMV/GUS | 1 | 0 | 0.0% |
| pCGN9164 | Act11 + 35S/GUS | 21 | 1 | 4.8% |
| pMON45325 | Act11 + FMV | 43 | 0 | 0.0% |
| pCGN8096 | FMV:Act11 + e35S:Act2 | 14 | 0 | 0.0% |
| pCGN9154 | FMV:Act11 + e35S:Act2 | 16 | 1 | 6.3% |
| Line 1445 | FMV | | <1.0 | |

Example 15

Cotton yield is correlated with the number of squares set during the first four to five weeks of squaring. The retention of these squares to mature bolls and their contribution to the harvest of the cotton lint is a key component of yield. When determining the efficacy of transgene constructs for conferring herbicide tolerance in cotton, the amount of boll retention is a measure of efficacy and is a desirable trait. Transgenic cotton plants containing promoters of the present invention were assayed in field conditions at two locations for boll retention. The transgenic cotton lines 502-254-2 (pCGN8068), 701-178-2 (pCGN8068), 53-2 (pCGN8088), 178-1 (pCGN9153), and 60-1 (pCGN9153) were compared to 1445 (glyphosate tolerance line) and PM1218BR (Paymaster 1218 parent) that contain the construct pMON17136 (P-FMV/CTP2-aroA:CP4/E93'), a wild type non-transgenic line, Coker 130 was included. The field design is a randomized complete block design consisting of 2 rows×20-30 feet×3 replications. Glyphosate is applied as Roundup Ultra™ formulation at rates of 1.12 lb ai/A=48 oz product and 1.5 lb ai/A=64 oz product at the 8 leaf stage of cotton plant development. All of the cotton plots are managed aggressively for weed and insect pest control, as well as other agronomic inputs such as planting time, fertilization, irrigation, PGR usage and defoliation. The percent boll retention is determined by mapping the location of each of the retained bolls by random selection of ten plants from the middle of the two center rows (five from each row) of each plot to map. The first mapping should be done 4 weeks after first flower (mid-season map), a second mapping should be done at harvest. The data collected includes the number of first position bolls on the bottom five flowering nodes that are counted as an indication of the reproductive tolerance of the transgenic cotton lines to glyphosate. Table 8 illustrates the advantage that promoters of the present invention have conferred to transgenic cotton plants for boll retention. This enhanced reproductive tolerance has resulted in increased lint yield (Table 9) and increased seed yield (Table 10) as well.

TABLE 8

Boll retention at mid-season plant map of bottom 5 first position bolls

|  | Location 1 | | | Location 2 | | |
| --- | --- | --- | --- | --- | --- | --- |
| | Untreated | 48 oz/A | 64 oz/A | Untreated | 48 oz/A | 64 oz/A |
| (17136) 1445 | 68 | 67 | 53 | 81 | 63 | 62 |
| (8068) 502-254-2 | 87 | 72 | 64 | 77 | 80 | 69 |
| (8068) 701-178-2 | 85 | 77 | 60 | 84 | 86 | 76 |
| (8088) 53-2 | 89 | 81 | 80 | 79 | 76 | 73 |
| (9153) 178-1 | 77 | 83 | 73 | 85 | 71 | 79 |
| (9153) 60-1 | 80 | 89 | 81 | 77 | 82 | 87 |
| PM1218BR | 92 | 56 | 63 | | | |

TABLE 9

Lint Yield (lbs/Acre) and percent yield (Location 1)

| Cultivar | Untreated | 48 oz/A | 48 oz/A % | 64 oz/A | 64 oz/A % |
| --- | --- | --- | --- | --- | --- |
| 8068-502-254-2-4 | 1103 | 960 | 87.0% | 858 | 77.8% |
| 8068-701-178-2-2 | 1326 | 1219 | 91.9% | 1177 | 88.8% |
| 9153-60-1-1 | 1177 | 1206 | 102.5% | 1171 | 99.5% |
| 9153-178-1-1 | 1112 | 769 | 69.2% | 750 | 67.4% |
| 8088-53-2-11 | 1283 | 1071 | 83.5% | 1097 | 85.5% |
| 1445 | 1018 | 563 | 55.3% | 490 | 48.1% |
| C130 | 1200 | 0 | 0.0% | 0 | 0.0% |
| PM 1218 BR | 1092 | 826 | 75.6% | 713 | 65.3% |

TABLE 10

Seed Cotton Yield (lbs/Acre) and percent yield (Location 1)

| Cultivar | Untreated | 48 oz/A | 48 oz/A % | 64 oz/A | 64 oz/A % |
| --- | --- | --- | --- | --- | --- |
| 8068-502-254-2-4 | 3357 | 2923 | 87.1% | 2646 | 78.8% |
| 8068-701-178-2-2 | 3720 | 3521 | 94.7% | 3328 | 89.5% |
| 9153-60-1-1 | 3294 | 3413 | 103.6% | 3316 | 100.7% |
| 9153-178-1-1 | 3468 | 2355 | 67.9% | 2218 | 64.0% |
| 8088-53-2-11 | 3404 | 2950 | 86.7% | 2968 | 87.2% |
| 1445 | 2835 | 1624 | 57.3% | 1372 | 48.4% |
| C130 | 3272 | 0 | 0.0% | 0 | 0.0% |
| PM 1218 B/RR | 3036 | 2192 | 72.2% | 1885 | 62.1% |

Example 16

The efficacy of the hybrid promoter P-FMV-AtEF1α driving expression of the CTP2-aroA:CP4 coding sequence (FIG. 13, pMON52059) and P-FMV/CTP2-aroA:CP4/E9 3' (pMON15737) was compared in transgenic *Arabidopsis thaliana*. The transgenic *Arabidopsis thaliana* plants were produced by the vacuum infiltration (Bechtold et al., C R Acad Paris Life Sci 316: 1194-1199) seeds were potted in soil in trays in a growth chamber adjusted for 24° C., 16 hour light (120 µE m$^{-2}$ s$^{-1}$) cycle to permit normal growth and development of the plants. The pMON52059 V1 event glyphosate tolerant transgenic *Arabidopsis* plants were selected by spray application of glyphosate herbicide at a rate of 24 ounces/acre, the surviving plants were transplanted into individual pots. Eight pMON52059 V1 plants and eight PMON 15737 homozygous plants were sprayed a second time corresponding to the observation of bolting, approximately 16 days after the at a rate of 24 ounces/acre. The second spray will determine the efficacy of the two constructs for conferring reproductive tolerance. The plants were observed for vegetative effects of glyphosate application. All plants had complete vegetative tolerance and no abnormal flowers were observed. However, abortion of siliques occurred indicated that seed had not been set in the aborted siliques. The total number of siliques produced by each plant and the siliques that contained seeds (fertile siliques) were counted and tabulated. The results are shown in Table 9 and indicate that the hybrid promoter construct pMON52059 demonstrated a greater than 10 fold improvement in fertile siliques, 89% compared to pMON15737 at 8%. The number of fertile fruiting structures is related to the amount of seed that can be produced, this is especially important in crops whose yield is associated with seed numbers. Crops such as cotton, soybean, canola, wheat, and corn are crops where reproductive tolerance to glyphosate is essential for good yield.

TABLE 11

Comparison of the hybrid promoter P-FMV-EF1α, (PMON52059) and P-FMV (PMON15737) in conferring reproductive tolerance to glyphosate in *Arabidopsis* plants.

| pMON52059 | | | | pMON15737 | | | |
| --- | --- | --- | --- | --- | --- | --- | --- |
| Plant Number | Fertile Siliques | Total Siliques | Percent Fertility | Plant Number | Fertile Siliques | Total Siliques | Percent Fertility |
| 8819 | 39 | 50 | 78.0% | 1 | 74 | 540 | 13.7% |
| 8820 | 626 | 691 | 90.6% | 2 | 23 | 600 | 3.8% |
| 8821 | 507 | 561 | 90.4% | 3 | 1 | 470 | 0.2% |
| 8822 | 0 | 69 | 0.0% | 4 | 20 | 646 | 3.1% |
| 8823 | 512 | 534 | 95.9% | 5 | 43 | 717 | 6.0% |
| 8827 | 326 | 354 | 92.1% | 6 | 22 | 651 | 3.4% |
| 8833 | 432 | 461 | 93.7% | 7 | 178 | 868 | 20.5% |
| 8838 | 323 | 374 | 86.4% | 8 | 40 | 520 | 7.7% |
| Total | 2765 | 3094 | 89.4% | Total | 401 | 5012 | 8.0% |

Example 17

Sunflower (*Helianthus annuus* L.) is a crop of agronomic importance for oil and food. The constructs pMON45325 (FIG. 2), pMON45332 (FIG. 4), and pMON45331 (FIG. 3) of the present invention were transformed into sunflower. *Agrobacterium*-mediated transformation of sunflower has been reported (Schrammeijer et al, *Plant Cell Reports*, 9: 55-60, 1990; EP 0 486 234). Methods known by those skilled in the art of plant transformation with transgene expression constructs can include hypocotyls, apical meristems, protoplasm, and other sunflower tissues. Transgenic sunflower lines SFB250-27 contains pMON20999 (P-FMV/CTP2-aroA:CP4/E93') expression cassette; SFB288-01, SFB295-09 contain pMON45325 (P-FMV/CTP2-aroA:CP4/E93'::P-AtAct11+intron/CTP2-aroA:CP4/E93'); SFB289-01 contains pMON45332 (P-AtEF1α+intron/CTP2-aroA:CP4/E93'::P-eFMV/CTP2-aroA:CP4/E93'); SFB303-08, SFB303-09, SFB303-11, and HA300B contain pMON45331 (P-AtEF1α+intron/CTP2-aroA:CP4/E9). These lines are tested for glyphosate tolerance and are shown in Table 12.

The reproductive tolerance to glyphosate in sunflower can be measured as a function of the percent of normal heads, percent normal head size and the pollen production. These plants are sprayed with Glyphosate at V-4 and V-8 leaf stages at 0, 32 oz/acre or 64 ounces/acre rate. The sunflower plants are assessed for vegetative tolerance to glyphosate. Vegetative tolerance is achieved at 32 and 64 oz/acre levels of glyphosate spray at both V4 and V8 stages of plant development.

Vegetative glyphosate tolerant transgenic sunflower lines are scored for number of heads, percent normal heads, percent normal head size, and percent normal pollen shed. These traits are scored in a field test at one location. The tabulation of the head scores and pollen production is shown in Table 12. Lines selected from the constructs of the present invention show greater percent of normal heads, generally greater percent normal head size and better pollen shed.

TABLE 12

Sunflower glyphosate resistance scores

| Line # | # heads | % normal heads | % normal head size | % pollen shed |
|---|---|---|---|---|
| SFB250-27 | 28 | 29 | 75 | 36 |
| SFB288-01 | 11 | 36 | 73 | 73 |
| SFB295-09 | 28 | 57 | 64 | 68 |
| SFB289-01 | 13 | 38 | 92 | 38 |
| SFB303-08 | 25 | 68 | 92 | 64 |
| SFB303-09 | 43 | 81 | 88 | 88 |
| SFB305-11 | 45 | 71 | 84 | 100 |
| HA300B | 30 | 100 | 97 | 97 |
| non-trans segregant | 0 | 0 | 0 | 0 |

Example 18

Cis acting regulatory elements necessary for proper promoter regulation can be identified by a number of means. In one method, deletion analysis is carried out to remove regions of the promoter and the resulting promoter fragments are assayed for promoter activity. DNA fragments are considered necessary for promoter regulation if the activity of the truncated promoter is altered compared to the original promoter fragment. Through this deletion analysis, small regions of DNA can be identified which are necessary for positive or negative regulation of transcription. Promoter sequence motifs can also be identified and novel promoters engineered to contain these cis elements for modulating expression of operably linked transcribable sequences. See for example U.S. Pat. No. 5,223,419, herein incorporated by reference in its entirety, U.S. Pat. No. 4,990,607 herein incorporated by reference in its entirety, and U.S. Pat. No. 5,097,025 herein incorporated by reference in its entirety.

An alternative approach is to look for similar sequences between promoters with similar expression profiles. Promoters with overlapping patterns of activity can have common regulatory mechanisms. Several computer programs can be used to identify conserved, sequence motifs between promoters, including but not limited to MEME, SIGNAL SCAN, or GENE SCAN. These motifs can represent binding sites for transcriptions factors which act to regulate the promoters. Once the sequence motifs are identified, their function can be assayed. For example, the motif sequences can be deleted from the promoter to determine if the motif is necessary for proper promoter function. Alternatively, the motif can be added to a minimal promoter to test whether it is sufficient to activate transcription. Suspected negative regulatory elements can be tested for sufficiency by adding to an active promoter and testing for a reduction in promoter activity. Some cis acting regulatory elements may require other elements to function. Therefore, multiple elements can be tested in various combinations by any number of methods known to those of skill in the art.

Once functional promoter elements have been identified, promoter elements can be modified at the nucleotide level to affect protein binding. The modifications can cause either higher or lower affinity binding which would affect the level of transcription from that promoter.

Promoter elements can act additively or synergistically to affect promoter activity. In this regard, promoter elements from different 5' regulatory regions can be placed in tandem to obtain a promoter with a different spectrum of activity or different expression profile. Accordingly, combinations of promoter elements from heterologous sources or duplication of similar elements or the same element can confer a higher level of expression of operably linked transcribable sequences. For example, a promoter element can be multimerized to increase levels of expression specifically in the pattern affected by that promoter element.

The technical methods needed for constructing expression constructs containing the novel engineered 5' regulatory elements are known to those of skill in the art. The engineered promoters are tested in expression constructs and tested transiently by operably linking the novel promoters to a suitable reporter gene such as GUS and testing in a transient plant assay. The novel promoters are operably linked to one or more genes of interest and incorporated into a plant transformation construct along with one or more additional regulatory elements and transformed into a target plant of interest by a suitable DNA delivery system. The stably transformed plants and subsequent progeny are evaluated by any number of molecular, immunodiagnostic, biochemical, phenotypic, or field methods suitable for assessing the desired characteristic(s).

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A nucleic acid molecule comprising a nucleotide sequence comprising SEQ ID NO: 30.

2. The nucleic acid molecule of claim 1, operably linked to a structural DNA sequence.

3. The nucleic acid molecule of claim 2, wherein the structural DNA sequence encodes an herbicide tolerance protein.

4. The nucleic acid molecule of claim 3, wherein the herbicide tolerance protein is a glyphosate tolerance protein.

5. The nucleic acid molecule of claim 4, wherein the glyphosate tolerance protein is a glyphosate oxidoreductase (GOX) protein.

6. The nucleic acid molecule of claim 4, wherein the glyphosate tolerance protein is a 5-enolpyruvyl-3-phosphoshikimate synthase (EPSPS) protein.

7. The nucleic acid molecule of claim 6, wherein the EPSPS protein is aroA:CP4 EPSPS.

8. The nucleic acid molecule of claim 4, wherein the structural DNA sequence encoding the glyphosate tolerance protein is further operably linked to a structural DNA sequence encoding a chloroplast transit peptide (CTP).

9. The nucleic acid molecule of claim 8, wherein the chloroplast transit peptide is CTP2 from *Arabidopsis*.

10. A method of controlling weeds comprising applying to a crop plant transformed with the nucleic acid molecule of claim 4 a sufficient amount of glyphosate to control weeds without damaging the crop plant.

11. The method of claim 10, wherein the crop plant is a monocot crop species.

12. The method of claim 11, wherein the monocot crop is barley, corn, rice, rye, sorghum or wheat.

13. The method of claim 10, wherein the crop plant is a dicot crop species.

14. The method of claim 13, wherein the dicot crop is a tomato, soybean, cotton, canola or sunflower.

15. A transgenic plant comprising the nucleic acid molecule of claim 1.

16. The transgenic plant of claim 15, wherein the plant is a monocot crop species.

17. The transgenic plant of claim 16, wherein the monocot crop is barley, corn, rice, rye, sorghum or wheat.

18. The transgenic plant of claim 15, wherein the plant is a dicot crop species.

19. The transgenic plant of claim 18, wherein the dicot crop is a tomato, soybean, cotton, canola or sunflower.

20. A transgenic plant seed comprising the nucleic acid molecule of claim 1.

21. The transgenic plant seed of claim 20, wherein the plant is a monocot crop species.

22. The transgenic plant seed of claim 21, wherein the monocot crop is barley, corn, rice, rye, sorghum or wheat.

23. The transgenic plant seed of claim 20, wherein the plant is a dicot crop species.

24. The transgenic plant seed of claim 23, wherein the dicot crop is a tomato, soybean, cotton, canola or sunflower.

* * * * *

SEQUENCE LISTING

```
<160> NUMBER OF SEQ ID NOS: 30

<210> SEQ ID NO 1
<211> LENGTH: 39
<212> TYPE: DNA
<213> ORGANISM: Artificial sequence
<220> FEATURE:
<223> OTHER INFORMATION: Synthetic Oligonucleotide

<400> SEQUENCE: 1
ttttttttga tatcaagctt caactatttt tatgtatgc                              39

<210> SEQ ID NO 2
<211> LENGTH: 47
<212> TYPE: DNA
<213> ORGANISM: Artificial sequence
<220> FEATURE:
<223> OTHER INFORMATION: Synthetic Oligonucleotide

<400> SEQUENCE: 2
gcctcagcca tggtgagtct gctgcaaaca cacaaaaaga gttcaat                     47

<210> SEQ ID NO 3
<211> LENGTH: 42
<212> TYPE: DNA
<213> ORGANISM: Artificial sequence
<220> FEATURE:
<223> OTHER INFORMATION: Synthetic Oligonucleotide

<400> SEQUENCE: 3
ttttttttga tatcaagctt ccatttttct tttgcataat tc                          42

<210> SEQ ID NO 4
<211> LENGTH: 47
<212> TYPE: DNA
<213> ORGANISM: Artificial sequence
<220> FEATURE:
<223> OTHER INFORMATION: Synthetic Oligonucleotide

<400> SEQUENCE: 4
gcatcggcca tggtgagtct tctgcaatca aaaacataaa gatctga                     47

<210> SEQ ID NO 5
<211> LENGTH: 40
<212> TYPE: DNA
<213> ORGANISM: Artificial sequence
<220> FEATURE:
<223> OTHER INFORMATION: Synthetic Oligonucleotide

<400> SEQUENCE: 5
ttttttttta agcttgatat cacaaccaaa tgtcaaatgg                             40

<210> SEQ ID NO 6
<211> LENGTH: 26
<212> TYPE: DNA
<213> ORGANISM: Artificial sequence
<220> FEATURE:
<223> OTHER INFORMATION: Synthetic Oligonucleotide

<400> SEQUENCE: 6
ccatctgcca tggtctatat cctgtc                                            26

<210> SEQ ID NO 7
<211> LENGTH: 37
<212> TYPE: DNA
<213> ORGANISM: Artificial sequence
```

```
<220> FEATURE:
<223> OTHER INFORMATION: Synthetic Oligonucleotide

<400> SEQUENCE: 7
ttttttttta agcttgatat cggaagtttc tctcttg                              37

<210> SEQ ID NO 8
<211> LENGTH: 33
<212> TYPE: DNA
<213> ORGANISM: Artificial sequence
<220> FEATURE:
<223> OTHER INFORMATION: Synthetic Oligonucleotide

<400> SEQUENCE: 8
cttttcccat ggtagatctc tggtcaacaa atc                                  33

<210> SEQ ID NO 9
<211> LENGTH: 1219
<212> TYPE: DNA
<213> ORGANISM: Arabidopsis Thaliana

<400> SEQUENCE: 9
caactatttt tatgtatgca agagtcagca tatgtataat tgattcagaa tcgttttgac     60
gagttcggat gtagtagtag ccattattta atgtacatac taatcgtgaa tagtgatatg    120
atgaaacatt gtatcttatt gtataaatat ccataaacac atcatgaaag acactttctt    180
tcacggtctg aattaattat gatacaattc taatagaaaa cgaattaaat tacgttgaat    240
tgtatgaaat ctaattgaac aagccaacca cgacgacgac taacgttgcc tggattgact    300
cggtttaagt taaccactaa aaaaacggag ctgtcatgta acacgcggat cgagcaggtc    360
acagtcatga agccatcaaa gcaaaagaac taatccaagg gctgagatga ttaattagtt    420
taaaaattag ttaacacgag ggaaaaggct gtctgacagc caggtcacgt tatctttacc    480
tgtggtcgaa atgattcgtg tctgtcgatt ttaattattt ttttgaaagg ccgaaaataa    540
agttgtaaga gataaacccg cctatataaa ttcatatatt ttcctctccg ctttgaattg    600
tctcgttgtc ctcctcactt tcatcagccg ttttgaatct ccggcgactt gacagagaag    660
aacaaggaag aagactaaga gagaaagtaa gagataatcc aggagattca ttctccgttt    720
tgaatcttcc tcaatctcat cttcttccgc tcttttcttc caaggtaata ggaactttct    780
ggatctactt tatttgctgg atctcgatct tgttttctca atttccttga gatctggaat    840
tcgtttaatt tggatctgtg aacctccact aaatcttttg gttttactag aatcgatcta    900
agttgaccga tcagttagct cgattatagc taccagaatt tggcttgacc ttgatggaga    960
gatccatgtt catgttacct gggaaatgat ttgtatatgt gaattgaaat ctgaactgtt   1020
gaagttagat tgaatctgaa cactgtcaat gttagattga atctgaacac tgtttaagtt   1080
agatgaagtt tgtgtataga ttcttcgaaa ctttaggatt tgtagtgtcg tacgttgaac   1140
agaaagctat ttctgattca atcagggttt atttgactgt attgaactct ttttgtgtgt   1200
ttgcagcaga ctcaccatg                                                1219

<210> SEQ ID NO 10
<211> LENGTH: 1271
<212> TYPE: DNA
<213> ORGANISM: Arabidopsis Thaliana
<220> FEATURE:
<221> NAME/KEY: misc_feature
<222> LOCATION: (535)..(536)
<223> OTHER INFORMATION: y = c or t/u
<220> FEATURE:
```

<210> SEQ ID NO 10 (continued)

<221> NAME/KEY: misc_feature
<222> LOCATION: (561)..(561)
<223> OTHER INFORMATION: y = c or t/u

<400> SEQUENCE: 10

```
ccattttttct tttgcataat tcatgtttat ttttttattt ttttcatctt gcataattca      60
tgtttaaaag gatatataca tgggtctact acattctcct gacattacgt tttatgtgtt     120
tgtcttctga aaataatcat caaaatattt caggacttgt ttacgttttc aggagaaaaa     180
aaataactgt accctttca atatagaaat aacatttgta gaaatcgtgg attttcctta     240
ataaacaatc caaacacga ccaccgttgt ctcctcgact cggtaacacc cgatcgccga     300
cttgaaaatt agaagaaaaa tgaaagaat aataaaaaaa aaaaggaat gatgattgaa     360
gctgtcatat atgtcgaccc tatcacagtc aatccaatag cctatattcg ccaactgata     420
tatccaacgg ctcacaaatt ttcacaaact tttcaaaaaa gtataataaa agaggctgtc     480
tgacagccat gtcacgttat acttttccg tatgatcgaa atgattcgtc tttgyygaat     540
ttaattattt ccaaaattga ygactctaaa gaaaaaaaaa tagttttca gataaacccg     600
cctatataaa tagttcaaca ctcggtttat ttcttctccc ctcaaagaat tgcctcgtcg     660
tcttcagctt catcggccgt tgcatttccc ggcgataaga gagagaaaga ggagaaagag     720
tgagccagtt cttcatcgtc gtggttcttg tttcttcctc gatctctcga tcttctgctt     780
ttgcttttcc gattaaggta attaaaacct ccgatctact tgttcttgtg ttggatctcg     840
attacgattt ctaagttacc ttcaaaagtt gtttccgatt tgattttgat tggaatttag     900
atcggtcaaa ctattggaaa tttttgatcc tggcaccgat tagctcaacg attcatgttt     960
gacttgatct tgcgttgtat ttgaaatcga tccggatcct ttcgcttctt ctgtcaatag    1020
gaatctgaaa tttgaaatgt tagttgaagt ttgacttcag attctgttga tttattgact    1080
gtaacatttt gtcttccgat gagtatggat tcgttgaaat ctgctttcat tatgattcta    1140
ttgatagata catcatacat tgaattgaat ctactcatga atgaaaagcc tggtttgatt    1200
aagaaagtgt tttcggtttt ctcgatcaag attcagatct ttatgttttt gattgcagat    1260
cgtagaccat g                                                         1271
```

<210> SEQ ID NO 11
<211> LENGTH: 1393
<212> TYPE: DNA
<213> ORGANISM: Arabidopsis Thaliana

<400> SEQUENCE: 11

```
acaaccaaat gtcaaatgga atgcatcaga gaccaaacct gtaagagtcc acaaaacaat      60
tcaaagaaag aatatcaaca attcagagat tcaatcctaa aacaaaaaga gaactgaaac     120
caaatcgtac ctacacgacc agtgaagata ccaatagaga gctctgttgt agaatacaac     180
acattaagcg caattagcag aaacagtctc ttcatctgcc gatttccact tgtcactact     240
ccaaaaacct cccaaaccat ttccaaaaca gacacttttg ccatgtctac atcttcccct     300
tccccgaaaa acacatcatt tccatcaacg gagtaaatat ccggcggcat atcgatgctc     360
gagaccgtcc tatcgagaaa aggcttagcc gcttccgtga ccgccggcgt tcgtggaccg     420
tgagattgct gaaacgagcg agaataagca agcctccgat cattagcagc atatccgaca     480
tcgctgctcc gatcatcagg gagctcgtta tcgcctcgag gattaaagga atggatctc     540
tccatttttct tctttgatct taaagttcca acttcggcaa atactaaaat caacagtcag     600
tcgtacaaag aaactctgct tatacagtaa agtcaatggg ccactgttct aagcccatat     660
```

```
ataattttag aagcccatag aatacaaaag agtcaagaag cattgaccgc acaagaaaaa    720
aacaattgtt aaaaagggtt ggttagtgtg tatgtatata tgaaatgcaa caaacattat    780
acagcccatt aaatatggtt gttataggta gatgtcccca ttaaggaact ttatccagcc    840
cattaaatta ctttacagag taaaagagag agagaagatt tacagttacg ttaccaaatt    900
ttcgaaatga tttaattagt aataaataaa taattaaatg tcagttactc tctttagaaa    960
gctaaataag acagctgttt ccaccaacaa cgtgactggt cgtggggtcc tccttcgttc   1020
aaagtgatat tcagaaatca acggctgaga tcttctccat caatatttat tacgggccta   1080
ttccttcctt tttaaacttt caattctccg gctcacattc tcttcttcat tcgctccgtt   1140
tctctctcaa aaactacaca cccgtaccac accaccaccc tcctcgtttc ctcagagatc   1200
ccctctctaa cttctaaggt aatcacattt ccataacgtt ccatcgtcat tgattcttca   1260
ttagtatgcg tttatgaagc ttttcaatt taattctctt tggtagatct taagattcct   1320
ctgtttcttg caaaataaag ggttcaatta tgctaatatt ttttatatca attttgacag   1380
gatatagacc atg                                                     1393
```

```
<210> SEQ ID NO 12
<211> LENGTH: 1160
<212> TYPE: DNA
<213> ORGANISM: Arabidopsis Thaliana
<220> FEATURE:
<221> NAME/KEY: misc_feature
<222> LOCATION: (565)..(565)
<223> OTHER INFORMATION: y = c or t/u
<220> FEATURE:
<221> NAME/KEY: misc_feature
<222> LOCATION: (571)..(571)
<223> OTHER INFORMATION: y = c or t/u
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t

<400> SEQUENCE: 12
ggaagtttct ctcttgaggg aggttgctcg tggaatggga cacatatggt tgttataata     60
aaccatttcc attgtcatga gattttgagg ttaatatata ctttacttgt tcattatttt    120
atttggtgtt tgaataaatg atataaatgg ctcttgataa tctgcattca ttgagatatc    180
aaatatttac tctagagaag agtgtcatat agattgatgg tccacaatca atgaaatttt    240
tgggagacga acatgtataa ccatttgctt gaataacctt aattaaaagg tgtgattaaa    300 tgatgttgt aacatgtagt actaaacatt cataaaacac aaccaaccca agaggtattg    360
agtattcacg gctaaacagg ggcataatgg taatttaaag aatgatatta ttttatgtta    420
aaccctaaca ttggtttcgg attcaacgct ataaataaaa ccactctcgt tgctgattcc    480
atttatcgtt cttattgacc ctagccgcta cacactttc tgcgatatct ctgaggtaag    540
cgttaacgta cccttaratc gttcyttttc yttttcgtct gctgatcgtt gctcatatta    600
tttcgatgat tgttggattc gatgctcttt gttgattnat cgttctgaaa attctnatct    660
gttgtttaga ttttatcgat tgttaatatc aacgtttcac tgcttctaaa cgataattta    720
ttcatgaaac tattttccca ttctgatcga tcttgttttg agattttaat tgttcgatt    780 gattgttggt tggtggatct atatacgagt gaacttgttg atttgcgtat ttaagatgta    840
```

-continued

```
tgtcgatttg aattgtgatt gggtaattct ggagtagcat aacaaatcca gtgttccctt    900
tttctaaggg taattctcgg attgtttgct ttatatctct tgaaattgcc gatttgattg    960
aatttagctc gcttagctca gatgatagag caccacaatt tttgtggtag aaatcggttt   1020
gactccgata gcggcttttt actatgattg ttttgtgtta aagatgattt tcataatggt   1080
tatatatgtc tactgttttt attgattcaa tatttgattg ttcttttttt tgcagatttg   1140
ttgaccagag atctaccatg                                               1160

<210> SEQ ID NO 13
<211> LENGTH: 29
<212> TYPE: DNA
<213> ORGANISM: Artificial sequence
<220> FEATURE:
<223> OTHER INFORMATION: Synthetic Oligonucleotide

<400> SEQUENCE: 13
cccaagctta aatgacatca gatacacgc                                       29

<210> SEQ ID NO 14
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 14
cataagctta gaggtccaaa ttca                                            24

<210> SEQ ID NO 15
<211> LENGTH: 32
<212> TYPE: DNA
<213> ORGANISM: Artificial sequence
<220> FEATURE:
<223> OTHER INFORMATION: Synthetic Oligonucleotide

<400> SEQUENCE: 15
ccatcagcca tggtcttcta cctttatgca aa                                   32

<210> SEQ ID NO 16
<211> LENGTH: 36
<212> TYPE: DNA
<213> ORGANISM: Artificial sequence
<220> FEATURE:
<223> OTHER INFORMATION: Synthetic Oligonucleotide

<400> SEQUENCE: 16
ccaagcttac cacactcaga tgcataaaca aacaca                               36

<210> SEQ ID NO 17
<211> LENGTH: 31
<212> TYPE: DNA
<213> ORGANISM: Artificial sequence
<220> FEATURE:
<223> OTHER INFORMATION: Synthetic Oligonucleotide

<400> SEQUENCE: 17
catcagccat ggtctactct ctgcaaaaac a                                    31

<210> SEQ ID NO 18
<211> LENGTH: 27
<212> TYPE: DNA
<213> ORGANISM: Artificial sequence
<220> FEATURE:
<223> OTHER INFORMATION: Synthetic Oligonucleotide
```

<400> SEQUENCE: 18
gcaaagctta ctagtcaaca attggcc                                          27

<210> SEQ ID NO 19
<211> LENGTH: 28
<212> TYPE: DNA
<213> ORGANISM: Artificial sequence
<220> FEATURE:
<223> OTHER INFORMATION: Synthetic Oligonucleotide

<400> SEQUENCE: 19
gatcggccat ggttcactaa aaaaaaag                                         28

<210> SEQ ID NO 20
<211> LENGTH: 36
<212> TYPE: DNA
<213> ORGANISM: Artificial sequence
<220> FEATURE:
<223> OTHER INFORMATION: Synthetic Oligonucleotide

<400> SEQUENCE: 20
ggaagcttgc ggccgctttc tactctacat gtttct                                36

<210> SEQ ID NO 21
<211> LENGTH: 31
<212> TYPE: DNA
<213> ORGANISM: Artificial sequence
<220> FEATURE:
<223> OTHER INFORMATION: Synthetic Oligonucleotide

<400> SEQUENCE: 21
gactagccgc catggttcaa tctctagctg a                                     31

<210> SEQ ID NO 22
<211> LENGTH: 1578
<212> TYPE: DNA
<213> ORGANISM: Arabidopsis Thaliana

<400> SEQUENCE: 22
taaatgacat cagatacacg cttgtgaacc atctttaaag tattgatgga ctcttcacta      60
tgaaagctct ctttaaaatt aattttcttt gtacatgtct ctaagcaatg tcaaattaat     120
tagaggtcca aattcaaaaa aatgtcgtat tgaatcattc cattactaaa ttggttcaat     180
gtcagattta aacagcctag ggataattta gtgagatatg agattctact ttcaacatat     240
actaatccta aatctctagc aacttttat ataagctata aatatcatga aaatgtattt      300
taatcgtttc ataatttatg cagtcacact aatggaaaaa aggccaatta ttattatttt     360
cttcagacta taaatgaaaa cataaattaa aatgcagatt agtttaaaat tttaataagt     420
aagtaaaatg cttatagcct tatacaaaat catatttgga agtttctaac attgttgcaa     480
tttgttatca caaatcacag taatatttgt atactaatta gtaattacaa ctatacacaa     540
atttaaatgg gtaatcatat atttgtgtcc agtggattga acaaatatgc tcggcccatg     600
cggaagtaat gccaattttg ggtgagtaaa gcccatgcga aattttcaca taagaaatgc     660
atgcttttg ttttcaacga catgagttgc atgctttta tcattgctta tatagttgca      720
agtttgcaac tccttgatat ttttttatg tagacactac taccaccaaa aacttttggt     780
ctgcttattc ttgttactct tgtaaaaaaa ataaatgaat tgtttatta ctccgatttg      840
atggagtctg gtttatgagg ttttatagcc tttacagaaa attgatagtt acaaaaatat     900

| | |
|---|---|
| ttttcaaaaa taaaagggta aaaccgtcat ttcaagttgt tattgttttg ggggactgga | 960 |
| tttgaaatga aatatagaac cggaaaacaa ggtgagccga agtcgaagcc tttggacccg | 1020 |
| tttttatatt tactcctccc attcccttct ccttcaatcc ttccttcctc ctcctccctt | 1080 |
| cttcttcttc ccctctttca ttttccagcc actacaaact tttctatctc tactttttt | 1140 |
| cctctcgatt tcaggtactt tttgagaccc tttgttgtga ttttcgaaca cacacccccaa | 1200 |
| ttacgtttga ttttgatcc cgcatcgatt tcaattcatc cgtttctgag tttcttttgg | 1260 |
| atctgggtgt cttgagctaa tcttttcgat ctgttgttta tcgattttac tcatgcgtat | 1320 |
| gttcattaca ccatttgtta tttgtttaat caaccaaaag actcatgttt ttcaaatgtc | 1380 |
| tttaatataa ttttttctgat tgaatttttat aatatttaca tgattctgga tccagaatat | 1440 |
| ccttcttctt cttccatttt gtcctgtatt gatttgtctt tgaaaaagga ttgttctttg | 1500 |
| tatctgtatt ggtgaaaaag gattgttatt tgttgataaa aatttgatct ttaaacaatg | 1560 |
| tttggttttg cataaagg | 1578 |

<210> SEQ ID NO 23
<211> LENGTH: 1468
<212> TYPE: DNA
<213> ORGANISM: Arabidopsis Thaliana

<400> SEQUENCE: 23

| | |
|---|---|
| ttagaggtcc aaattcaaaa aaatgtcgta ttgaatcatt ccattactaa attggttcaa | 60 |
| tgtcagattt aaacagccta gggataattt agtgagatat gagattctac tttcaacata | 120 |
| tactaatcct aaatctctag caactttta tataagctat aaatatcatg aaaatgtatt | 180 |
| ttaatcgttt cataatttat gcagtcacac taatggaaaa aaggccaatt attattattt | 240 |
| tcttcagact ataaatgaaa acataaatta aaatgcagat tagtttaaaa ttttaataag | 300 |
| taagtaaaat gcttatagcc ttatacaaaa tcatatttgg aagtttctaa cattgttgca | 360 |
| atttgttatc acaaatcaca gtaatatttg tatactaatt agtaattaca actatacaca | 420 |
| aatttaaatg ggtaatcata tatttgtgtc cagtggattg aacaaatatg ctcggcccat | 480 |
| gcggaagtaa tgccaatttt gggtgagtaa agcccatgcg aaattttcac ataagaaatg | 540 |
| catgcttttt gttttcaacg acatgagttg catgcttttt atcattgctt atatagttgc | 600 |
| aagtttgcaa ctccttgata tttttttat gtagacacta ctaccaccaa aaactttttgg | 660 |
| tctgcttatt cttgtttact atgtaaaaaa aataaatgaa ttgtttattt actccgattt | 720 |
| gatggagtct ggtttatgag gttttatagc ctttacagaa aattgatagt tacaaaaata | 780 |
| tttttcaaaa ataaagggt aaaaccgtca tttcaagttg ttattgtttt ggggggactgg | 840 |
| atttgaaatg aaatatagaa ccggaaaaca aggtgagccg aagtcgaagc ctttggaccc | 900 |
| gttttttatat ttactcctcc cattcccttc cttcaatc cttccttcct cctcctccct | 960 |
| tcttcttctt cccctctttc attttccagc cactacaaac ttttctatct ctactttttt | 1020 |
| tcctctcgat ttcaggtact tttgagacc ctttgttgtg attttcgaac acaccccca | 1080 |
| attacgtttg attttgatc ccgcatcgat ttcaattcat ccgtttctga gtttcttttg | 1140 |
| gatctgggtg tcttgagcta atcttttcga tctgttgttt atcgattta ctcatgcgta | 1200 |
| tgttcattac accatttgtt atttgtttaa tcaaccaaaa gactcatgtt tttcaaatgt | 1260 |
| ctttaatata attttttctga ttgaattta taatatttac atgattctgg atccagaata | 1320 |
| tccttcttct cttccatttt gtcctgtatt gatttgtctt tgaaaaagg attgttcttt | 1380 |
| gtatctgtat tggtgaaaaa ggattgttat ttgttgataa aaatttgatc tttaaacaat | 1440 |

| | |
|---|---|
| gtttggtttt gcataaaggt agaagacc | 1468 |

<210> SEQ ID NO 24
<211> LENGTH: 1642
<212> TYPE: DNA
<213> ORGANISM: Arabidopsis Thaliana

<400> SEQUENCE: 24

| | |
|---|---|
| tcaagcttac cacactcaga tgcataaaca aacacagcaa gaagattgcc acaaaaatca | 60 |
| taacgaaata atcaagagat agctatcaaa tcgccaccgg cgaatcatgt catactcagt | 120 |
| atcagaaaca gatatgatag ctcaaaatat ggattaataa tgttactaaa cacatggaca | 180 |
| ataatgcatc aatattgaaa gaaagaaaat ggtttagcag aagcaaaatg gtttagaaag | 240 |
| taatgaacta cacattcaca aaggtgaaga attcgtcaag cctacaataa caaatgtcta | 300 |
| tactttatga gcccacaaag agatacatca cactatctga acgaaactaa agcaacctaa | 360 |
| catagtctag aaactactaa aatgaatgtt tcaaaacaat tttaacagaa ggcaaaagtg | 420 |
| aaacaacata ctcctttgcg agaacgagga cgaggagcta attcacgtct ggtaacaaca | 480 |
| tgtcccttgt tcaacccaac gaacaaaccg gtcttcactt gtggagttgt catcttctgt | 540 |
| aaatttcata gacaacaaac aaacaaaact ttctattcaa tacaaaatca aatttacaa | 600 |
| gagacggatt cagagataat aaagagatga agagagttaa atcaaagggg attgatagaa | 660 |
| gataccctaat caatggatcg agctcctccg gtggttcaga caaagaagg acgccgactg | 720 |
| aaaattacat ttttgtatat ataccagaga gactcaagaa aaaaccctag tccagtttgg | 780 |
| gcttttattg ggccttataa attttgggtc agttttgaca aagtaaatac aaggctatag | 840 |
| ctgctttgct aacgtgatta attatttacc atttaccaaa agccttaacc gaggccgagc | 900 |
| gagaaaaaaa aacaaaaaaa aggtagaggg caagaacgtc atttccacaa ggaattgaat | 960 |
| cggaaaacga ggtgtgccga attcgaagcc tttggacccg ttttatact ttttacttg | 1020 |
| ccattcgttt tttttttgttc attggcctca tttgattact tgtttctttg atttctcctt | 1080 |
| ccatagaacc gaattgtttt cagtctgaga tttctcctgc cgagagaacg attttaatct | 1140 |
| attttcctcg gtaatgttat agcctaattt gtgtttttt cttttcctg atccggatat | 1200 |
| cgttattctg attgacaatt gtcagtttca tcttctattc tgtgaaattt tgatttttt | 1260 |
| ccgatctgtg atttcgtcat tgtatcagcg tgcttatatg cgtttgaggc gtaaatgagt | 1320 |
| gtgtacctca tttatcattt gctatgtttt ttttttttaac agagatcttc agctgtaata | 1380 |
| ttataataga ttgaattgat aacgtgattc tggatctgga atatatatat gtcacattct | 1440 |
| tcttaggatt tgattttgtc tctctttgga tattaatatt cttcactccc ttgaaaatga | 1500 |
| atctgtttat tataatgttt agatatattc cttaccggca tttgttttag cataaatatg | 1560 |
| aaacatagca ttgactgatt tgtcttttta ttattcttgt tttttttgcca aattggtctc | 1620 |
| atgttttgc agagagtaga cc | 1642 |

<210> SEQ ID NO 25
<211> LENGTH: 1241
<212> TYPE: DNA
<213> ORGANISM: Arabidopsis Thaliana
<220> FEATURE:
<221> NAME/KEY: misc_feature
<222> LOCATION: (26)..(26)
<223> OTHER INFORMATION: n is a, c, g, or t

<400> SEQUENCE: 25

```
actagtcaac aattggccaa tctttngttc taaattgcta ataaacgacc atttccgtca    60
attctccttg gttgcaacag tctacccgtc aaatgtttac taatttataa gtgtgaagtt   120
tgaattatga aaacgaaat cgtattaaaa attcacaaga ataaacaact ccatagattt    180
tcaaaaaaac agtcacgaga aaaaaccac agaccgtttg tctgctcttc tagtttttat    240
tattttcta ttaatagttt tttgttattt cgagaataaa atttgaacga tgtccgaacc    300
acaaaagccg agccgataaa tcctaagccg agcctaactt tagccgtaac catcagtcac   360
ggctcccggg ctaattcatt tgaaccgaat cataatcaac ggtttagatc aaactcaaaa   420
caatctaacg gcaacataga cgcgtcggtg agctaaaaag agtgtgaaag ccaggtcacc   480
atagcattgt ctctcccaga tttttattt gggaaataat agaagaaata gaaaaaaata    540
aaagagtgag aaaaatcgta gagctatata ttcgcacatg tactcgtttc gctttcctta   600
gtgttagctg ctgccgctgt tgtttctcct ccatttctct atctttctct ctcgctgctt   660
ctcgaatctt ctgtatcatc ttcttcttct tcaaggtgag tctctagatc cgttcgcttg   720
attttgctgc tcgttagtcg ttattgttga ttctctatgc cgatttcgct agatctgttt   780
agcatgcgtt gtggttttat gagaaaatct ttgttttggg ggttgcttgt tatgtgattc   840
gatccgtgct tgttggatcg atctgagcta attcttaagg tttatgtgtt agatctatgg   900
agtttgagga ttcttctcgc ttctgtcgat ctctcgctgt tatttttgtt ttttcagtg    960
aagtgaagtt gtttagttcg aaatgacttc gtgtatgctc gattgatctg gttttaatct  1020
tcgatctgtt aggtgttgat gtttacaagt gaattctagt gttttctctt tgagatctgt  1080
gaagtttgaa cctagttttc tcaataatca acatatgaag cgatgtttga gtttcaataa  1140
acgctgctaa tcttcgaaac taagttgtga tctgattcgt gtttacttca tgagcttatc  1200
caattcattt cggtttcatt ttacttttt tttagtgaac c                       1241
```

<210> SEQ ID NO 26
<211> LENGTH: 1313
<212> TYPE: DNA
<213> ORGANISM: Arabidopsis Thaliana

<400> SEQUENCE: 26

```
tttctactct acatgtttct tgttattagg taaagtatta ggctcttttt ttaaaaaaaa    60
tgcttaatcc tctgggtacc tcgaaaaggg aataatactc tagttagata agtgcagcga   120
tcaacatgac aaaatgaatg aatgtttgct ttaattggtg gctaaaagct aaatacacag   180
aaaagtcaaa attcaatctc aaaatcaacc cctctgtctc aatgtccct aatctatacc    240
aaaatgtcaa tttatttct tgatcatata ttccactaat taaaaataaa tccttctcta    300
atgaaatttg tcaaggcctt ggaagcctag ttttaaatat taaatggaaa ctatttcttc   360
aacaatcaca ctgttattta gtattgttgt atgttgttca ctactttctt catttgtttt   420
gtaagaaact ataataagca aaacacata ataagtctc atgtcaaata atgaatctta     480
tgcacatgct tgattatttt acttgcacat atccctatca tcattatcac atttgtcaat   540
taccgttatc atcattactc tcattcttcc cagaacttt tcagcaattt ccatacctca    600
cccactaaga tcttttaccc ttttttcttaa ttatagtttg gatagcactc ttttacatag  660
cactgaaatt tcggttgaac acataaatta ctagaaacta gaaggaaatg ttactgaaat   720
ttcactgatt gtctaaaatt gaataatcta agaaaatgg cctttttaacc ttttttcttag  780
gcccaaatgg gctcattacc actcatgctt ggtcggtgac ccgattcttc cggtaaaaca   840
gagcctaaac cgtatttttca ggttaggctg gtgttttctt aattctccaa cctaaaaata  900
```

```
gatggacacg tgtctataga ggctgagata ttggtctcaa tgaagaaaac taacggctca    960
gacccgtgta tgaacgatat taagggccaa agttgcttct gttttccaga aatttttgaa   1020
acccaatttc agggcacgat tccacaacct ctttcttttc ttctagatct acgtaaattc   1080
atcaggtaca tgttattttt tttgtttatt tgatgtcaaa attttgatca caaggaggca   1140
aaaccaatat aaatgtaacg ctaatgcgtt tgattatggt atacgtaacg aattagattt   1200
aatggttaca ttttattgtt ttagatttag ttatgagatt ggcattaatt attggtgttt   1260
cctttgaatt tgctatgttt cttatgttga tgtaatcagc tagagattga acc           1313
```

<210> SEQ ID NO 27
<211> LENGTH: 1946
<212> TYPE: DNA
<213> ORGANISM: Artificial sequence
<220> FEATURE:
<223> OTHER INFORMATION: Synthetic Nucleic Acid Sequence

<400> SEQUENCE: 27

```
aattctcagt ccaaagcctc aacaaggtca gggtacagag tctccaaacc attagccaaa     60
agctacagga gatcaatgaa gaatcttcaa tcaaagtaaa ctactgttcc agcacatgca    120
tcatggtcag taagtttcag aaaaagacat ccaccgaaga cttaaagtta gtgggcatct    180
ttgaaagtaa tcttgtcaac atcgagcagc tggcttgtgg ggaccagaca aaaaaggaat    240
ggtgcagaat tgttaggcgc acctaccaaa agcatctttg cctttattgc aaagataaag    300
cagattcctc tagtacaagt ggggaacaaa ataacgtgga aaagagctgt cctgacagcc    360
cactcactaa tgcgtatgac gaacgcagtg acgaccacaa agaattagc ttgagctcag      420 gatttagcag cattccagat tgggttcaat caacaaggta cgagccatat cactttattc    480
aaattggtat cgccaaaacc aagaaggaac tcccatcctc aaaggtttgt aaggaagaat    540
tcgatatccc cgcggccgcg ttatcacaac caaatgtcaa atggaatgca tcagagacca    600
aacctgtaag agtccacaaa acaattcaaa gaaagaatat caacaattca gagattcaat    660
cctaaaacaa aaagagaact gaaaccaaat cgtacctaca cgaccagtga agataccaat    720
agagagctct gttgtagaat acaacacatt aagcgcaatt agcagaaaca gtctcttcat    780
ctgccgattt ccacttgtca ctactccaaa aacctcccaa accatttcca aaacagacac    840
ttttgccatg tctacatctt tcccttcccc gaaaaacaca tcatttccat caacggagta    900
aatatccggc ggcatatcga tgctcgagac cgtcctatcg agaaaaggct tagccgcttc    960
cgtgaccgcc ggcgttcgtg gaccgtgaga ttgctgaaac gagcgagaat aagcaagcct   1020
ccgatcatta gcagcatatc cgacatcgct gctccgatca tcaggagct cgttatcgcc     1080 tcgaggatta aggaaatgg atctctccat tttcttcttt gatcttaaag ttccaacttc    1140
ggcaaatact aaaatcaaca gtcagtcgta caaagaaact ctgcttatac agtaaagtca    1200
atgggccact gttctaagcc catatataat tttagaagcc catagaatac aaagagtca    1260 agaagcattg accgcacaag aaaaaaacaa ttgttaaaaa gggttggtta gtgtgtatgt   1320
atatatgaaa tgcaacaaac attatacagc ccattaaata tggttgttat aggtagatgt   1380
ccccattaag gaactttatc cagcccatta aattacttta cagagtaaaa gagagagaga   1440
agatttacag ttacgttacc aaattttcga atgatttaa ttagtaataa ataaataatt     1500
aaatgtcagt tactctcttt agaaagctaa ataagacagc tgtttccacc aacaacgtga   1560
ctggtcgtgg ggtcctcctt cgttcaaagt gatattcaga aatcaacggc tgagatcttc   1620
```

```
tccatcaata tttattacgg gcctattcct tccttttta aacttcaatt ctccggctca    1680
cattctcttc ttcattcgct ccgtttctct ctcaaaaact acacaccgt accacaccac    1740 caccctcctc gtttcctcag agatcccctc tctaacttct aaggtaatca catttccata    1800
acgttccatc gtcattgatt cttcattagt atgcgtttat gaagcttttt caatttaatt    1860
ctctttggta gatcttaaga ttcctctgtt tcttgcaaaa taagggttc aattatgcta     1920 atatttttta tatcaatttt gacagg                                         1946
```

<210> SEQ ID NO 28
<211> LENGTH: 1695
<212> TYPE: DNA
<213> ORGANISM: Artificial sequence
<220> FEATURE:
<223> OTHER INFORMATION: Synthetic Nucleic Acid Sequence
<220> FEATURE:
<221> NAME/KEY: misc_feature
<222> LOCATION: (1125)..(1125)
<223> OTHER INFORMATION: y = c or t/u
<220> FEATURE:
<221> NAME/KEY: misc_feature
<222> LOCATION: (1131)..(1131)
<223> OTHER INFORMATION: y = c or t/u
<220> FEATURE:
<221> NAME/KEY: misc_feature
<222> LOCATION: (1198)..(1198)
<223> OTHER INFORMATION: n is a, c, g, or t
<220> FEATURE:
<221> NAME/KEY: misc_feature
<222> LOCATION: (1216)..(1216)
<223> OTHER INFORMATION: n is a, c, g, or t

<400> SEQUENCE: 28

```
aattctcagt ccaaagcctc aacaaggtca gggtacagag tctccaaacc attagccaaa    60
agctacagga gatcaatgaa gaatcttcaa tcaaagtaaa ctactgttcc agcacatgca    120
tcatggtcag taagtttcag aaaaagacat ccaccgaaga cttaaagtta gtgggcatct    180
ttgaaagtaa tcttgtcaac atcgagcagc tggcttgtgg ggaccagaca aaaaaggaat    240
ggtgcagaat tgttaggcgc acctaccaaa agcatctttg cctttattgc aaagataaag    300
cagattcctc tagtacaagt ggggaacaaa ataacgtgga aaagagctgt cctgacagcc    360
cactcactaa tgcgtatgac gaacgcagtg acgaccacaa agaattagc ttgagctcag     420 gatttagcag cattccagat tgggttcaat caacaaggta cgagccatat cactttattc    480
aaattggtat cgccaaaacc aagaaggaac tcccatcctc aaaggtttgt aaggaagaat    540
tcgatatcaa gcttgatatc ggaagtttct ctcttgaggg aggttgctcg tggaatggga    600
cacatatggt tgttataata aaccatttcc attgtcatga gatttgagg ttaatatata     660 ctttacttgt tcattatttt atttggtgtt tgaataaatg atataaatgg ctcttgataa    720
tctgcattca ttgagatatc aaatatttac tctagagaag agtgtcatat agattgatgg    780
tccacaatca atgaaatttt tgggagacga acatgtataa ccatttgctt gaataacctt    840
aattaaaagg tgtgattaaa tgatgtttgt aacatgtagt actaaacatt cataaaacac    900
aaccaaccca agaggtattg agtattcacg gctaaacagg ggcataatgg taatttaaag    960
aatgatatta tttatgtta aaccctaaca ttggtttcgg attcaacgct ataaataaaa     1020
ccactctcgt tgctgattcc atttatcgtt cttattgacc ctagccgcta cacactttc    1080 tgcgatatct ctgaggtaag cgttaacgta cccttaratc gttcyttttc yttttcgtct   1140
gctgatcgtt gctcatatta tttcgatgat tgttggattc gatgctcttt gttgattnat   1200
cgttctgaaa attctnatct gttgtttaga ttttatcgat tgttaatatc aacgtttcac   1260
```

```
tgcttctaaa cgataattta ttcatgaaac tattttccca ttctgatcga tcttgttttg    1320
agattttaat ttgttcgatt gattgttggt tggtggatct atatacgagt gaacttgttg    1380
atttgcgtat ttaagatgta tgtcgatttg aattgtgatt gggtaattct ggagtagcat    1440
aacaaatcca gtgttccctt tttctaaggg taattctcgg attgtttgct ttatatctct    1500
tgaaattgcc gatttgattg aatttagctc gcttagctca gatgatagag caccacaatt    1560
tttgtggtag aaatcggttt gactccgata gcggcttttt actatgattg ttttgtgtta    1620
aagatgattt tcataatggt tatatatgtc tactgttttt attgattcaa tatttgattg    1680
ttcttttttt tgcag                                                     1695

<210> SEQ ID NO 29
<211> LENGTH: 1800
<212> TYPE: DNA
<213> ORGANISM: Artificial sequence
<220> FEATURE:
<223> OTHER INFORMATION: Synthetic Nucleic Acid Sequence
<220> FEATURE:
<221> NAME/KEY: misc_feature
<222> LOCATION: (1068)..(1069)
<223> OTHER INFORMATION: y = c or t/u
<220> FEATURE:
<221> NAME/KEY: misc_feature
<222> LOCATION: (1094)..(1094)
<223> OTHER INFORMATION: y = c or t/u

<400> SEQUENCE: 29
ggtccgatgt gagactttc aacaaagggt aatatccgga aacctcctcg gattccattg       60
cccagctatc tgtcacttta ttgtgaagat agtggaaaag gaaggtggct cctacaaatg     120
ccatcattgc gataaaggaa aggccatcgt tgaagatgcc tctgccgaca gtggtcccaa     180
agatggaccc ccacccacga ggagcatcgt ggaaaaagaa gacgttccaa ccacgtcttc     240
aaagcaagtg gattgatgtg atggtccgat gtgagacttt tcaacaaagg gtaatatccg     300
gaaacctcct cggattccat tgcccagcta tctgtcactt tattgtgaag atagtggaaa     360
aggaaggtgg ctcctacaaa tgccatcatt gcgataaagg aaaggccatc gttgaagatg     420
cctctgccga cagtggtccc aaagatggac ccccacccac gaggagcatc gtggaaaaag     480
aagacgttcc aaccacgtct ctcaaagcaag tggattgatg tgatatcaag cttccatttt     540
tcttttgcat aattcatgtt tattttttta tttttttcat cttgcataat tcatgtttaa     600
aaggatatat acatgggtct actacattct cctgacatta cgtttatgt gtttgtcttc     660 tgaaaataat catcaaaata tttcaggact tgtttacgtt ttcaggagaa aaaaaataac     720
tgtacccttt tcaatataga aataacattt gtagaaatcg tggattttcc ttaataaaca     780
atccaaaaca cgaccaccgt tgtctcctcg actcggtaac acccgatcgc cgacttgaaa     840
attagaagaa aaatgaaaag aataataaaa aaaaaaaagg aatgatgatt gaagctgtca     900
tatatgtcga ccctatcaca gtcaatccaa tagcctatat tcgccaactg atatatccaa     960
cggctcacaa atttttcacaa acttttcaaa aaagtataat aaaagaggct gtctgacagc    1020
catgtcacgt tatacttttt ccgtatgatc gaaatgattc gtctttgyyg aatttaatta    1080
tttccaaaat tgaygactct aaagaaaaaa aaatagtttt tcagataaac ccgcctatat    1140
aaatagttca acactcggtt tatttcttct cccctcaaag aattgcctcg tcgtcttcag    1200
cttcatcggc cgttgcattt cccggcgata agagagagaa agaggagaaa gagtgagcca    1260
gatcttcatc gtcgtggttc ttgtttcttc ctcgatctct cgatcttctg cttttgcttt    1320
```

-continued

| | |
|---|---|
| tccgattaag gtaattaaaa cctccgatct acttgttctt gtgttggatc tcgattacga | 1380 |
| tttctaagtt accttcaaaa gttgtttccg atttgatttt gattggaatt tagatcggtc | 1440 |
| aaactattgg aaattttga tcctggcacc gattagctca acgattcatg tttgacttga | 1500 |
| tcttgcgttg tatttgaaat cgatccggat cctttcgctt cttctgtcaa taggaatctg | 1560 |
| aaatttgaaa tgttagttga agtttgactt cagattctgt tgatttattg actgtaacat | 1620 |
| tttgtcttcc gatgagtatg gattcgttga aatctgcttt cattatgatt ctattgatag | 1680 |
| atacatcata cattgaattg aatctactca tgaatgaaaa gcctggtttg attaagaaag | 1740 |
| tgttttcggt tttctcgatc aagattcaga tctttatgtt tttgattgca gatcgtagac | 1800 |

<210> SEQ ID NO 30
<211> LENGTH: 1742
<212> TYPE: DNA
<213> ORGANISM: Artificial sequence
<220> FEATURE:
<223> OTHER INFORMATION: Synthetic Nucleic Acid Sequence

<400> SEQUENCE: 30

| | |
|---|---|
| gtccgatgtg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaggaaa ggccatcgtt gaagatgcct ctgccgacag tggtcccaaa | 180 |
| gatggacccc cacccacgag gagcatcgtg aaaaagaag acgttccaac cacgtcttca | 240 |
| aagcaagtgg attgatgtga tggtccgatg tgagactttt caacaaaggg taatatccgg | 300 |
| aaacctcctc ggattccatt gcccagctat ctgtcacttt attgtgaaga gtggaaaa | 360 |
| ggaaggtggc tcctacaaat gccatcattg cgataaagga aaggccatcg ttgaagatgc | 420 |
| ctctgccgac agtggtccca agatggacc cccacccacg aggagcatcg tggaaaaaga | 480 |
| agacgttcca accacgtctt caaagcaagt ggattgatgt gatatcaagc ttcaactatt | 540 |
| tttatgtatg caagagtcag catatgtata attgattcag aatcgttttg acgagttcgg | 600 |
| atgtagtagt agccattatt taatgtacat actaatcgtg aatagtgata tgatgaaaca | 660 |
| ttgtatctta ttgtataaat atccataaac acatcatgaa agacactttc tttcacggtc | 720 |
| tgaattaatt atgatacaat tctaatagaa aacgaattaa attacgttga attgtatgaa | 780 |
| atctaattga acaagccaac cacgacgacg actaacgttg cctggattga ctcggtttaa | 840 |
| gttaaccact aaaaaaacgg agctgtcatg taacacgcgg atcgagcagg tcacagtcat | 900 |
| gaagccatca aagcaaaaga actaatccaa gggctgagat gattaattag tttaaaaatt | 960 |
| agttaacacg agggaaaagg ctgtctgaca gccaggtcac gttatctta cctgtggtcg | 1020 |
| aaatgattcg tgtctgtcga ttttaattat tttttgaaa ggccgaaaat aaagttgtaa | 1080 |
| gagataaacc cgcctatata aattcatata ttttcctctc cgctttgaat tgtctcgttg | 1140 |
| tcctcctcac tttcatcagc cgttttgaat ctccggcgac ttgacagaga agaacaagga | 1200 |
| agaagactaa gagagaaagt aagagataat ccaggagatt cattctccgt tttgaatctt | 1260 |
| cctcaatctc atcttcttcc gctctttctt tccaaggtaa taggaacttt ctggatctac | 1320 |
| tttatttgct ggatctcgat cttgtttttct caatttcctt gagatctgga attcgtttaa | 1380 |
| tttggatctg tgaacctcca ctaaatcttt tggttttact agaatcgatc taagttgacc | 1440 |
| gatcagttag ctcgattata gctaccagaa tttggcttga ccttgatgga gagatccatg | 1500 |
| ttcatgttac ctgggaaatg atttgtatat gtgaattgaa atctgaactg ttgaagttag | 1560 |
| attgaatctg aacactgtca atgttagatt gaatctgaac actgtttaag ttagatgaag | 1620 |

```
tttgtgtata gattcttcga aactttagga tttgtagtgt cgtacgttga acagaaagct    1680
atttctgatt caatcagggt ttatttgact gtattgaact cttttttgtgt gtttgcagca   1740 ga                                                                  1742
```